United States Patent
Norvell et al.

(10) Patent No.: US 8,926,607 B2
(45) Date of Patent: Jan. 6, 2015

(54) ELECTROSURGICAL INSTRUMENT EMPLOYING MULTIPLE POSITIVE TEMPERATURE COEFFICIENT ELECTRODES

(75) Inventors: David K. Norvell, Monroe, OH (US); Timothy G. Dietz, Terrace Park, OH (US); Zhifan F. Huang, Mason, OH (US); David A. Witt, Maineville, OH (US); Jeffrey L. Aldridge, Lebanon, OH (US); Raymond M. Banks, Cupertino, CA (US); Mary E. Mootoo, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1216 days.

(21) Appl. No.: 12/797,288

(22) Filed: Jun. 9, 2010

(65) Prior Publication Data
US 2011/0306965 A1    Dec. 15, 2011

(51) Int. Cl.
*A61B 18/18*  (2006.01)
*A61B 18/14*  (2006.01)
*A61B 18/00*  (2006.01)

(52) U.S. Cl.
CPC ... *A61B 18/1445* (2013.01); *A61B 2018/00077* (2013.01); *A61B 2018/00083* (2013.01); *A61B 2018/0063* (2013.01); *A61B 2018/1455* (2013.01)
USPC .................................. 606/41; 606/51; 606/52

(58) Field of Classification Search
USPC ...................................................... 606/45–52
See application file for complete search history.

(56) References Cited

U.S. PATENT DOCUMENTS

| 3,580,841 A | 5/1971 | Cadotte et al. |
| 3,703,651 A | 11/1972 | Blowers |

(Continued)

FOREIGN PATENT DOCUMENTS

| DE | 20004812 U1 | 9/2000 |
| DE | 10201569 A1 | 7/2003 |

(Continued)

OTHER PUBLICATIONS

U.S. Appl. No. 12/797,207, filed Jun. 9, 2010.

(Continued)

*Primary Examiner* — Linda Dvorak
*Assistant Examiner* — Amanda Scott

(57) ABSTRACT

An electrosurgical surgical instrument can comprise a handle and an end effector, wherein the end effector can comprise first and second jaws which can be opened and closed in order to capture tissue therebetween. In various embodiments, the first and second jaws can comprise one or more electrodes configured to apply a voltage across the tissue, wherein one or both of the first and second jaws can include a plurality of electrodes each comprised of a positive temperature coefficient material having a different switching temperature. The electrical resistances of the electrodes can increase significantly once the temperature of the electrodes exceed their switching temperatures and, owing to the increased electrical resistance, the flow of current through the electrodes can be reduced and/or prevented. In various circumstances, the different switching temperatures of the electrodes can allow some of the electrodes to switch off before the other electrodes.

14 Claims, 30 Drawing Sheets

(56) References Cited

U.S. PATENT DOCUMENTS

| | | |
|---|---|---|
| 4,005,714 A | 2/1977 | Hiltebrandt |
| 4,058,126 A | 11/1977 | Leveen |
| 4,220,154 A | 9/1980 | Semm |
| 4,237,441 A | 12/1980 | van Konynenburg et al. |
| 4,304,987 A | 12/1981 | van Konynenburg |
| 4,545,926 A | 10/1985 | Fouts, Jr. et al. |
| 4,849,133 A | 7/1989 | Yoshida et al. |
| 4,910,389 A | 3/1990 | Sherman et al. |
| 5,104,025 A | 4/1992 | Main et al. |
| 5,106,538 A | 4/1992 | Barma et al. |
| 5,108,383 A | 4/1992 | White |
| 5,205,459 A | 4/1993 | Brinkerhoff et al. |
| 5,285,945 A | 2/1994 | Brinkerhoff et al. |
| 5,309,927 A | 5/1994 | Welch |
| 5,387,207 A | 2/1995 | Dyer et al. |
| 5,395,312 A | 3/1995 | Desai |
| 5,403,312 A | 4/1995 | Yates et al. |
| 5,428,504 A | 6/1995 | Bhatla |
| 5,504,650 A | 4/1996 | Katsui et al. |
| 5,511,556 A | 4/1996 | DeSantis |
| 5,522,839 A | 6/1996 | Pilling |
| 5,558,671 A | 9/1996 | Yates |
| 5,563,179 A | 10/1996 | Stone et al. |
| 5,599,350 A | 2/1997 | Schulze et al. |
| 5,624,452 A | 4/1997 | Yates |
| 5,647,871 A | 7/1997 | Levine et al. |
| 5,665,100 A | 9/1997 | Yoon |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,716,366 A | 2/1998 | Yates |
| 5,735,848 A | 4/1998 | Yates et al. |
| 5,752,973 A | 5/1998 | Kieturakis |
| 5,755,717 A | 5/1998 | Yates et al. |
| 5,762,255 A | 6/1998 | Chrisman et al. |
| 5,800,432 A | 9/1998 | Swanson |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,880,668 A | 3/1999 | Hall |
| 5,984,938 A | 11/1999 | Yoon |
| 6,003,517 A | 12/1999 | Sheffield et al. |
| 6,013,052 A | 1/2000 | Durman et al. |
| 6,063,098 A | 5/2000 | Houser et al. |
| 6,068,629 A | 5/2000 | Haissaguerre et al. |
| 6,074,389 A | 6/2000 | Levine et al. |
| 6,099,550 A | 8/2000 | Yoon |
| 6,206,876 B1 | 3/2001 | Levine et al. |
| 6,292,700 B1 | 9/2001 | Morrison et al. |
| 6,340,878 B1 | 1/2002 | Oglesbee |
| 6,443,968 B1 | 9/2002 | Holthaus et al. |
| 6,464,702 B2 | 10/2002 | Schulze et al. |
| 6,500,176 B1 | 12/2002 | Truckai et al. |
| 6,503,248 B1 | 1/2003 | Levine |
| 6,514,252 B2 | 2/2003 | Nezhat et al. |
| 6,533,784 B2 | 3/2003 | Truckai et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,589,200 B1 | 7/2003 | Schwemberger et al. |
| 6,635,057 B2 | 10/2003 | Harano et al. |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,770,072 B1 | 8/2004 | Truckai et al. |
| 6,773,409 B2 | 8/2004 | Truckai et al. |
| 6,789,939 B2 | 9/2004 | Schrödinger et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,860,880 B2 | 3/2005 | Treat et al. |
| 6,905,497 B2 | 6/2005 | Truckai et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,066,936 B2 | 6/2006 | Ryan |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,101,372 B2 | 9/2006 | Dycus et al. |
| 7,112,201 B2 | 9/2006 | Truckai et al. |
| 7,125,409 B2 | 10/2006 | Truckai et al. |
| 7,143,925 B2 | 12/2006 | Shelton, IV et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,235,073 B2 | 6/2007 | Levine et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckal et al. |
| 7,371,227 B2 | 5/2008 | Zeiner |
| 7,381,209 B2 | 6/2008 | Truckai et al. |
| 7,404,508 B2 | 7/2008 | Smith et al. |
| 7,435,582 B2 | 10/2008 | Zimmermann et al. |
| 7,464,846 B2 | 12/2008 | Shelton, IV et al. |
| 7,510,107 B2 | 3/2009 | Timm et al. |
| 7,513,025 B2 | 4/2009 | Fischer |
| 7,550,216 B2 | 6/2009 | Ofer et al. |
| 7,588,176 B2 | 9/2009 | Timm et al. |
| 7,597,693 B2 | 10/2009 | Garrison |
| 7,604,150 B2 | 10/2009 | Boudreaux |
| 7,628,792 B2 | 12/2009 | Guerra |
| 7,641,671 B2 | 1/2010 | Crainich |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,708,751 B2 | 5/2010 | Hughes et al. |
| 7,753,904 B2 | 7/2010 | Shelton, IV et al. |
| 7,784,663 B2 | 8/2010 | Shelton, IV |
| 7,815,641 B2 | 10/2010 | Dodde et al. |
| 7,819,298 B2 | 10/2010 | Hall et al. |
| 7,832,612 B2 | 11/2010 | Baxter, III et al. |
| 7,879,035 B2 | 2/2011 | Garrison et al. |
| 7,879,070 B2 | 2/2011 | Ortiz et al. |
| 7,931,649 B2 | 4/2011 | Couture et al. |
| 7,935,114 B2 | 5/2011 | Takashino et al. |
| 2003/0078577 A1* | 4/2003 | Truckai et al. .................. 606/51 |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0158548 A1 | 8/2003 | Phan et al. |
| 2003/0216722 A1 | 11/2003 | Swanson |
| 2004/0019350 A1 | 1/2004 | O'Brien et al. |
| 2004/0138621 A1 | 7/2004 | Jahns et al. |
| 2004/0193150 A1 | 9/2004 | Sharkey et al. |
| 2004/0232196 A1 | 11/2004 | Shelton, IV et al. |
| 2005/0033278 A1 | 2/2005 | McClurken et al. |
| 2005/0085809 A1 | 4/2005 | Mucko et al. |
| 2005/0165429 A1 | 7/2005 | Douglas et al. |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0069388 A1* | 3/2006 | Truckai et al. .................. 606/45 |
| 2006/0217709 A1 | 9/2006 | Couture et al. |
| 2007/0027469 A1 | 2/2007 | Smith et al. |
| 2007/0073341 A1 | 3/2007 | Smith et al. |
| 2007/0106158 A1 | 5/2007 | Madan et al. |
| 2007/0146113 A1* | 6/2007 | Truckai et al. ............. 338/22 R |

(56) References Cited

U.S. PATENT DOCUMENTS

| | | | |
|---|---|---|---|
| 2007/0191713 A1 | 8/2007 | Eichmann et al. | |
| 2007/0208312 A1 | 9/2007 | Norton et al. | |
| 2007/0232920 A1 | 10/2007 | Kowalski et al. | |
| 2007/0232926 A1 | 10/2007 | Stulen et al. | |
| 2007/0232927 A1 | 10/2007 | Madan et al. | |
| 2007/0232928 A1 | 10/2007 | Wiener et al. | |
| 2007/0239025 A1 | 10/2007 | Wiener et al. | |
| 2007/0260242 A1 | 11/2007 | Dycus et al. | |
| 2008/0071269 A1 | 3/2008 | Hilario et al. | |
| 2008/0147062 A1* | 6/2008 | Truckai et al. | 606/51 |
| 2008/0167522 A1 | 7/2008 | Giordano et al. | |
| 2008/0188851 A1 | 8/2008 | Truckai et al. | |
| 2008/0221565 A1 | 9/2008 | Eder et al. | |
| 2008/0294158 A1 | 11/2008 | Pappone et al. | |
| 2009/0076506 A1* | 3/2009 | Baker | 606/51 |
| 2009/0076534 A1 | 3/2009 | Shelton, IV et al. | |
| 2009/0099582 A1 | 4/2009 | Isaacs et al. | |
| 2009/0125027 A1 | 5/2009 | Fischer | |
| 2009/0206140 A1 | 8/2009 | Scheib et al. | |
| 2009/0209979 A1 | 8/2009 | Yates et al. | |
| 2009/0320268 A1 | 12/2009 | Cunningham et al. | |
| 2010/0010299 A1 | 1/2010 | Bakos et al. | |
| 2010/0032470 A1 | 2/2010 | Hess et al. | |
| 2010/0036370 A1 | 2/2010 | Mirel et al. | |
| 2010/0036380 A1 | 2/2010 | Taylor et al. | |
| 2010/0036405 A1 | 2/2010 | Giordano et al. | |
| 2010/0081863 A1 | 4/2010 | Hess et al. | |
| 2010/0081864 A1 | 4/2010 | Hess et al. | |
| 2010/0081880 A1 | 4/2010 | Widenhouse et al. | |
| 2010/0081881 A1 | 4/2010 | Murray et al. | |
| 2010/0081882 A1 | 4/2010 | Hess et al. | |
| 2010/0081883 A1 | 4/2010 | Murray et al. | |
| 2010/0081995 A1 | 4/2010 | Widenhouse et al. | |
| 2010/0094323 A1 | 4/2010 | Isaacs et al. | |
| 2010/0237132 A1 | 9/2010 | Measamer et al. | |
| 2010/0264194 A1 | 10/2010 | Huang et al. | |
| 2011/0087208 A1 | 4/2011 | Boudreaux et al. | |
| 2011/0087209 A1 | 4/2011 | Boudreaux et al. | |
| 2011/0087218 A1 | 4/2011 | Boudreaux et al. | |
| 2011/0087219 A1 | 4/2011 | Boudreaux et al. | |
| 2011/0087220 A1 | 4/2011 | Felder et al. | |
| 2011/0238065 A1 | 9/2011 | Hunt et al. | |
| 2011/0251608 A1 | 10/2011 | Timm et al. | |
| 2011/0251609 A1 | 10/2011 | Johnson et al. | |
| 2011/0251612 A1 | 10/2011 | Faller et al. | |
| 2011/0251613 A1 | 10/2011 | Guerra et al. | |
| 2011/0264093 A1 | 10/2011 | Schall | |
| 2011/0282339 A1 | 11/2011 | Weizman et al. | |
| 2011/0306963 A1 | 12/2011 | Dietz et al. | |
| 2011/0306964 A1 | 12/2011 | Stulen et al. | |
| 2011/0306966 A1 | 12/2011 | Dietz et al. | |
| 2011/0306967 A1 | 12/2011 | Payne et al. | |
| 2011/0306968 A1 | 12/2011 | Beckman et al. | |
| 2011/0306972 A1 | 12/2011 | Widenhouse et al. | |
| 2011/0306973 A1 | 12/2011 | Cummings et al. | |
| 2012/0010615 A1 | 1/2012 | Cummings et al. | |
| 2012/0010616 A1 | 1/2012 | Huang et al. | |
| 2012/0012636 A1 | 1/2012 | Beckman et al. | |
| 2012/0012638 A1 | 1/2012 | Huang et al. | |
| 2012/0016413 A1 | 1/2012 | Timm et al. | |
| 2012/0022519 A1 | 1/2012 | Huang et al. | |
| 2012/0022524 A1 | 1/2012 | Timm et al. | |
| 2012/0022525 A1 | 1/2012 | Dietz et al. | |
| 2012/0022526 A1 | 1/2012 | Aldridge et al. | |
| 2012/0022527 A1 | 1/2012 | Woodruff et al. | |
| 2012/0022528 A1 | 1/2012 | White et al. | |
| 2012/0022529 A1 | 1/2012 | Shelton, IV et al. | |
| 2012/0022530 A1 | 1/2012 | Woodruff et al. | |

FOREIGN PATENT DOCUMENTS

| | | | |
|---|---|---|---|
| EP | 0705571 | A1 | 4/1996 |
| EP | 0640317 | B1 | 9/1999 |
| EP | 1532933 | B1 | 5/2008 |
| EP | 1943957 | A2 | 7/2008 |
| EP | 1849424 | B1 | 4/2009 |
| EP | 2042117 | A1 | 4/2009 |
| EP | 2060238 | A1 | 5/2009 |
| EP | 1810625 | B1 | 8/2009 |
| EP | 2090238 | A1 | 8/2009 |
| EP | 2092905 | A1 | 8/2009 |
| EP | 1747761 | B1 | 10/2009 |
| EP | 1769766 | B1 | 2/2010 |
| EP | 2151204 | A1 | 2/2010 |
| EP | 2153791 | A1 | 2/2010 |
| EP | 2243439 | A1 | 10/2010 |
| WO | WO 93/22973 | A1 | 11/1993 |
| WO | WO 96/35382 | A1 | 11/1996 |
| WO | WO 98/00069 | A1 | 1/1998 |
| WO | WO 98/57588 | A1 | 12/1998 |
| WO | WO 99/23960 | A1 | 5/1999 |
| WO | WO 99/40861 | A1 | 8/1999 |
| WO | WO 00/25691 | A1 | 5/2000 |
| WO | WO 01/28444 | A1 | 4/2001 |
| WO | WO 03/013374 | A1 | 2/2003 |
| WO | WO 03/020339 | A2 | 3/2003 |
| WO | WO 03/028541 | A2 | 4/2003 |
| WO | WO 03/030708 | A2 | 4/2003 |
| WO | WO 03/068046 | A2 | 8/2003 |
| WO | WO 2004/011037 | A2 | 2/2004 |
| WO | WO 2005/052959 | A2 | 6/2005 |
| WO | WO 2006/021269 | A1 | 3/2006 |
| WO | WO 2006/036706 | A1 | 4/2006 |
| WO | WO 2006/055166 | A2 | 5/2006 |
| WO | WO 2008/099529 | A1 | 3/2008 |
| WO | WO 2008/045348 | A2 | 4/2008 |
| WO | WO 2008/101356 | A1 | 8/2008 |
| WO | WO 2009/022614 | A1 | 2/2009 |
| WO | WO 2009/036818 | A1 | 3/2009 |
| WO | WO 2009/059741 | A1 | 5/2009 |
| WO | WO 2009/082477 | A2 | 7/2009 |
| WO | WO 2010/104755 | A1 | 9/2010 |
| WO | WO 2011/089717 | A1 | 7/2011 |

OTHER PUBLICATIONS

U.S. Appl. No. 12/797,252, filed Jun. 9, 2010.

U.S. Appl. No. 12/797,305, filed Jun. 9, 2010.

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Hörmann et al., "Reversible and irreversible denaturation of collagen fibers." Biochemistry, 10, pp. 932-937 (1971).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-induced changes in the mechanics of a collagenous tissue: pseudoelastic behavior at 37° C.," Journal of Biomechanics, 31, pp. 211-216 (1998).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

(56) References Cited

OTHER PUBLICATIONS

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg-journal&source=MI&sp=1 . . . , accessed Aug. 25, 2009.

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

Kurt Gieck & Reiner Gieck, *Engineering Formulas* § Z.7 (7th ed. 1997).

National Semiconductors Temperature Sensor Handbook—http://www.national.com/appinfo/tempsensors/files/temphb.pdf; accessed online: Apr. 1, 2011.

Glaser and Subak-Sharpe, *Integrated Circuit Engineering*, Addison-Wesley Publishing, Reading, MA (1979). (book—not attached).

U.S. Appl. No. 12/576,756, filed Oct. 9, 2009.
U.S. Appl. No. 12/576,776, filed Oct. 9, 2009.
U.S. Appl. No. 12/576,789, filed Oct. 9, 2009.
U.S. Appl. No. 12/576,808, filed Oct. 9, 2009.
U.S. Appl. No. 12/576,831, filed Oct. 9, 2009.
U.S. Appl. No. 12/836,366, filed Jul. 14, 2010.
U.S. Appl. No. 12/836,383, filed Jul. 14, 2010.
U.S. Appl. No. 12/836,396, filed Jul. 14, 2010.
U.S. Appl. No. 12/842,464, filed Jul. 23, 2010.
U.S. Appl. No. 12/842,476, filed Jul. 23, 2010.
U.S. Appl. No. 12/842,507, filed Jul. 23, 2010.
U.S. Appl. No. 12/842,518, filed Jul. 23, 2010.
U.S. Appl. No. 12/842,538, filed Jul. 23, 2010.
U.S. Appl. No. 12/842,565, filed Jul. 23, 2010.
U.S. Appl. No. 12/758,253, filed Apr. 12, 2010.
U.S. Appl. No. 12/758,268, filed Apr. 12, 2010.
U.S. Appl. No. 12/758,284, filed Apr. 12, 2010.
U.S. Appl. No. 12/758,298, filed Apr. 12, 2010.
U.S. Appl. No. 12/765,175, filed Apr. 22, 2010.
U.S. Appl. No. 12/911,943, filed Oct. 26, 2010.
U.S. Appl. No. 12/841,480, filed Jul. 22, 2010.
U.S. Appl. No. 12/963,001, filed Dec. 8, 2010.
U.S. Appl. No. 12/732,992, filed Mar. 26, 2010.
U.S. Appl. No. 12/841,370, filed Jul. 22, 2010.
U.S. Appl. No. 12/797,844, filed Jun. 10, 2010.
U.S. Appl. No. 12/797,853, filed Jun. 10, 2010.
U.S. Appl. No. 12/797,861, filed Jun. 10, 2010.
U.S. Appl. No. 12/797,866, filed Jun. 10, 2010.
U.S. Appl. No. 12/832,345, filed Jul. 8, 2010.
U.S. Appl. No. 12/832,361, filed Jul. 8, 2010.
U.S. Appl. No. 12/781,243, filed May 17, 2010.
U.S. Appl. No. 12/775,724, filed May 7, 2010.
U.S. Appl. No. 12/622,113, filed Nov. 19, 2009.
U.S. Appl. No. 12/635,415, filed Dec. 10, 2009.
U.S. Appl. No. 12/647,134, filed Dec. 24, 2009.

International Search Report for PCT/US2011/039239, Dec. 12, 2011 (7 pages).

Wright, et al., "Time-Temperature Equivalence of Heat-Induced Changes in Cells and Proteins," Feb. 1998. ASME Journal of Biomechanical Engineering, vol. 120, pp. 22-26.

Partial International Search Report for PCT/US2011/039239, Sep. 1, 2011 (2 pages).

U.S. Appl. No. 13/221,410, filed Aug. 30, 2011.
U.S. Appl. No. 13/169,169, filed Jul. 22, 2011.

* cited by examiner

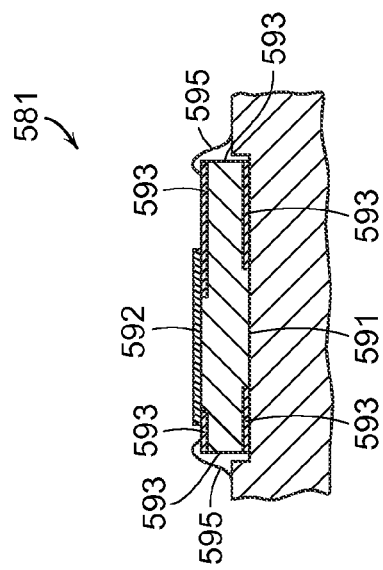
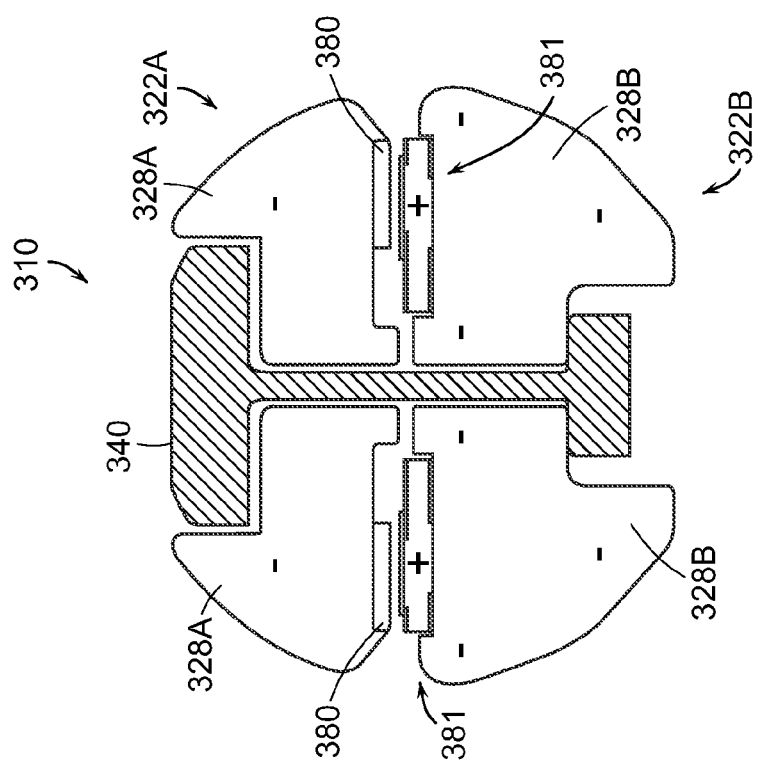

ELECTROSURGICAL INSTRUMENT EMPLOYING MULTIPLE POSITIVE TEMPERATURE COEFFICIENT ELECTRODES

BACKGROUND

1. Field of the Invention

The present invention relates to medical devices and methods. More particularly, the present invention relates to electrosurgical instruments and methods for sealing and transecting tissue.

2. Description of the Related Art

In various open, endoscopic, and/or laparoscopic surgeries, for example, it may be necessary to coagulate, seal, and/or fuse tissue. One means of sealing tissue relies upon the application of electrical energy to tissue captured within an end effector of a surgical instrument in order to cause thermal effects within the tissue. Various mono-polar and bi-polar radio frequency (Rf) surgical instruments and surgical techniques have been developed for such purposes. In general, the delivery of Rf energy to the captured tissue elevates the temperature of the tissue and, as a result, the energy can at least partially denature proteins within the tissue. Such proteins, such as collagen, for example, may be denatured into a proteinaceous amalgam that intermixes and fuses, or "welds", together as the proteins renature. As the treated region heals over time, this biological "weld" may be reabsorbed by the body's wound healing process.

In certain arrangements of a bi-polar radiofrequency (Rf) surgical instrument, the surgical instrument can comprise opposing first and second jaws, wherein the face of each jaw can comprise an electrode. In use, the tissue can be captured between the jaw faces such that electrical current can flow between the electrodes in the opposing jaws and through the tissue positioned therebetween. Such instruments may have to seal or "weld" many types of tissues, such as anatomic structures having walls with irregular or thick fibrous content, bundles of disparate anatomic structures, substantially thick anatomic structures, and/or tissues with thick fascia layers such as large diameter blood vessels, for example. With particular regard to sealing large diameter blood vessels, for example, such applications may require a high strength tissue weld immediately post-treatment.

The foregoing discussion is intended only to illustrate various aspects of the related art in the field of the invention at the time, and should not be taken as a disavowal of claim scope.

SUMMARY

In at least one form, a surgical instrument can comprise a handle, a first conductor, a second conductor, and an end effector comprising a first jaw and a second jaw, wherein one of the first jaw and the second jaw is movable relative to the other of the first jaw and the second jaw between an open position and a closed position. The end effector can further comprise a first electrode electrically coupled with the first conductor, and a second electrode electrically coupled with the second conductor, the second electrode comprising a porous material, and an evaporable material stored within the porous material.

In at least one form, a surgical instrument can comprise a handle, a first conductor, a second conductor electrically engageable with a power source, and an end effector comprising a first jaw and a second jaw, wherein one of the first jaw and the second jaw is movable relative to the other of the first jaw and the second jaw between an open position and a closed position. The end effector can further comprise a first electrode electrically coupled with the first conductor, and a second electrode electrically coupled with the second conductor, wherein the second electrode comprises a first material comprised of an electrically non-conductive material and a second material comprised of an electrically conductive material, and wherein the second material is interdispersed within the first material when the second electrode is below a switching temperature. The second material is configured to withdraw from the first material when the temperature of the second material at least one of meets or exceeds the switching temperature.

In at least one form, an end effector for use with a surgical instrument can comprise a first conductor, a second conductor, a first jaw, and a second jaw, wherein one of the first jaw and the second jaw is movable relative to the other of the first jaw and the second jaw between an open position and a closed position. The end effector can further comprise a first electrode electrically coupled with the first conductor and a second electrode electrically coupled with the second conductor, the second electrode comprising a porous material and an evaporable material stored within the porous material.

In at least one form, a surgical instrument can comprise a first jaw comprising an electrode, a second jaw, and a control circuit, wherein the control circuit can comprise a supply conductor configured to be placed in electrical communication with a positive terminal of a power source, a temperature sensor, and a field effect transistor. The field effect transistor can comprise a source terminal in electrical communication with the supply conductor, a drain terminal in electrical communication with the electrode, a gate terminal in electrical communication with the temperature sensor, and a channel comprising a semiconductor material in electrical communication with the source terminal and the drain terminal.

In at least one form, a surgical instrument can comprise a handle, a first conductor, a second conductor, and an end effector. The end effector can comprise a first jaw, a second jaw, wherein the first jaw is movable relative to the second jaw in order to capture tissue intermediate the first jaw and the second jaw, a first electrode electrically coupled with the first conductor, and a second electrode electrically coupled with the second conductor, wherein the second electrode is comprised of a material configured to conduct a first current when a first pressure is applied to the material, and wherein the material is configured to conduct a second current when a second pressure is applied to the material.

In various embodiments, the material can comprise a substrate material and a conductive material interdispersed within the substrate material in a first volumetric density when the first pressure is being applied to the material and a second volumetric density when the second pressure is being applied to the material, and wherein the second volumetric density is greater than the first volumetric density. In certain embodiments, the second electrode can further comprise a positive temperature coefficient (PTC) material having a switching temperature, wherein the PTC material comprises a first electrical resistance at a first temperature below the switching temperature and a second electrical resistance at a second temperature above the switching temperature, and wherein the second resistance is sufficient to inhibit the conduction of electrical current therethrough.

In at least one form, a surgical instrument can comprise a handle, a first conductor, a second conductor, and an end effector. The end effector can comprise a first jaw, a second jaw, wherein the first jaw is movable relative to the second jaw in order to capture tissue intermediate the first jaw and the second jaw, a first electrode electrically coupled with the first conductor, and a second electrode electrically coupled with the second conductor, wherein the second electrode is comprised of a material configured to conduct a first current when a first pressure is applied to the material, and wherein the material is configured to inhibit current from flowing through the material when a second pressure is applied to the material.

In at least one form, a surgical instrument can comprise a handle, a first conductor, a second conductor, and an end effector. The end effector can comprise a first jaw, a second jaw, wherein the first jaw is movable relative to the second jaw in order to capture tissue intermediate the first jaw and the second jaw, a first electrode electrically coupled with the first conductor, and a second electrode electrically coupled with the second conductor, wherein the second electrode is comprised of a material configured to have a first electrical resistance when a first pressure is applied to the material, and wherein the material is configured to have a second electrical resistance when a second pressure is applied to the material.

In at least one form, a surgical instrument can comprise a handle and an end effector, wherein the end effector can comprise a first jaw and a second jaw, and wherein the first jaw is movable relative to the second jaw between an open position and a closed position. The end effector can further comprise a first electrode comprised of a first positive temperature coefficient material having a first electrical resistance when the temperature of the first electrode is below a first switching temperature and a second electrical resistance when the temperature of the first electrode is above the first switching temperature. The end effector can further comprise a second electrode comprised of a second positive temperature coefficient material having a first electrical resistance when the temperature of the second electrode is below a second switching temperature and a second electrical resistance when the temperature of the second electrode is above the second switching temperature, wherein the second switching temperature is higher than the first switching temperature.

In at least one form, a surgical instrument can comprise a handle and an end effector, wherein the end effector can comprise a first jaw and a second jaw, and wherein the first jaw is movable relative to the second jaw. The end effector can further comprise a first electrode comprised of a first positive temperature coefficient material having a first electrical resistance when the temperature of said first electrode is below a first switching temperature and a second electrical resistance at least one order of magnitude higher than said first resistance when the temperature of the first electrode is above the first switching temperature. The end effector can further comprise a second electrode comprised of a second positive temperature coefficient material having a third electrical resistance when the temperature of the second electrode is below a second switching temperature and a fourth electrical resistance at least one order of magnitude higher than the third electrical resistance when the temperature of the second electrode is above the second switching temperature, wherein the second switching temperature is higher than the first switching temperature.

In at least one form, a surgical instrument can comprise a handle and an end effector, wherein the end effector can comprise a first jaw comprising a first frame having a first outer perimeter and a first electrode positioned within the first frame. The end effector can further comprise a second jaw, wherein one of the first jaw and the second jaw is movable relative to the other of the first jaw and the second jaw between an open position and a closed position, the second jaw comprising a second frame having a second outer perimeter and a second electrode positioned within said second frame. At least one of the first outer perimeter and the second outer perimeter is comprised of a positive temperature coefficient material, wherein the positive temperature coefficient material comprises a first electrical resistance when the temperature of the positive temperature coefficient material is below a switching temperature and a second electrical resistance when the temperature of the positive temperature coefficient material is above the switching temperature.

In at least one form, a surgical instrument can comprise a handle and an end effector, the end effector comprising a first jaw and a second jaw, wherein one of the first jaw and the second jaw is movable relative to other of the first jaw and the second jaw. The end effector can further comprise a first electrode positioned within the second jaw, a second electrode positioned within the second jaw, and a third electrode comprised of a positive temperature coefficient material positioned within the first jaw, wherein the positive temperature coefficient material comprises a first electrical resistance when the temperature of said third electrode is below a switching temperature and a second electrical resistance higher than the first resistance when the temperature of the third electrode is above the switching temperature. The surgical instrument can further comprise a controller configured to selectively electrically couple the first electrode and the second electrode with a power source.

In at least one form, a method of operating an electrosurgical instrument can comprise the steps of moving a first jaw toward a second jaw in order to capture tissue between the first jaw and the second jaw, wherein the second jaw comprises a first electrode and a second electrode, and wherein the first jaw comprises an opposing electrode positioned opposite the first electrode and the second electrode. The method further comprises the steps of applying a voltage potential to the first electrode such that current can flow between the first electrode and the opposing electrode and can contract the tissue positioned between the first electrode and the opposing electrode, and applying a voltage potential to the second electrode after the voltage potential has been at least initially applied to the first electrode. In addition, the method can further comprise advancing a cutting member relative to the first electrode and the second electrode.

The foregoing discussion should not be taken as a disavowal of claim scope.

BRIEF DESCRIPTION OF THE DRAWINGS

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 5 is a cross-sectional view of an end effector including a first jaw comprising electrodes and a second jaw positioned opposite the first jaw.

FIG. 10 is a cross-sectional detail view of an electrode that can be utilized with the end effector of FIG. 5.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
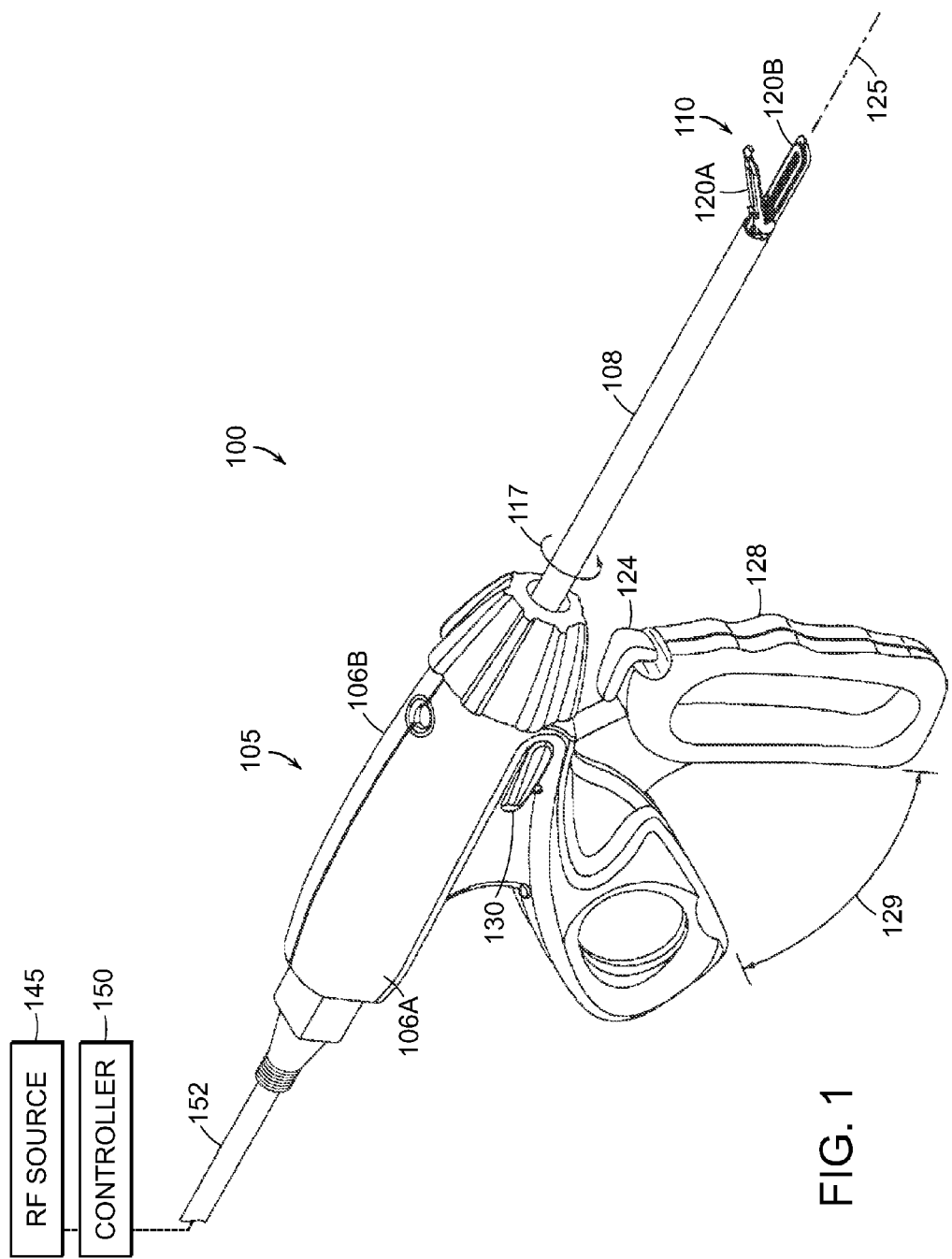
FIG. 1 is a perspective view of an electrosurgical instrument.

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

The entire disclosures of the following non-provisional United States patents are hereby incorporated by reference herein:

U.S. Pat. No. 7,381,209, entitled ELECTROSURGICAL INSTRUMENT;

U.S. Pat. No. 7,354,440, entitled ELECTROSURGICAL INSTRUMENT AND METHOD OF USE;

U.S. Pat. No. 7,311,709, entitled ELECTROSURGICAL INSTRUMENT AND METHOD OF USE;

U.S. Pat. No. 7,309,849, entitled POLYMER COMPOSITIONS EXHIBITING A PTC PROPERTY AND METHODS OF FABRICATION;

U.S. Pat. No. 7,220,951, entitled SURGICAL SEALING SURFACES AND METHODS OF USE;

U.S. Pat. No. 7,189,233, entitled ELECTROSURGICAL INSTRUMENT;

U.S. Pat. No. 7,186,253, entitled ELECTROSURGICAL JAW STRUCTURE FOR CONTROLLED ENERGY DELIVERY;

U.S. Pat. No. 7,169,146, entitled ELECTROSURGICAL PROBE AND METHOD OF USE;

U.S. Pat. No. 7,125,409, entitled ELECTROSURGICAL WORKING END FOR CONTROLLED ENERGY DELIVERY; and U.S. Pat. No. 7,112,201, entitled ELECTROSURGICAL INSTRUMENT AND METHOD OF USE.

The entire disclosures of the following co-pending non-provisional United States patent applications filed on even date herewith are hereby incorporated by reference herein:

U.S. patent application Ser. No. 12/797,207, entitled ELECTROSURGICAL INSTRUMENT EMPLOYING AN ELECTRODE, now U.S. Patent Publication No. 2011/0306963;

U.S. patent application Ser. No. 12/797,252, entitled ELECTROSURGICAL INSTRUMENT EMPLOYING PRESSURE-VARIATION ELECTRODES, now U.S. Patent Publication No. 2011/0306964; and U.S. patent application Ser. No. 12/797,305, entitled ELECTROSURGICAL INSTRUMENT EMPLOYING A PLURALITY OF ELECTRODES, now U.S. Patent Publication No. 2011/0306966.

Various embodiments of systems and methods of the invention relate to creating thermal "welds" or "fusion" within native tissue volumes. The alternative terms of tissue "welding" and tissue "fusion" may be used interchangeably herein to describe thermal treatments of a targeted tissue volume that result in a substantially uniform fused-together tissue mass, for example, in welding blood vessels that exhibit substantial burst strength immediately post-treatment. The strength of such welds is particularly useful for (i) permanently sealing blood vessels in vessel transection procedures; (ii) welding organ margins in resection procedures; (iii) welding other anatomic ducts wherein permanent closure is required; and also (iv) for performing vessel anastomosis, vessel closure or other procedures that join together anatomic structures or portions thereof. The welding or fusion of tissue as disclosed herein is to be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

At the molecular level, the phenomena of truly "welding" tissue as disclosed herein may result from the thermally-induced denaturation of collagen and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

Various embodiments disclosed herein provide electrosurgical jaw structures adapted for transecting captured tissue between the jaws and for contemporaneously welding the captured tissue margins with controlled application of RF energy. The jaw structures can comprise a scoring element which can cut or score tissue independently of the tissue capturing and welding functions of the jaw structures. The jaw structures can comprise first and second opposing jaws that carry positive temperature coefficient (PTC) bodies for modulating RF energy delivery to the engaged tissue.

A surgical instrument can be configured to supply energy, such as electrical energy, ultrasonic energy, and/or heat energy, for example, to the tissue of a patient. For example, various embodiments disclosed herein can comprise electrosurgical jaw structures adapted for transecting captured tissue positioned between the jaws and for contemporaneously welding margins of the captured tissue with the controlled application of RF energy, for example. Referring now to FIG. 1, an electrosurgical instrument 100 is shown. Electrosurgical instrument 100 can comprise a proximal handle 105, a distal working end or end effector 110, and an introducer or elongate shaft 108 disposed therebetween. End effector 110 may comprise a set of openable and closeable jaws, such as an upper first jaw 120A and a lower second jaw 120B, for example, which can comprise straight and/or curved configurations. First jaw 120A and second jaw 120B may each comprise an elongate slot or channel 142A and 142B (see FIG. 3), respectively, therein disposed within their respective middle portions along axis 125, for example. As described in greater detail below, first jaw 120A and second jaw 120B may be coupled to an electrical source or RF source 145 and a controller 150 through electrical leads in cable 152. Controller 150 may be used to activate electrical source 145. In various embodiments, the electrical source 145 may comprise an RF source, an ultrasonic source, a direct current source, and/or any other suitable type of electrical energy source, for example.

Figure 2:
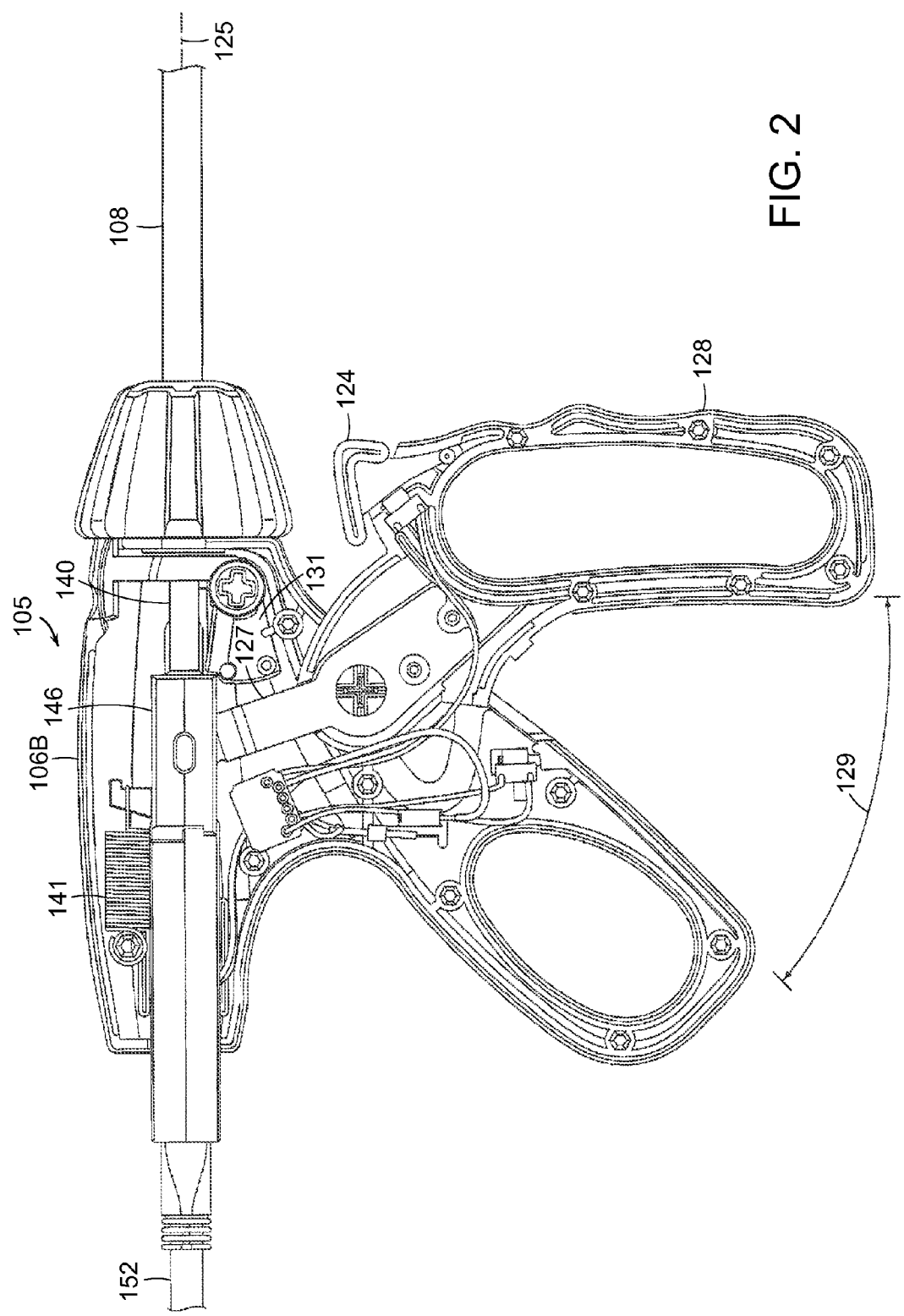
FIG. 2 is a side view of a handle of the surgical instrument of FIG. 1 with a half of a handle body removed to illustrate some of the components therein.

Moving now to FIG. 2, a side view of the handle 105 is shown with a first handle body 106A (see FIG. 1) removed to illustrate some of the components within second handle body 106B. Handle 105 may comprise a lever arm, or trigger, 128 which may be pulled along a path 129. Lever arm 128 may be coupled to a movable cutting member disposed within elongate shaft 108 by a shuttle 146 operably engaged to an extension 127 of lever arm 128. The shuttle 146 may further be connected to a biasing device, such as spring 141, for example, which may also be connected to the second handle body 106B, wherein the spring 141 can be configured to bias the shuttle 146 and thus the cutting member in a proximal direction. When the cutting member is in a proximal position, the jaws 120A and 120B can be urged into an open configuration as seen in FIG. 1 by a jaw spring disposed between a portion of the jaws 120A and 120B, for example. Also, referring to FIGS. 1 and 2, a locking member 131 (see FIG. 2) may be moved by a locking switch 130 (see FIG. 1) between a locked position in which the shuttle 146 can be prevented from moving distally and an unlocked position in which the shuttle 146 may be allowed to freely move in the distal direction toward the elongate shaft 108. The handle 105 can be any type of pistol-grip or other type of handle known in the art that is configured to carry actuator levers, triggers and/or sliders for actuating the first jaw 120A. Elongate shaft 108 may have a cylindrical and/or rectangular cross-section and can comprise a thin-wall tubular sleeve that extends from handle 105. Elongate shaft 108 may include a bore extending therethrough for carrying actuator mechanisms configured to actuate the jaws and/or for carrying electrical leads configured to conduct electrical energy to electrosurgical components of end effector 110.

End effector 110 may be adapted for capturing, welding and transecting tissue. In various embodiments, at least one of first jaw 120A and second jaw 120B may be closed to capture or engage tissue therebetween. First jaw 120A and second jaw 120B may also apply compression to the tissue. Elongate shaft 108, along with first jaw 120A and second jaw 120B, can be rotated a full 360° degrees, as shown by arrow 117, relative to handle 105 through one or more rotary contacts, for example. First jaw 120A and second jaw 120B can remain openable and/or closeable while rotated. Referring now to FIG. 1, end effector 110 may be coupled to electrical source 145 and controller 150. Controller 150 can regulate the electrical energy delivered by electrical source 145 which in turn delivers electrosurgical energy to electrodes within the jaws 120A, 120B. The energy delivery may be initiated by an activation button 124 operably engaged with lever arm 128 and in electrically communication with controller 150 via cable 152. As mentioned above, the electrosurgical energy delivered by electrical source 145 may comprise radiofrequency (RF) energy. As described in greater detail below, the electrodes of the jaw members may carry variable resistive positive temperature coefficient (PTC) bodies that are coupled to electrical source 145 and controller 150. Additional details regarding electrosurgical end effectors, jaw closing mechanisms, and electrosurgical energy-delivery surfaces are described in the following U.S. patents and published patent applications, all of which are incorporated herein in their entirety by reference and made a part of this specification: U.S. Pat. Nos. 7,381,209; 7,311,709; 7,220,951; 7,189,233; 7,186,253; 7,125,409; 7,112,201; 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,176; and U.S. Pat. App. Pub. Nos. 2010/0036370 and 2009/0076506.

Figure 3:
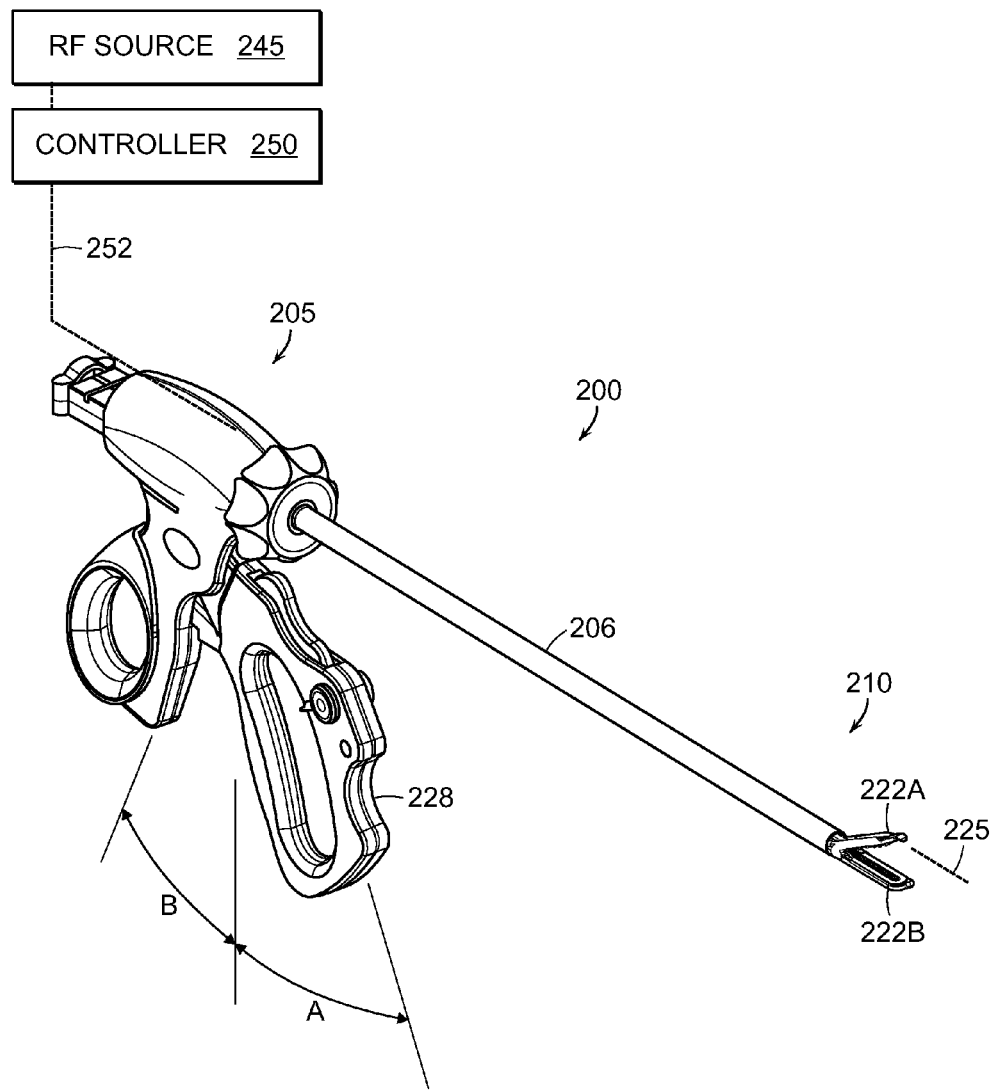
FIG. 3 is a perspective view of an electrosurgical instrument.
Figure 4A:
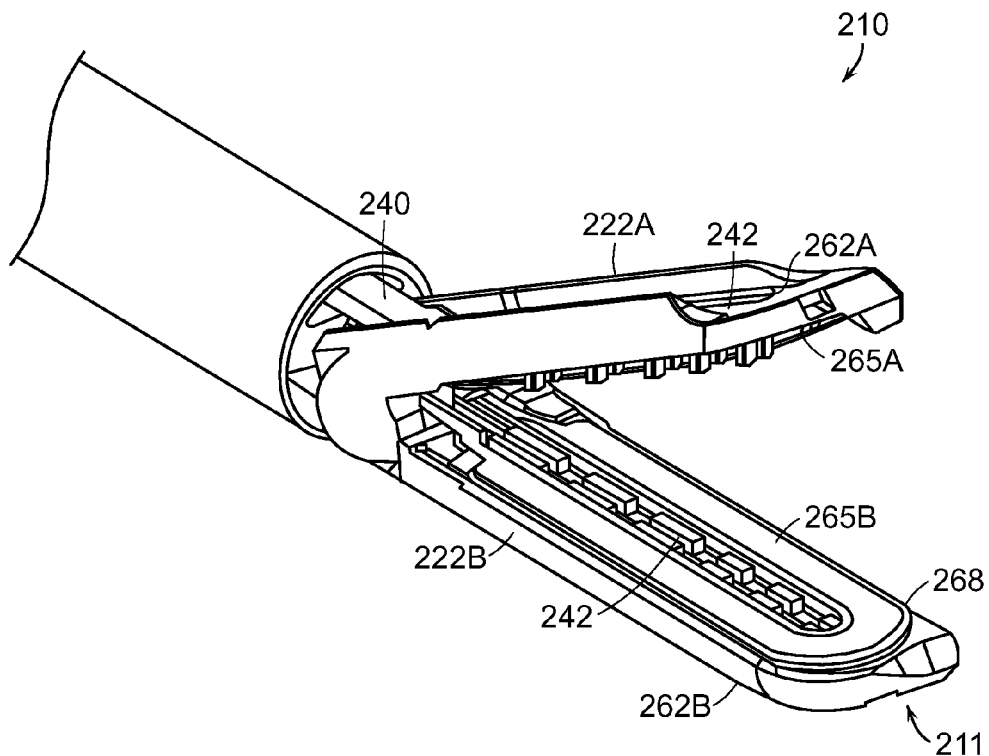
FIG. 4A illustrates an end effector of an electrosurgical instrument in an open configuration.
Figure 4B:
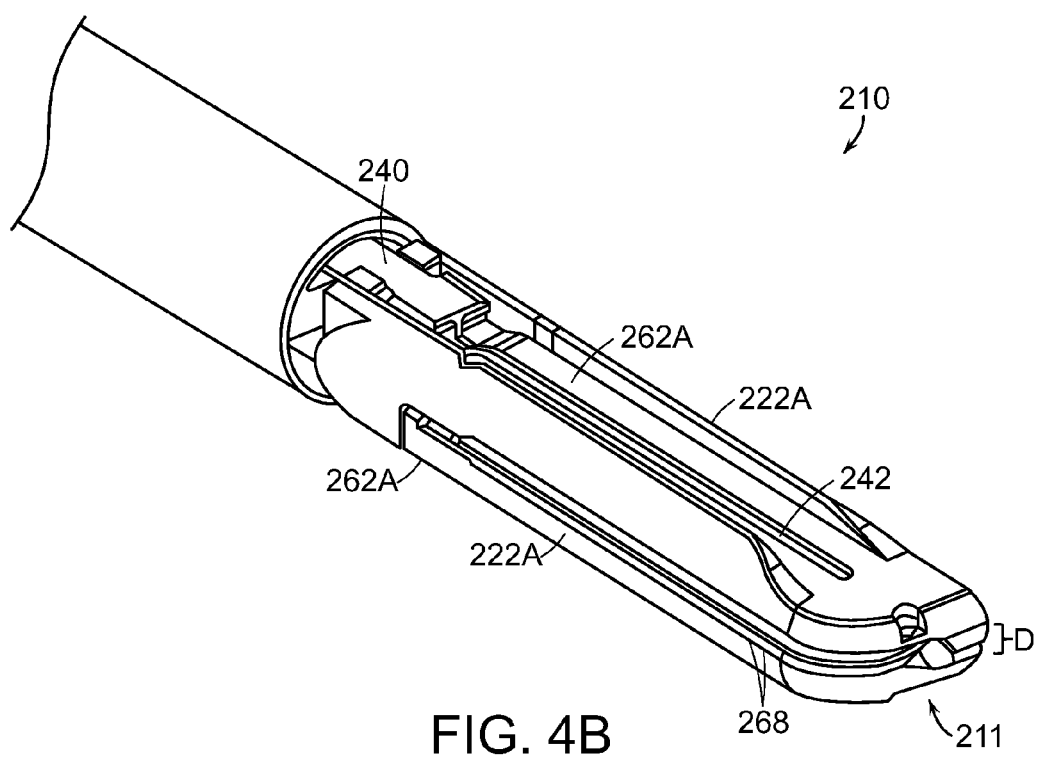
FIG. 4B illustrates the end effector of FIG. 4A in a closed configuration.

FIG. 3 illustrates an electrosurgical instrument 200 comprising a handle end 205, a shaft, or introducer, 206, and an end effector, or working end, 210. Shaft 206 can comprise any suitable cross-section, such as a cylindrical and/or rectangular cross-section, for example, and can comprise a tubular sleeve that extends from handle 205. End effector 210 can extend from shaft 206 and may be adapted for welding and transecting tissue. In various embodiments, end effector 210 can comprise an openable and closeable jaw assembly which can, in various embodiments, comprise straight, curved, and/or any other suitably configured jaws. In various embodiments, the end effector 210 can comprise a first jaw 222A and a second jaw 222B, wherein at least one of the jaws 222A and 222B can move relative to the other. In at least one embodiment, the first jaw 222A can be pivoted about an axis relative to the second jaw 222B in order close onto, capture, and/or engage tissue positioned between the jaws and apply a compression force or pressure thereto. In various embodiments, the handle 205 can comprise a lever arm, or trigger, 228 adapted to actuate a translatable member 240. More particularly, in at least one embodiment, the lever arm 228 can be actuated in order to move member 240 distally toward the distal end 211 of end effector 210 and, when member 240 is advanced distally, member 240 can contact first jaw 222A and move it downwardly toward second jaw 222B, as illustrated in FIG. 4B. In at least one embodiment, the translatable member 240 can comprise a proximal rack portion and the lever arm 228 can comprise a plurality of gear teeth which can be configured to drive the proximal rack portion of translatable member 240 distally. In certain embodiments, rotation of the lever arm 228 in the opposite direction can drive the translatable member 240 proximally.

Figure 4C:
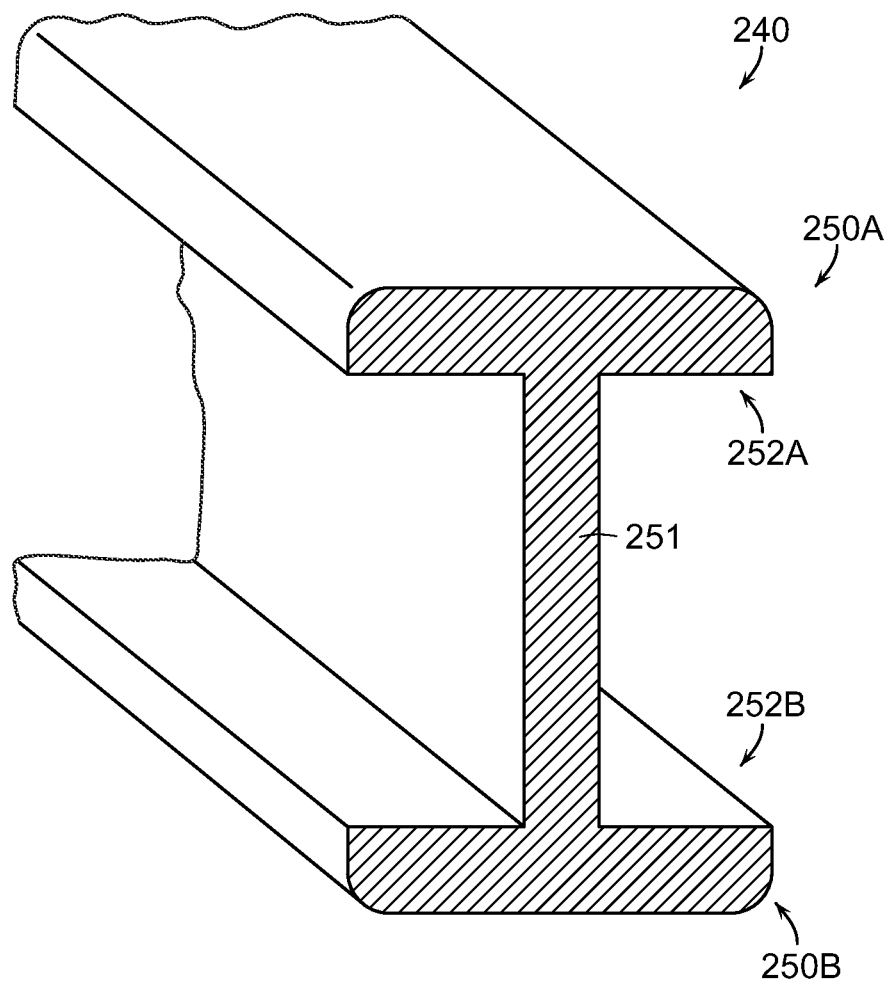
FIG. 4C is a sectional view of a translatable member shaped like an I-beam which is configured to close the end effector of the surgical instrument of FIG. 3.

As described above, the translatable member 240 can be configured to contact first jaw 222A and pivot jaw 222A toward second jaw 222B. In various embodiments, referring now to FIGS. 4A-4C, the distal end of reciprocating member 240 can comprise a flanged "I"-beam configured to slide within a channel 242 in the jaws 222A and 222B. Referring primarily to FIG. 4C, the I-beam portion of member 240 can comprise an upper flange 250A, a lower flange 250B, and a center, or intermediate, portion 251 connecting the flanges 250A and 250B. In at least one embodiment, the flanges 250A and 250B and the center portion 251 can define "c"-shaped channels on the opposite sides of member 240. In any event, in various embodiments, the flanges 250A and 250B can define inner cam surfaces 252A and 252B, respectively, for slidably engaging outward-facing surfaces 262A and 262B of jaws 222A and 222B, respectively. More particularly, the inner cam surface 252A can comprise a suitable profile configured to slidably engage the outer surface 262A of first jaw 222A and, similarly, the inner cam surface 252B can comprise a suitable profile configured to slidably engage the outer surface 262B of second jaw 222B such that, as translatable member 240 is advanced distally, the cam surfaces 252A and 252B can co-operate to cam first jaw member 222A toward second jaw member 222B and configure the end effector 240 in a closed configuration. As seen in FIG. 4B, jaws 222A and 222B can define a gap, or dimension, D between the first and second electrodes 265A and 265B of jaws 222A and 222B, respectively, when they are positioned in a closed configuration. In various embodiments, dimension D can equal a distance between approximately 0.0005" to approximately 0.005", for example, and, in at least one embodiment, between approximately 0.001" and approximately 0.002", for example.

As discussed above, the translatable member 240 can be at least partially advanced in order to move the first jaw 222A toward the second jaw 222B. Thereafter, the movable member 240 can be advanced further distally in order to transect the tissue positioned between the first jaw 222A and the second jaw 222B. In certain embodiments, the distal, or leading, end of the I-beam portion of 240 can comprise a sharp, or knife, edge which can be configured to incise the tissue. Before, during, and/or after the member 240 is advanced through the tissue, electrical current can be supplied to the electrodes in the first and second jaw members in order to weld the tissue, as described in greater detail further below. In various circumstances, the operation of the trigger 228 can advance the knife edge of the cutting member 240 to the very distal end of slot or channel 242. After the cutting member 240 has been sufficiently advanced, the trigger 288 can be released and moved into its original, or unactuated, position in order to retract the cutting member 240 and allow first jaw 222A to move into is open position again. In at least one such embodiment, the surgical instrument can comprise a jaw spring configured to bias the first jaw 222A into its open position and, in addition, a trigger spring configured to bias the trigger 228 into its unactuated position.

In various embodiments, further to the above, the surgical instrument can comprise a first conductor, such as an insulated wire, for example, which can be operably coupled with the first electrode 265A in first jaw member 222A and, in addition, a second conductor, such as an insulated wire, for example, which can be operably coupled with the second electrode 265B in second jaw member 222B. In at least one embodiment, referring again to FIG. 3, the first and second conductors can extend through shaft 206 between an electrical connector in handle 205 and the electrodes 265A and 265B in the end effector 210. In use, the first and second conductors can be operably coupled to electrical source 245 and controller 250 by electrical leads in cable 252 in order for the electrodes 265A and 265B to function as paired bi-polar electrodes with a positive polarity (+) and a negative polarity (−). More particularly, in at least one embodiment, one of the first and second electrodes 265A and 265B can be operably coupled with a positive (+) voltage terminal of electrical source 245 and the other of the first and second electrodes 265A and 265B can be electrically coupled with the negative voltage (−) terminal of electrical source 245. Owing to the opposite polarities of electrodes 265A and 265B, current can flow through the tissue positioned between the electrodes 265A and 265B and heat the tissue to a desired temperature. In certain embodiments, the cutting member 240 can act as an electrode when it is electrically coupled to a positive terminal or negative terminal of the source 245, and/or any suitable ground.

In various embodiments, referring now to FIG. 5, an end effector of a surgical instrument, such as end effector 310, for example, can comprise a first jaw 322A and a second jaw 322B, wherein at least one of the jaws 322A, 322B can be moved relative to the other in order to capture tissue therebetween. Each of the jaws 322A and 322B can comprise one or more electrodes which can be configured to permit current to flow between the electrodes and/or between an electrode and another portion of the end effector 310 when a voltage potential is applied to at least one of the electrodes. In at least one embodiment, current can flow between electrodes 381 and electrodes 380, for example. In certain embodiments, current can flow between the electrodes 381 and at least one of the frame member 328A of first jaw 322A, the frame member 328B of second jaw 322B, and/or the cutting member 340, for example. In at least one such embodiment, the electrodes 381 can be electrically coupled with the positive terminal of a power source while the electrodes 380, the frame members 328A, 328B, and/or the cutting member 140 can be electrically coupled with the negative terminal of the power source and/or any suitable ground. In certain embodiments, the surgical instrument can include a first conductor electrically coupled with the power source and the electrodes 380 and, in addition, a second conductor electrically coupled with the power source and the electrodes 381 such that a voltage potential can be applied to one or more of the electrodes 380 and 381 and a circuit can be completed therebetween. In any event, as described above, current flowing through the electrodes 381 and the tissue positioned intermediate the jaws 322A and 322B can generate heat and raise the temperature of the tissue and electrodes 381.

Figure 6:
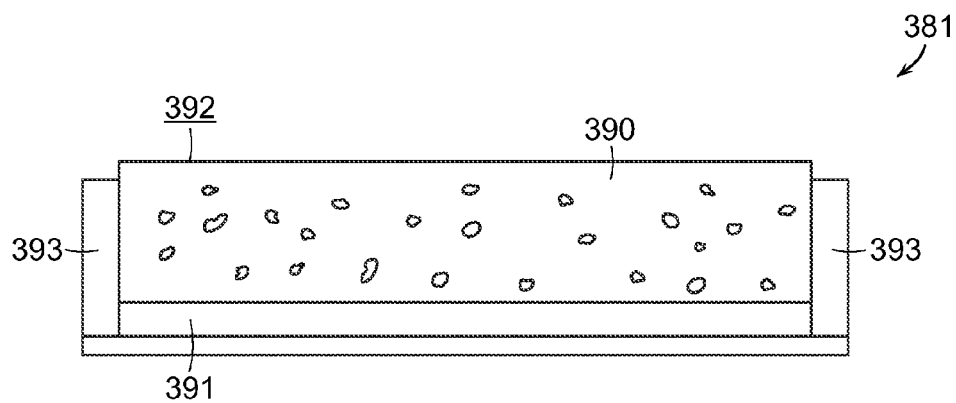
FIG. 6 is a cross-sectional view of a jaw of an end effector including an electrode comprising a porous material and an evaporable material stored within the porous material.

In various embodiments, one or more electrodes of the end effector 310, such as electrodes 381, for example, can comprise an evaporable material which can evaporate when the temperature of the electrodes 381 reach the boiling point of the evaporable material. In at least one such embodiment, referring to FIG. 6, an electrode 381 can comprise a porous material, or matrix, 390 and an evaporable material stored within the porous material 390. The porous material 390 can comprise an insulative, or relatively non-conductive material, such as, for example, elastomeric and thermoplastic polysaccharides, examples of which include cellulose acetate and cellulose nitrate, for example, fibrous hydrophilic textiles, open celled foams, examples of which include high internal phase emulsion (HIPE) foams including those disclosed in U.S. Pat. Nos. 5,563,179 and 5,387,207, the entire disclosures of which are incorporated by reference herein, thin-until-wet materials including those described in U.S. Pat. No. 5,108,383, the entire disclosure of which is incorporated by reference herein, porous glass frit materials, examples of which include silicon dioxide based glass mixes, and/or porous ceramic frit materials, such as ceramics comprising titanium dioxide, for example. The material, or materials, comprising porous material 390 can have a sufficient porosity in order to allow a conductive evaporable material to be absorbed into, or reside within, the pores of the porous material 390. In at least one embodiment, the conductive evaporable material can comprise saline, such as isotonic saline, for example. In various embodiments, the evaporable conductive material can comprise an electrical conductivity and/or a thermal conductivity which is the same order of magnitude, and/or within an order of magnitude, as the conductivities of the tissue, the porous material, and/or the opposing electrodes within the end effector, for example. In use, the conductive evaporable material can conduct current through the electrode 381 eventhough the porous material 390 may be non-conductive. Referring again to FIG. 6, an electrode 381 can comprise a conductive member 391 positioned on a first, or bottom, side of the porous material 390 and a conductive surface 392 positioned on a second, or top, side of the porous material 390. Further to the above, in various embodiments, a conductor can be electrically coupled to, one, a positive voltage terminal of a power source as described above, and, two, the conductive member 391 such that the conductor can apply a voltage potential to a first side of the electrode 381. In various circumstances, as a result, current can flow from the first conductive member 391, through the conductive evaporable material within the porous material 390, and through the conductive surface 392. When tissue is positioned against the conductive surface 392, the current can flow through the tissue into an opposing electrode 380, for example. Various alternative embodiments are envisioned in which the conductive member 391 is electrically coupled with a negative terminal of a power source and/or any suitable ground.

In various embodiments, further to the above, the conductive member 391 can be configured to attach the electrode 381 to the frame member 328B of second jaw 322B. In at least one embodiment, the conductive member 391 can comprise copper and/or brass which can be used to braze the electrode 381 to second jaw member 322B, while, in certain embodiments, the conductive member 391 can comprise a conductive adhesive, such as filled urethane acrylates, filled epoxies, and/or filled silicones, for example, which can adhere the electrode 381 to the jaw member 322B. In at least one embodiment, transfer tape, including 3M transfer tape which can be purchased from the Minnesota Mining and Manufacturing Company, can be utilized to adhere the electrode 381 to the jaw member 322B, for example. In some embodiments, fasteners, such as screws, for example, can be utilized to secure the electrode 381 to the frame member 328B. In certain embodiments, the electrode 381 can include sidewalls 393 which can be comprised of an electrically insulative material, such as silicon dioxide, for example. In at least one such embodiment, the sidewalls 393 can form a housing which can at least partially enclose the porous material 390. In various embodiments, the housing can comprise a first opening such that the conductive member 391 can be in contact with the first side of the porous material 390 and, in addition, a second opening such that tissue can contact conductive surface 392. In certain embodiments, the conductive surface 392 can comprise a tissue-contacting pad which can comprise a tissue-contacting surface configured to contact the tissue positioned intermediate the first jaw 322A and the second jaw 322B. In at least one such embodiment, the tissue-contacting pad can comprise a polymeric material having conductive particles dispersed therein, for example, wherein, in certain embodiments, the second conductive surface 392 can comprise a positive temperature coefficient (PTC) material as described below. In various embodiments, the frame portion of the jaw 322B surrounding the electrode 381 can be comprised of silicon, for example.

When a voltage potential is applied to electrode 381 and current flows therethrough, as described above, heat can be generated within the electrode 381 and the tissue positioned intermediate the jaws 322A and 322B. As the temperature of the electrode 381 increases, referring now to FIG. 8, the electrical resistance or impedance of the electrode 381 can also increase. Such an increase in temperature and resistance is represented by the portion of temperature-resistance curve in FIG. 8 between points X and Y. As the reader will note, the change in resistance of electrode 381 can be linearly proportional, or at least substantially linearly proportional, to the change in temperature of electrode 381, although other embodiments are envisioned in which this relationship is geometrically proportional. In at least one embodiment, the change in resistance can be incremental with respect to the change in temperature between points X and Y. In any event, once the temperature of the electrode 381 reaches the boiling point temperature Tb of the conductive evaporable material contained within the porous material 390, the evaporable material can evaporate. As the conductive evaporable material evaporates, the resistance of the electrode 381 can increase. More particularly, as the conductive material evaporates, fewer conductive, or electrically percolative, paths of the conductive evaporable material may exist in the porous material 390 thereby increasing the resistance of the electrode. In at least one embodiment, as discussed above, the porous material 390 can be comprised of a non-conductive, or at least substantially non-conductive, material such that, once the conductive material has evaporated, the electrical resistance of the electrode 381, which is substantially the electrical resistance of the porous material 390 at this point, may be sufficiently high so as to prevent, or at least substantially inhibit, current from flowing through the electrode 381.

Figure 8:
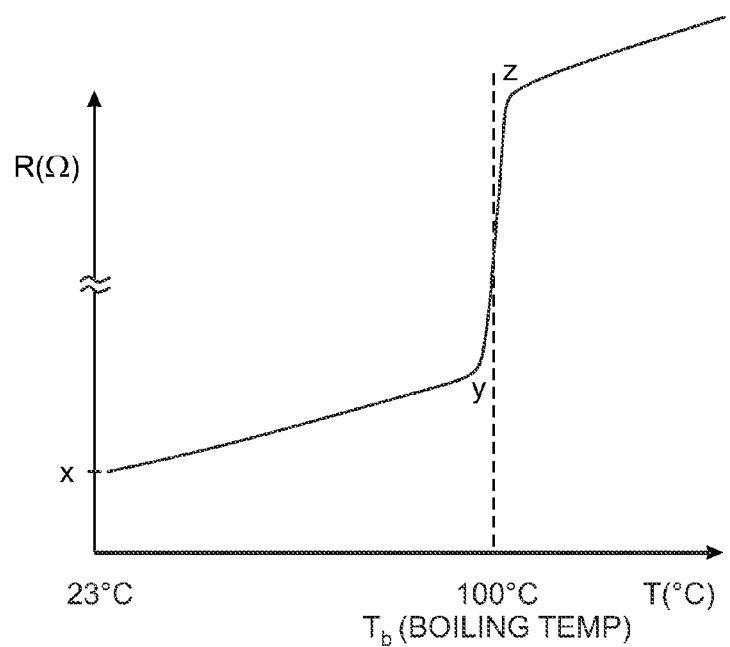
FIG. 8 is an exemplary temperature-resistance curve of an electrode comprising an evaporable material.

The transition of electrode 381 between being conductive and non-conductive, or at least substantially non-conductive, as described above, can be represented by the portion of the temperature-resistance curve between points Y and Z in FIG. 8. As the reader will note, the portion of the curve between points Y and Z depicted in FIG. 8 can be asymptotical, or at least substantially asymptotical, such that the slope of the temperature-resistance curve between points Y and Z is significantly higher than the slope of the curve between points X and Y. In various circumstances, the evaporation of the conductive material may take a period of time to occur and, during such time, the temperature of the electrode 381 may remain constant, or at least substantially constant, at the boiling point temperature Tb. In at least one embodiment, the conductive evaporable material can comprise a boiling point temperature of approximately 100 degrees Celsius, for example, at 1 atm atmospheric pressure. In various embodiments, the conductive evaporable material can comprise a boiling point temperature of approximately 105 degrees Celsius, approximately 110 degrees Celsius, approximately 115 degrees Celsius, or approximately 120 degrees Celsius, for example. In various circumstances, the boiling point of the conductive evaporable material can depend on the surrounding atmospheric pressure. In any event, in certain circumstances, the evaporation of the conductive material can begin to occur at certain locations, or hot spots, in the electrode 381 before the conductive material begins to evaporate at other locations within the electrode 381. In some such circumstances, the flow of current through electrode 381, and the tissue positioned thereagainst, can be reduced at the locations which have already reached the boiling point temperature of the conductive evaporable material, whereas the current can continue to flow through the portions of the electrode 381 which have not reached the boiling point temperature of the conductive evaporable material. In various embodiments, as a result, each electrode can comprise a means for an immediate and localized response to the heat being generated within the electrode and/or tissue positioned against the tissue. In certain circumstances, the top of porous material 390, or the portion of porous material 390 closest to surface 392, can reach the boiling point temperature of the conductive evaporable material before the bottom of the porous material 390, for example, reaches the boiling point temperature. In such circumstances, the evaporable material may evaporate, or at least substantially evaporate, from the top portion of the porous material 390 creating a short, or break, in the conductive paths between the conductive material 391 and the conductive surface 392 before the remainder of the electrode 381 reaches the boiling point temperature. In any event, once the conductive evaporable material has evaporated, or at least substantially evaporated, from the porous material 390, and/or once the resistance of the electrode 381 has increased between a first resistance (Point Y) and a substantially higher resistance (Point Z), the resistance of the electrode 381 can increase incrementally as the temperature of the electrode 381 increases.

In various embodiments, further to the above, the boiling point temperature Tb of the conductive evaporable material can comprise a switching temperature of the electrode 381 in which, as discussed above, the resistance of the electrode 381 can increase significantly. In certain embodiments, the electrical resistance of the electrode can increase between a first resistance (Point Y), for example, to a second resistance (Point Z), for example. In at least one embodiment, the first resistance (Point Y) can be approximately 5 ohms, approximately 10 ohms, approximately 15 ohms, approximately 20 ohms, approximately 25 ohms, approximately 30 ohms and/or within a range between approximately 5 ohms and approximately 30 ohms, for example. In at least one embodiment, the second resistance (Point Z) can be approximately 140 ohms, approximately 145 ohms, approximately 150 ohms, approximately 155 ohms, approximately 160 ohms and/or within a range between approximately 140 ohms and approximately 160 ohms, for example. In certain embodiments, the second resistance (Point Z) can be approximately 450 ohms, for example. In various circumstances, the second, or switched, resistance can be significantly higher than the first resistance such that current flowing through the electrode 381, if any current flows at all, may not be able to irreversibly alter and/or therapeutically treat the tissue positioned between the first and second jaws 322A, 322B. In certain embodiments, the switched, second electrical resistance can be approximately 2, 5, 10, 100, or 1000 times larger than the first, unswitched, resistance. In various circumstances, as described above, the conductive evaporable material can transition between a liquid and a vapor wherein the vapor can outgas from the porous material into the environment surrounding the end effector 310. In certain embodiments, the heat created within the electrode 381 can cause the conductive evaporative material to migrate out of the porous material 390 thereby increasing the electrical resistance of the electrode 381. In at least one such embodiment, a temperature differential created within the electrode 381 can cause the conductive evaporable material to migrate away, or possibly toward, the higher temperature within the electrode 381. In certain circumstances, the conductive evaporable material can flow, withdraw, and/or recede from the porous material 390 at certain temperatures of the electrode 381.

In various circumstances, the electrodes 381 can cool below, be cooled below, and/or be permitted to cool below the boiling point temperature of the conductive evaporable material. In at least some circumstances, the evaporated conductive material can recondense and can be reabsorbed by the porous material 390. In certain circumstances, however, at least a large portion of the evaporated material may be unrecoverable. In at least one such circumstance, the porous material 390 can be configured to absorb blood and/or other surrounding conductive fluids, for example, from the surgical site once the temperature of the electrodes 381 drops below the boiling point temperature of such fluids. In at least one embodiment, a supply of electrolytic fluid can be supplied to the surgical site and/or end effector 310 such that the electrodes 381 have a ready supply of conductive fluids to replenish the evaporated fluids. Such a surgical instrument can comprise a pump and/or a reservoir which can be configured to supply an evaporable liquid to the electrodes 381 via one or more supply conduits extending through and/or along the shaft of the surgical instrument. In any event, the newly absorbed conductive material can allow current to be conducted through the electrodes 381 and, as a result, allow the electrodes 381 to be used to treat tissue once again. In certain embodiments, each electrode 381 can comprise a sealed, or an at least substantially sealed, housing wherein the porous material 390 and the conductive evaporable material can be contained therein. In at least one such embodiment, the conductive evaporable material can be in a liquid state within the porous material 390 when the temperature of the electrode is below the boiling point temperature of the conductive evaporable material and, in the event that the conductive evaporable material were to leak or flow out of the porous material 390, the conductive evaporable material could be contained within the sealed housing. As the temperature of the electrode is increased during use, the conductive evaporable material can evaporate into a vapor; however, the evaporated material can be contained, or at least substantially contained, within the sealed housing such that, when the temperature of the electrode cools below the boiling point temperature of the conductive evaporable material, the conductive evaporated material can recondense and can be reabsorbed by the porous material. In at least one embodiment, the entirety of the conductive evaporable material can be recovered and reabsorbed by the porous material, although other embodiments are envisioned in which a substantial portion, or only a portion, of the conductive evaporable material can be recovered and reabsorbed.

In various embodiments, a surgical instrument can comprise an end effector which can be detached from the surgical instrument and replaced with another end effector, wherein such end effectors can comprise electrodes having at least one porous material and conductive evaporable material such as those disclosed throughout this application. In at least one embodiment, an initial end effector can be attached to the shaft of the surgical instrument and, after the end effector has been used and at least a portion of the evaporable material has been evaporated therefrom, the surgical instrument can be removed from the patient and the initial end effector can be detached from the surgical instrument. Thereafter, another end effector can be attached to the surgical instrument, wherein the surgical instrument can then be reinserted into the surgical site and used once again. In at least one such embodiment, the electrodes of the end effector can have a full supply of evaporable material which can allow the surgical instrument to be used once again as described herein.

In various embodiments, an electrode can comprise more than one porous material and/or more than one conductive evaporable material. In at least one such embodiment, a first conductive evaporable material and a second conductive evaporable material can be stored within a porous material, wherein the first and second evaporable materials can have different boiling point temperatures, for example. During use, in at least one such embodiment, the temperature of the electrode can increase until it reaches the first boiling point temperature wherein, at such a temperature, the first conductive evaporable material can evaporate. In various embodiments, the second boiling point temperature of the second conductive evaporable material can be higher than the first boiling point temperature such that the second conductive evaporable material can remain unevaporated within the porous material eventhough the temperature of the electrode may have reached and/or exceeded the first boiling point temperature. In various circumstances, the evaporation of the first conductive evaporable material can cause the electrical resistance of the electrode to increase between a first resistance and a second resistance. Owing to the presence of the second conductive evaporable material within the porous material, however, the second electrical resistance of the electrode can be such that sufficient current can be conducted through the electrode in order to sufficiently treat the tissue. Once the temperature of the electrode reaches the second boiling point temperature, however, the second conductive material can evaporate and the electrical resistance of the electrode can increase to a third electrical resistance which makes the electrode non-conductive, or at least substantially non-conductive. In various embodiments, further to the above, the first and second conductive evaporable materials can have different electrical conductivities. In at least one embodiment, for example, the first conductive evaporable material can comprise a first electrical conductivity which is higher than the second conductive evaporable material. In at least one such embodiment, the evaporation of the first conductive material before the evaporation of the second conductive material can leave the electrode with a conductive material having a lesser electrical conductivity thereby resulting in a higher resistance of the electrode. In certain embodiments, the conductive material having a higher boiling point temperature can have a higher electrical conductivity than the electrical conductivity of the material having a lower boiling point temperature.

In various embodiments, the porous material, or matrix, of the electrodes disclosed in the present application may be sufficiently mechanically robust in order to withstand the clamping pressure of the jaws. In addition, such electrodes may be mechanically and/or chemically stable to withstand at least 140 degrees Celsius in a steam atmosphere. Furthermore, the porous material may be able to rapidly absorb liquid moisture and/or rapidly desorb vapor. In various embodiments, rapid absorption and desorption of the conductive evaporable material can be enhanced via chemistry. For example, the surface tension on the surfaces of the pores can be modified via functionalization of polymer chains comprising the porous material. In at least one such circumstance, the surface of the polymer can be treated with a plasma processing technique in order to create functional groups within the surface of the polymer material. In certain embodiments, the surface of the porous material can be treated via radiation functionalization. In various embodiments, the surface of the porous material can be coated with surfactants, for example.

Figure 7:
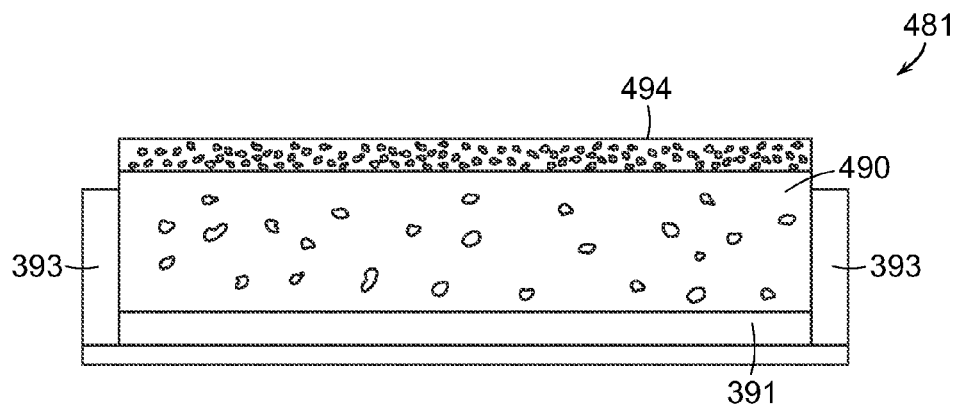
FIG. 7 is a cross-sectional view of a jaw of an end effector including an electrode comprising two layers of porous material and an evaporable material stored within the layers of porous material.

In various embodiments, the porous material, or matrix, of the electrodes disclosed in the present application may comprise one or more salts therein. In at least one such embodiment, the salts can be mixed into the porous material, such as a polymer material, for example, before the mixture is formed into an electrode, such as by an injection molding process, for example. In any event, such salts can pull fluids into the matrix via osmotic gradients, for example. In certain embodiments, referring now to FIG. 7, an electrode, such as electrode 481, for example, can comprise a first porous material, or base layer, 490 and a second porous material, or top layer, 494, wherein the top layer 494 can be positioned against the tissue to be treated. In at least one embodiment, the base layer 490 can comprise a high salt content which can pull fluid into the base layer 490 through the top layer 494. The base layer 490 can hydrate the top layer 494 and act as a reservoir to supply the top layer 494 as and/or after the evaporable material is depleted from the top layer 494. In various embodiments, the top layer 494 can be thinner than the base layer 490 wherein, in at least one embodiment, the thicker base layer 490 can be sufficiently rigid to support the thinner top layer 494. In use, the thinner top layer 494 can be designed to be rapidly depleted of its water content, for example, and decrease its effective electrical conductivity as the temperature of the top layer 494 exceeds the phase transition temperature of the water, which can be approximately 100 degrees Celsius in a multitude of circumstances, for example. In various embodiments, the top layer 494 can be comprised of polyamide foam, such as Monodur, for example, and/or porous polytetrafluoroethylene (PTFE), for example. The base layer 490 can be comprised of glass frit and/or woven cellulose, for example, and the osmotic generating salts can be comprised of potassium chloride (KCl), sodium sulphate (Na2SO4), ammonium dihydrogen phosphate (NH4)H2PO4, and/or a calcium chloride such as CaCl2-2H2O, for example.

Referring again to FIG. 5, electrodes 381 can be mounted to second jaw 322B which is positioned opposite the first jaw 322A. In various embodiments, the first jaw 322a can be comprised of silicon, the entirety of which, or at least substantial entirety of which, can comprise a return, or negative, electrode. In various embodiments, referring now to FIG. 10, a surgical instrument can comprise an electrode, such as electrode 581, for example, which can comprise a top surface, or pad, which can be positioned opposite the first jaw 322A. In at least one embodiment, the electrode 581 can comprise a tissue-contacting pad 592 which can be electrically coupled to the positive terminal of a power source via electrical conductors, or leads, 595, for example. In use, as described above, the tissue-contacting pad 592 can be polarized by the power source in order to treat the tissue positioned thereagainst. In various embodiments, the pad 592 can be mounted to electrode 581 on electrically insulative members 593 which can be comprised of silicon dioxide, for example. The insulative members 593 can comprise part of an electrode frame also comprising insulative members 595, for example. In certain embodiments, the electrode 581 can further comprise a connective layer 591 which can be used to mount the electrode 581 to second jaw 322B, for example. In at least one such embodiment, the connective layer 591 can comprise braze and/or adhesive, for example. In certain embodiments, ceramic inserts can be positioned between the electrodes 581 and the frame of the second jaw member, for example.

Figure 11:
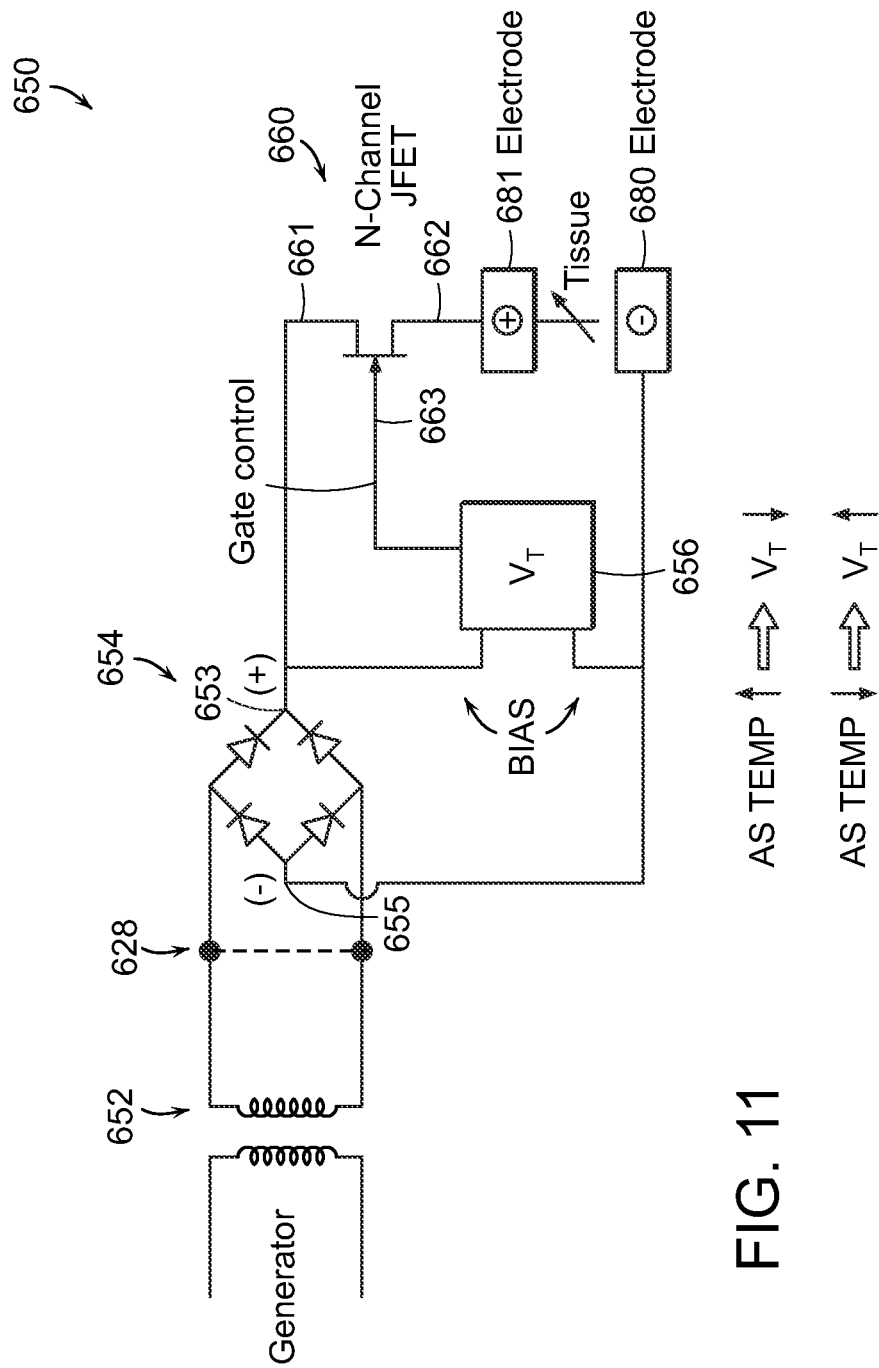
FIG. 11 is a schematic of an electrical circuit configured to control the voltage potential applied to the electrodes of an end effector.
Figure 12:
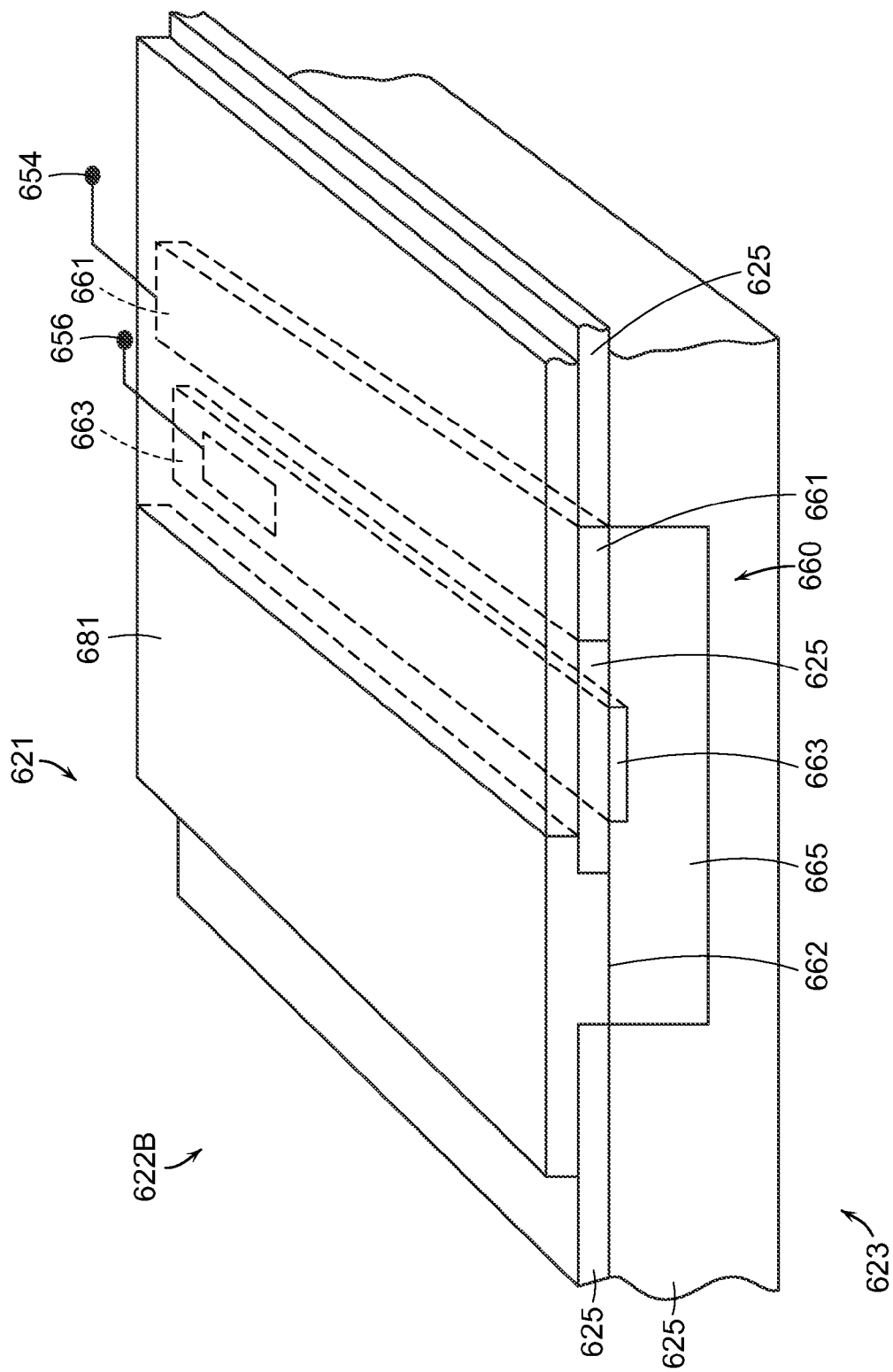
FIG. 12 is a diagram of an electrode that can be used in conjunction with the electrical circuit of FIG. 11.

In various embodiments, referring now to FIGS. 11 and 12, a surgical instrument can comprise an integrated JFET to control the current flowing through the electrode 581, and/or any other suitable electrode. An exemplary schematic of an electrical circuit 650 is provided in FIG. 11 which can be utilized in connection with an electrosurgical instrument, including the electrosurgical instruments disclosed herein, wherein the electrical circuit 650 can be configured to sense the temperature of the end effector jaws, the electrodes 680, 681, and/or the tissue positioned intermediate the electrodes 680, 681, and modulate the voltage applied to, and the current flowing through, the electrodes 680, 681 in view of the sensed temperature. Owing to the modulated current flowing through the electrodes 680, 681, the heat generated by the current can be modulated. More particularly, as described in greater detail below, the electrical circuit 650 can be configured to decrease the magnitude of current flowing between the electrodes 680, 681 and, as a result, reduce the heat generated by such current. Correspondingly, as also described in greater detail below, the electrical circuit 650 can be configured to increase the magnitude of the current flowing between the electrodes 680, 681 and, as a result, permit the heat generated by such current to increase.

Further to the above, the electrical circuit 650 can comprise a power supply and/or the secondary wiring of a transformer 652 powered by a generator, for example, which can be configured to apply a voltage potential to diode bridge 654. More particularly, in at least one embodiment, the surgical instrument can further comprise a trigger, and/or trigger switch 628, which can be configured to close one or more contacts and electrically couple the transformer 652 to the diode bridge 654. Diode bridge 654, as is well known in the art, can be configured to rectify the input voltage supplied to the electrical circuit 650 by the generator. In at least one such embodiment, the diode bridge 654 can be configured to rectify an alternating sinusoidal voltage wherein, although not illustrated, the circuit 650 can further comprise one or more capacitive elements which can smooth ripples within the rectified voltage, for example. In any event, the diode bridge 654 can comprise a rectified positive voltage terminal 653 and a rectified negative voltage terminal 655. Electrically coupled in parallel to the positive terminal 653 and the negative terminal 655 is a temperature sensing circuit 656 which can detect the temperature of the electrode 681 and/or the jaw supporting electrode 681, for example. Various temperature sensing circuits that can provide temperature sensing circuit 656 are disclosed in U.S. Pat. No. 3,703,651, entitled TEMPERATURE-CONTROLLED INTEGRATED CIRCUITS, which issued on Nov. 21, 1972, and U.S. Pat. No. 6,789,939, entitled TEMPERATURE SENSOR AND METHOD FOR OPERATING A TEMPERATURE SENSOR, which issued on Sep. 14, 2004, the entire disclosures of which are incorporated by reference herein. Various other temperature sensing circuits are commercially available from National Semiconductor Corporation, Santa Clara, Calif.

In various embodiments, further to the above, the electrical circuit 650 can further comprise a junction gate field-effect transistor (JFET) 660 which can be controlled by the temperature sensing circuit 656. More particularly, the JFET 660 can comprise a source terminal 661 electrically coupled to the positive terminal 653 of the diode bridge 654, a drain terminal 662 electrically coupled to the electrode 681, and, in addition, a gate terminal 663 which can be in electrical communication with the temperature sensing circuit 656, wherein the electrical resistance, or impedance, between the source terminal 661 and the drain terminal 662 can be controlled by the voltage potential applied to the gate terminal 663 by the temperature sensing circuit 656. In at least one such embodiment, the JFET 660 can include a channel comprised of an n-type semiconductor material, for example, wherein current can flow through the channel between the source terminal 661 and the drain terminal 662, and wherein the gate terminal 663 can be positioned relative to the channel such that an electric field produced by the gate terminal 663 can affect the flow of current through the channel. More particularly, when the gate terminal 663 is polarized, or the polarization of the gate terminal 663 is changed, the gate terminal 663 can produce an electric field which can, at least temporarily, affect the semiconductor material such that the resistance between the source terminal 661 and the drain terminal 662 is affected. In certain embodiments, an increase in the voltage potential applied to gate terminal 663 can increase the electrical resistance while, in other embodiments, an increase in the voltage potential applied to gate terminal 663 can decrease the electrical resistance, for example. In any event, when the resistance between the source terminal 661 and the drain terminal 662 is increased, the current flowing between the source terminal 661 and the drain terminal 662 can be decreased.

In operation, in at least one embodiment, the temperature sensing circuit 665 can be configured to apply a voltage potential to the gate terminal 663 of JFET 660 which is a function of the temperature sensed by the temperature sensing circuit 665. The temperature sensing circuit 665 can be configured to apply a first voltage potential to the gate terminal 663 when it detects a first temperature, a second voltage potential when it detects a second temperature, and a third voltage potential when it detects a third temperature, and so forth. In various embodiments, the temperature sensing circuit 665 can decrease the voltage potential applied to the gate terminal 663 as the temperature of the electrode 681 increases. For example, the temperature sensing circuit 665 can be configured to apply a first voltage potential to the gate terminal 663 when a first temperature is detected by the temperature sensing circuit and, in addition, a second voltage potential, which is lower than the first voltage potential, when the temperature sensing circuit 665 detects a second temperature which is higher than the first temperature. Correspondingly, the temperature sensing circuit 665 can increase the voltage potential applied to the gate terminal 663 as the temperature of the electrode 681 decreases. In such embodiments, the resistance, or impedance, of the JFET 660 channel can increase when the temperature of the electrode 681 increases, thereby 'constricting' the current that can flow therethrough, and decrease when the temperature of the electrode 681 decreases, thereby "relaxing' the constriction of the current flowing through the channel. In various alternative embodiments, the JFET can be configured such that an increase in voltage potential applied to the gate of the JFET increases the resistance of the JFET channel while a decrease in voltage potential applied to the gate of the JFET decreases the resistance of the JFET channel. In certain embodiments, the channel of JFET 660 can comprise a p-type semiconductor material.

In various circumstances, further to the above, the magnitude of the current flowing through the channel of JFET 660 (drain-source current) can be a function of, one, the voltage differential between the source terminal 661 and the drain terminal 662 (drain-source voltage) and, two, the voltage of the gate terminal 663 as discussed above. In various embodiments, the drain-source current can be directly proportional to the drain-source voltage and/or the gate voltage. In certain circumstances, the relationship between the drain-source current and the drain-source voltage can comprise at least two operating regions for certain values of the drain-source voltage and the gate voltage, for example. More particularly, the operating curve of a JFET device can comprise what are known as a linear region and a saturation region, wherein the relationship between the drain-source current and the drain-source voltage is different in each of these regions. In various embodiments, the relationship between the drain-source current and the gate voltage in the saturation region of the JFET operating curve can be linearly, or at least substantially linearly, proportional, for example.

In various embodiments, referring now to FIG. 12, an end effector of a surgical instrument can comprise a jaw 622*b* which can include the electrode 681 and the JFET 660, for example. In at least one such embodiment, the source terminal 661 can comprise an elongate conductor extending longitudinally from the proximal end 621 of the jaw 622B to the distal end 623 of jaw 622B. As outlined above, the source terminal 661 can be electrically coupled to the rectified positive voltage terminal 653 of diode bridge 654 via a conductor, or lead, extending therebetween, for example. Similarly, the gate terminal 663 can comprise an elongate member which also extends from the proximal end 621 to the distal end 623 of jaw 622B, for example, wherein the gate terminal 663 can be electrically coupled to an output of the temperature sensing circuit 656 via a conductor, or lead, extending between the gate terminal 663 and the temperature sensing circuit 656, for example. In various embodiments, further to the above, the JFET 660 can include a channel, such as channel 665, for example, which can be comprised of at least one semiconductor material, for example. In at least one such embodiment, the source terminal 661 and the drain terminal 662 of the JFET 660 can be positioned on opposite sides of the gate terminal 663, wherein the electrode 681 can be positioned against, and/or otherwise in electrical communication with, the drain terminal 662. Similar to the above, the electrode 681 can extend longitudinally along the drain terminal 662 from the proximal end 621 to the distal end 623 of the jaw 622B, for example. As discussed above, the gate terminal 663 can be polarized to create, or change, an electric field, within the channel 665 in order to alter the flow of current through the channel 665 between the source terminal 661 and the drain terminal 662. In various embodiments, further to the above, the jaw 622A can comprise one or more insulative members 625, for example, which can be configured to electrically insulate the source terminal 661 from the drain terminal 662 such that the current flows through the channel 665. Although not illustrated, in various embodiments, the diode bridge 654 can be positioned in the handle, the shaft, and/or the end effector of the surgical instrument, although larger diodes may be suitably accommodated in the handle of the surgical instrument, for example.

Figure 13:
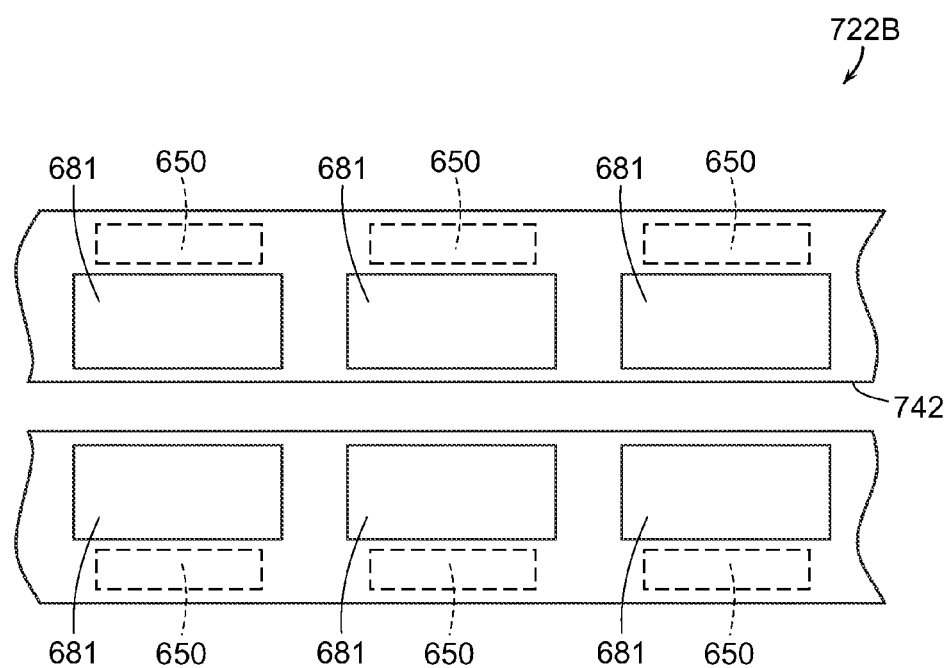
FIG. 13 is a diagram of a jaw of an end effector comprising a plurality of electrodes controlled by a plurality of electrical circuits.

In various embodiments, the jaw 622B can comprise a first electrode 681 positioned along a first side of a channel configured to receive a cutting member and, in addition, a second electrode 681 positioned along a second side of the cutting member channel. In at least one embodiment, each of the electrodes 681 can be operably coupled with a circuit 650 which can be configured to independently monitor the temperature of the electrodes 681 and independently adjust the current flowing through the electrodes 681. In at least one such embodiment, the current flowing through, and the heat generated by, the entire length of each electrode 681 can be adjusted simultaneously. In various embodiments, referring now to FIG. 13, a jaw 722B, for example, can comprise a plurality of electrodes 681 positioned on a first side of a cutting member channel 742 and a plurality of electrodes 681 positioned on a second side of a cutting member channel 742. In at least one such embodiment, each of the electrodes 681 can be operably coupled with a control circuit 650, wherein each control circuit 650 can be configured to independently monitor and control the temperature of their respective electrodes 681. In various circumstances, as a result, the current flowing through, and the heat generated by, each electrode 681 can be adjusted independently of one another.

As described above, various embodiments can utilize integrated JFET devices for controlling the current flowing through the electrodes of an electrosurgical device. In certain embodiments, any other suitable field effect transistors and/or bipolar transistors could be utilized. In at least one such embodiment, a control circuit can comprise a temperature sensing circuit, such as temperature sensing circuit 656, for example, and a bipolar junction transistor, wherein the bipolar junction transistor can comprise an emitter terminal, a collector terminal, and a base terminal, and wherein the temperature sensing circuit is operably coupled with the base terminal such that the temperature sensor can apply a voltage potential to the base terminal and affect the flow of current between the emitter terminal and the collector terminal, for example.

Figure 14:
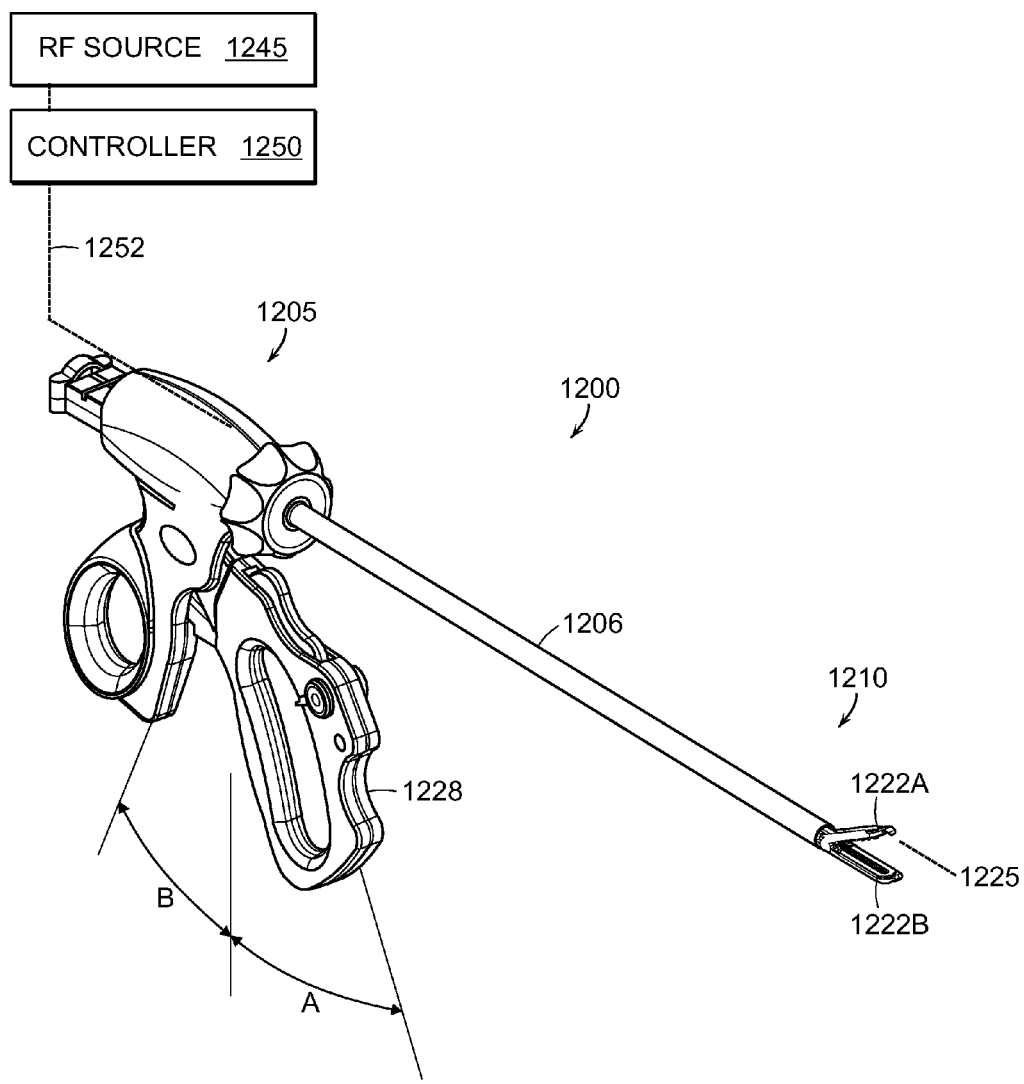
FIG. 14 is a perspective view of an electrosurgical device.

FIG. 14 illustrates an electrosurgical instrument 1200 comprising a handle end 1205, a shaft, or introducer, 1206, and an end effector, or working end, 1210. Shaft 1206 can comprise any suitable cross-section, such as a cylindrical and/or rectangular cross-section, for example, and can comprise a tubular sleeve that extends from handle 1205. End effector 1210 can extend from shaft 1206 and may be adapted for welding and transecting tissue. In various embodiments, end effector 1210 can comprise an openable and closeable jaw assembly which can, in various embodiments, comprise straight, curved, and/or any other suitably configured jaws. In various embodiments, the end effector 1210 can comprise a first jaw 1222A and a second jaw 1222B, wherein at least one of the jaws 1222A and 1222B can move relative to the other. In at least one embodiment, the first jaw 1222A can be pivoted about an axis relative to the second jaw 1222B in order close onto, capture, and/or engage tissue positioned between the jaws and apply a compression force or pressure thereto. In various embodiments, the handle 1205 can comprise a lever arm 1228 adapted to actuate a translatable member 1240. More particularly, in at least one embodiment, the lever arm 1228 can be actuated in order to move member 1240 distally toward the distal end 1211 of end effector 1210 and, when member 1240 is advanced distally, member 1240 can contact first jaw 1222A and move it downwardly toward second jaw 1222B, as illustrated in FIG. 15B. In at least one embodiment, the translatable member 1240 can comprise a proximal rack portion and the lever arm 1228 can comprise a plurality of gear teeth which can be configured to drive the proximal rack portion of translatable member 1240 distally. In certain embodiments, rotation of the lever arm 1228 in the opposite direction can drive the translatable member 1240 proximally.

As described above, the translatable member 1240 can be configured to contact first jaw 1222A and pivot jaw 1222A toward second jaw 1222B. In various embodiments, referring now to FIGS. 15A-15C, the distal end of reciprocating member 1240 can comprise a flanged "I"-beam configured to slide within a channel 1242 in the jaws 1222A and 1222B. Referring primarily to FIG. 15C, the I-beam portion of member 1240 can comprise an upper flange 1250A, a lower flange 1250B, and a center, or intermediate, portion 1251 connecting the flanges 1250A and 1250B. In at least one embodiment, the flanges 1250A and 1250B and the center portion 1251 can define "c"-shaped channels on the opposite sides of member 1240. In any event, in various embodiments, the flanges 1250A and 1250B can define inner cam surfaces 1252A and 1252B, respectively, for slidably engaging outward-facing surfaces 1262A and 1262B of jaws 1222a and 1222B, respectively. More particularly, the inner cam surface 1252A can comprise a suitable profile configured to slidably engage the outer surface 1262A of first jaw 1222A and, similarly, the inner cam surface 1252B can comprise a suitable profile configured to slidably engage the outer surface 1262B of second jaw 1222b such that, as translatable member 1240 is advanced distally, the cam surfaces 1252A and 1252B can co-operate to cam first jaw member 1222A toward second jaw member 1222B and configure the end effector 1240 in a closed configuration. As seen in FIG. 15B, jaws 1222A and 1222B can define a gap, or dimension, D between the first and second electrodes 1265A and 1265B of jaws 1222A and 1222B, respectively, when they are positioned in a closed configuration. In various embodiments, dimension D can equal a distance between approximately 0.0005" to approximately 0.005", for example, and, in at least one embodiment, between approximately 0.001" and approximately 0.002", for example.

In various embodiments, further to the above, the surgical instrument can comprise a first conductor, such as an insulated wire, for example, which can be operably coupled with the first electrode 1265A in first jaw member 1222A and, in addition, the surgical instrument can further comprise a second conductor, such as an insulated wire, for example, which can be operably coupled with the second electrode 1265B in second jaw member 1222B. In at least one embodiment, referring again to FIG. 14, the first and second conductors can extend through shaft 1206 between an electrical connector in handle 1205 and the electrodes 1265A and 1265B in the end effector 1210. In use, the first and second conductors can be operably coupled to electrical source 1245 and controller 1250 by electrical leads in cable 1252 in order for the electrodes 1265A and 1265B to function as paired bi-polar electrodes with a positive polarity (+) and a negative polarity (−). More particularly, in at least one embodiment, one of the first and second electrodes 1265A and 1265B can be operably coupled with a positive (+) voltage terminal of electrical source 1245 and the other of the first and second electrodes 1265A and 1265B can be electrically coupled with the negative voltage (−) terminal of electrical source 1245. Owing to the opposite polarities of electrodes 1265A and 1265B, current can flow through the tissue positioned between the electrodes 1265A and 1265B and heat the tissue to a desired temperature.

The surgical instrument 1200, and the system comprising electrical source 1245 and controller 1250, for example, may be configured to provide different electrosurgical energy-delivery operating modes which, in certain embodiments, may depend on the amount, or degree, of jaw closure. In any event, in various circumstances, further to the above, the degree of jaw closure may be represented by the degree of actuation of lever 1228 such as, for example, degrees of actuation A and B illustrated in FIG. 14. Alternatively, the degree of actuation may be represented by the axial translation of reciprocating member 1240. In various circumstances, it may be useful to switch between different electrosurgical energy-delivery operating modes depending on the volume of tissue captured within the end effector of the surgical instrument and the amount of compression applied to the tissue. For example, the instrument 1200 may deliver Rf energy in a first operating mode to large volumes of the captured tissue in order to cause an initial dehydration of the tissue, wherein the surgical instrument 1200 may thereafter switch, and/or be switched by controller 1250, for example, to a second operating mode which allows for more effective tissue welding. In various circumstances, this second operating mode may provide a greater amount or a lesser amount of energy to the tissue and/or adjust the manner or location in which the energy is being supplied to the tissue. Alternatively, when engaging a lesser volume of tissue, for example, the surgical instrument 1200 and/or accompanying system may deliver Rf energy in only one operating mode which can be best suited for tissue welding, for example.

Figure 15A:
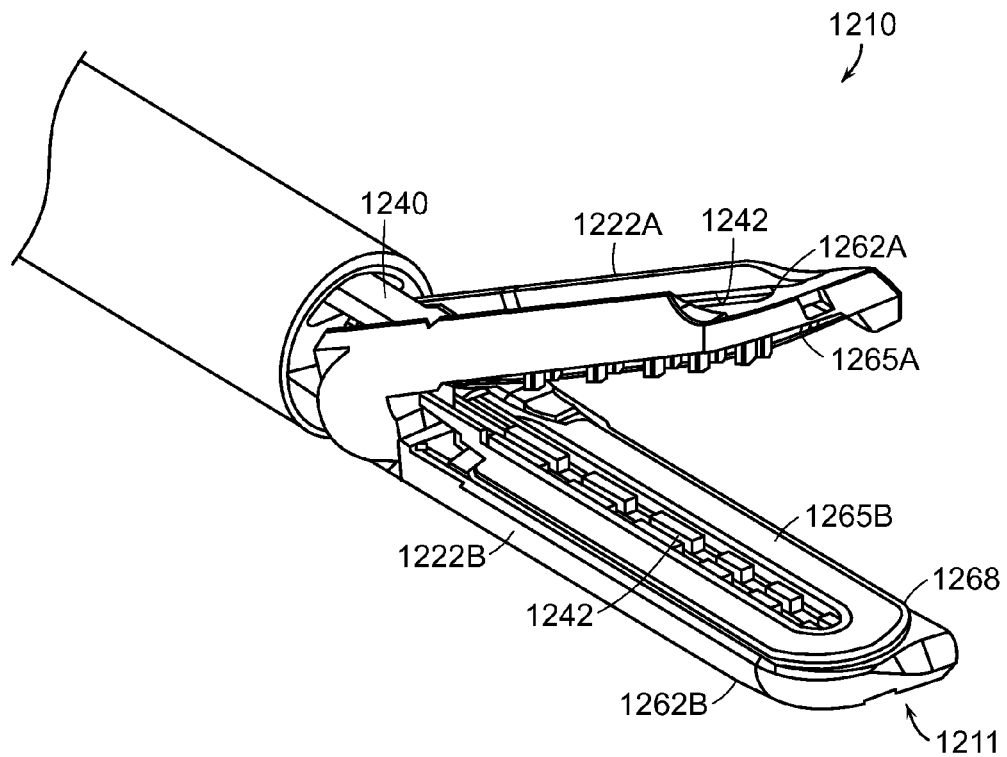
FIG. 15A illustrates an end effector of an electrosurgical instrument in an open configuration.
Figure 15B:
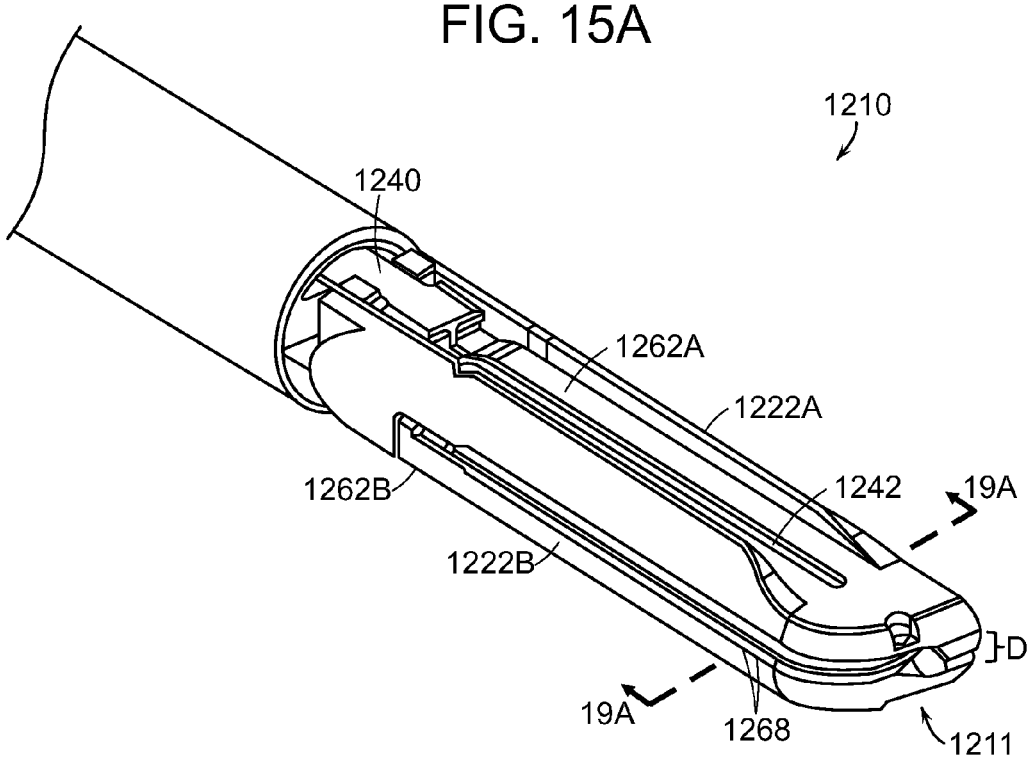
FIG. 15B illustrates the end effector of FIG. 15A in a closed configuration.
Figure 15C:
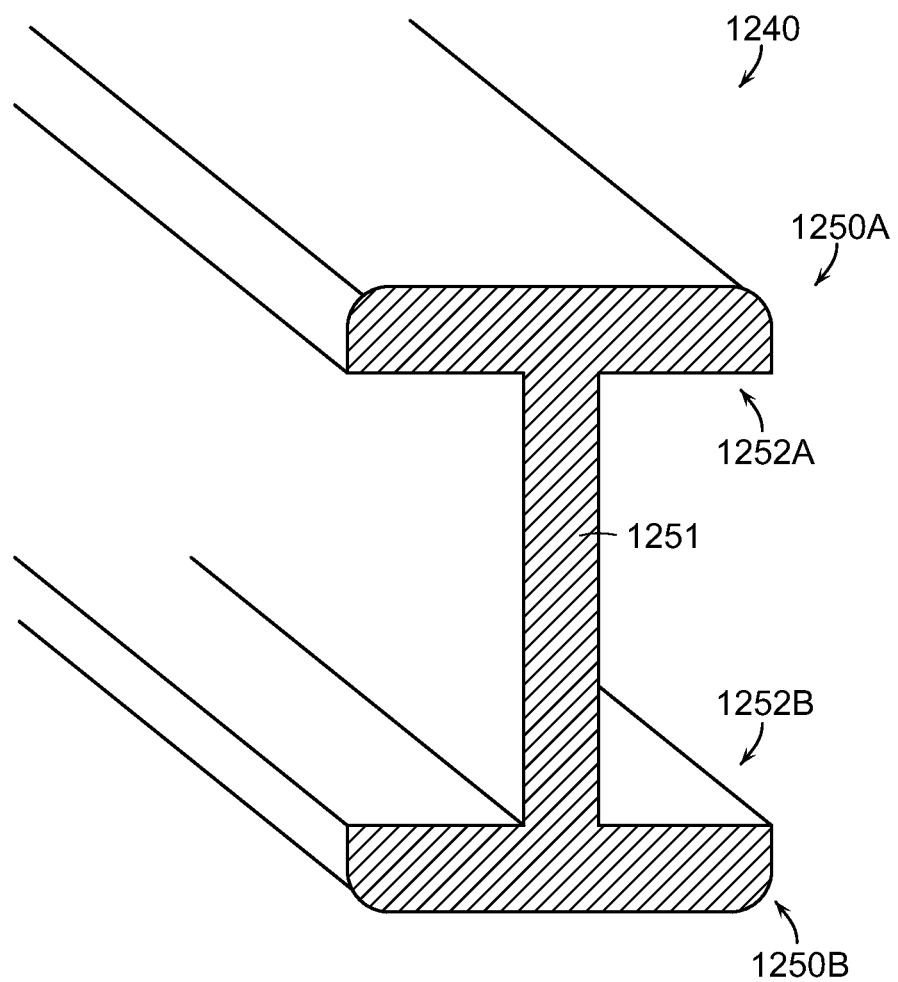
FIG. 15C is a sectional view of a translatable member shaped like an I-beam which is configured to close the end effector of the surgical instrument of FIG. 14.
Figure 16A:
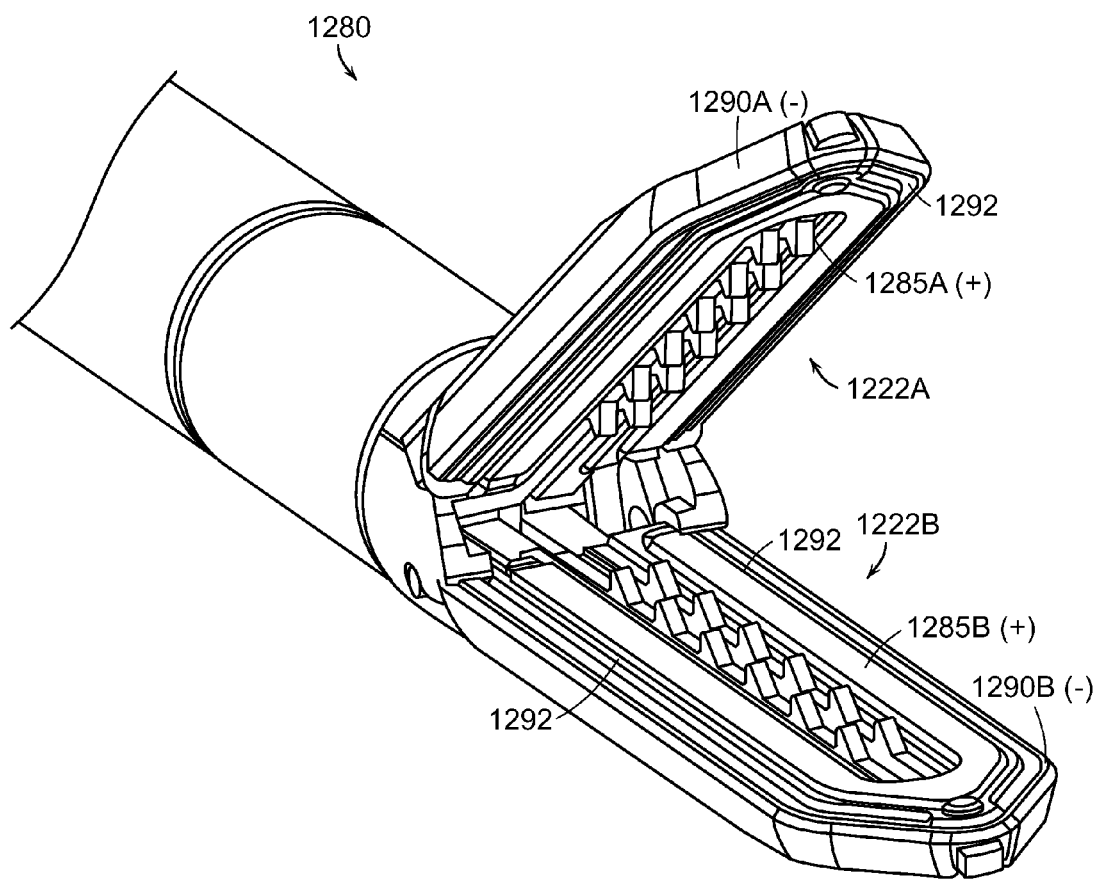
FIGS. 16A-16B illustrate an end effector of another electrosurgical instrument in a fully open position.
Figure 16B:
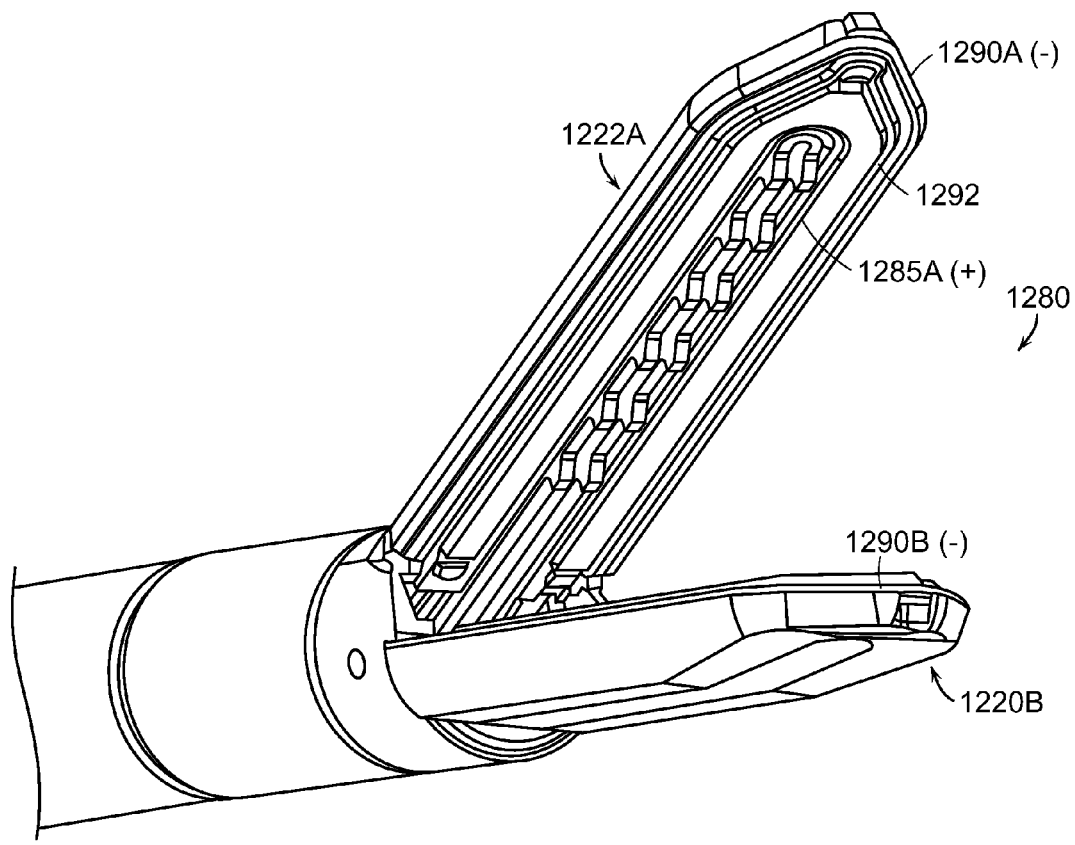

FIGS. 16A and 16B illustrate views of an alternative embodiment of an end effector, i.e., end effector 1280, which can be similar in many respects to the end effector 1210 shown in FIGS. 15A-15B. Similar to the above, the end effector 1280 can comprise first and second conductive bodies, or electrodes, 1285A and 1285B in the respective first and second jaws 1222A and 1222B. In addition, the end effector 1280 can further comprise additional conductive bodies, such as third and fourth electrodes 1290A and 1290B, for example, which can be positioned around the perimeters of electrodes 1285A and 1285B, respectively. In at least one embodiment, the electrodes 1290A and 1290B can be structural, perimeter components of the respective jaws 1222A and 1222B. In certain embodiments, the third electrode 1290A can surround the perimeter of first electrode 1285A and, similarly, the fourth electrode 1290B can surround the perimeter of second electrode 1285B. In at least one such embodiment, the paired arrangement of electrodes 1285A and 1290A can be a minor-image to the paired arrangement of electrodes 1285B and 1290B. In various embodiments, the jaw member 1222A can further comprise at least one intermediate material 1292 positioned intermediate the first and third electrodes 1285A and 1290A in the first jaw 1222A. Similarly, the second jaw member 1222B can further comprise an intermediate material 1292 positioned intermediate to the second and fourth electrodes 1285B and 1290B in the second jaw 1222B. The intermediate material 1292 may be at least one of an insulator, a positive temperature coefficient of resistance (PTC) material, and/or a fixed resistive material, for example.

Similar to the above, the surgical instrument can comprise a plurality of conductors which can operably couple the positive and negative terminals of current source 1245 with the electrodes 1285A, 1285B, 1290A, and 1290B. For example, in at least one embodiment, the surgical instrument can comprise a first conductor electrically coupled with the first electrode 1285A, a second conductor electrically coupled with the second electrode 1285B, a third conductor electrically coupled with the third electrode 1290A, and a fourth conductor electrically coupled with the fourth electrode 1290B, wherein the first, second, third, and fourth conductors can be selectively coupled with the positive and/or negative terminals of electrical source 1245, for example. More particularly, the surgical instrument can be operated in various modes of operation in which one or more of the electrodes 1285A, 1285B, 1290A, and 1290B, via their respective conductors, are electrically coupled with the positive (+) terminal of the electrical source 1245 and one or more of the electrodes 1285A, 1285B, 1290A, and 1290B, via their respective conductors, are electrically coupled with the negative (−) terminal of the electrical source 1245. In various circumstances, referring to FIGS. 16A-19C, the first, second, third, and fourth electrodes 1285A, 1285B, 1290A and 1290B are indicated in various modes of operation as having polarities indicated as a positive polarity (+), a negative polarity (−), or an absence of polarity (Ø). In some embodiments, the translatable member 1240 can carry electrical current or, alternatively, the translatable member 1240 can be coated with an insulator layer to prevent the member 1240 from functioning as a conductive path for the current.

Figure 17:
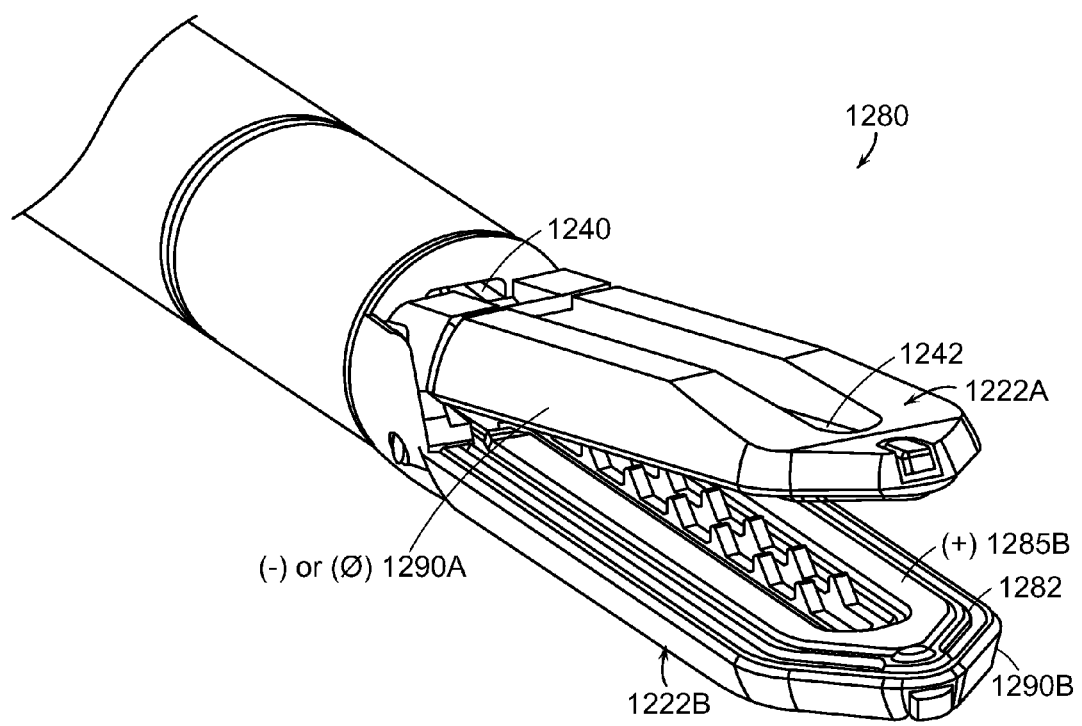
FIG. 17 illustrates the end effector of FIGS. 16A-16B in an intermediate, or partially closed, position.
Figure 18:
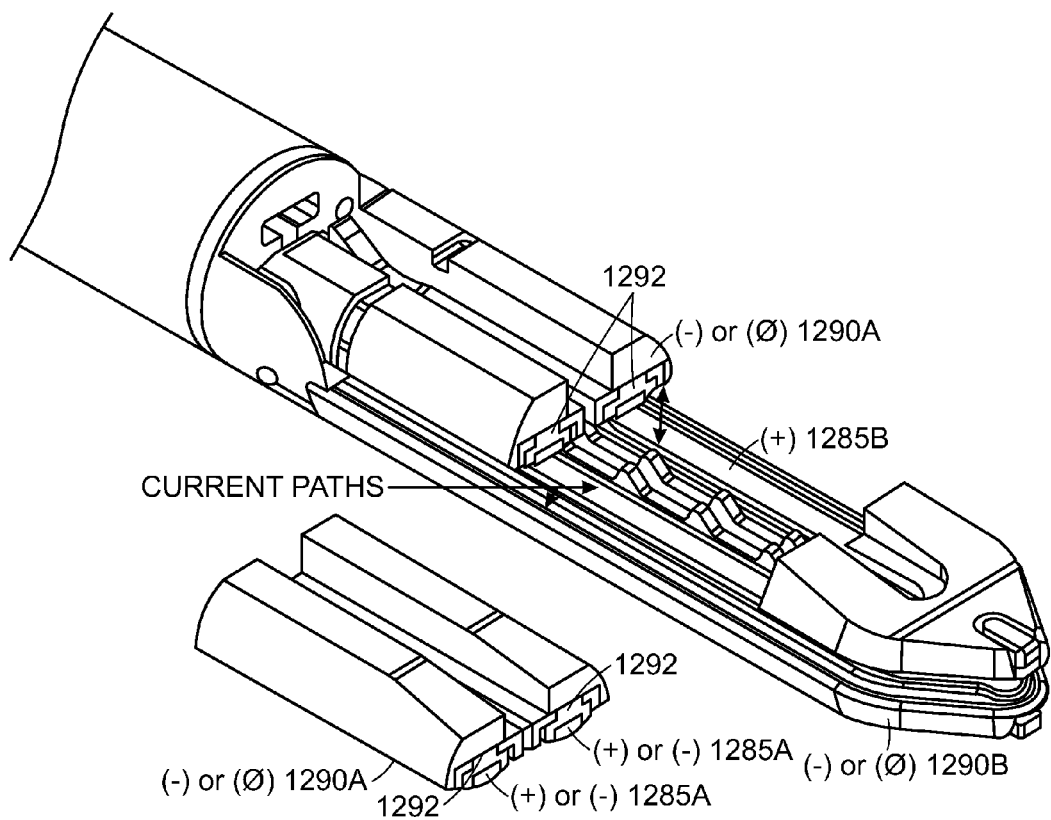
FIG. 18 is an exploded view of the end effector of FIGS. 16A-16B in a fully closed position.
Figure 19A:
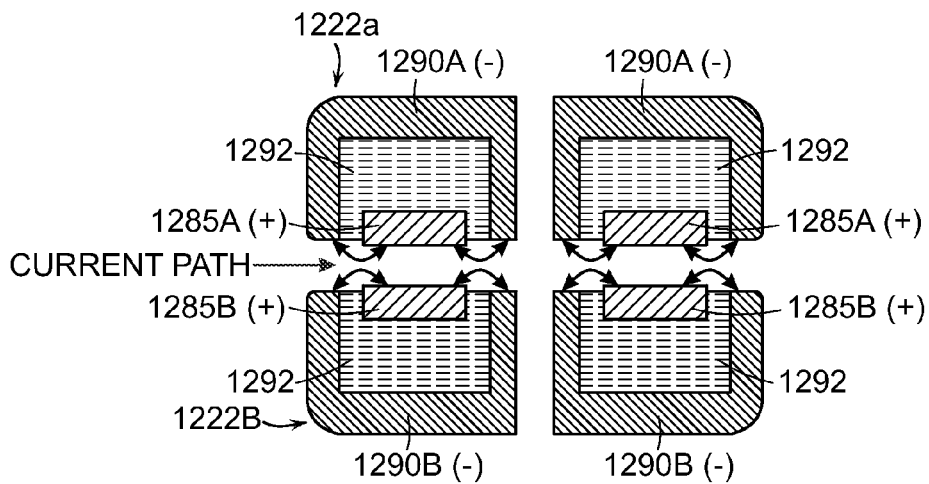
FIGS. 19A-19C are sectional views of the end effector of FIGS. 16A-16B in different modes of operation.
Figure 19B:
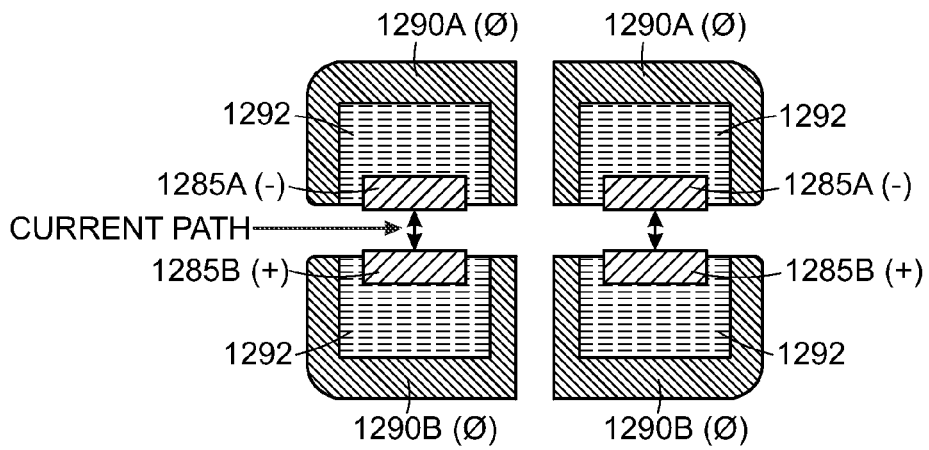
Figure 19C:
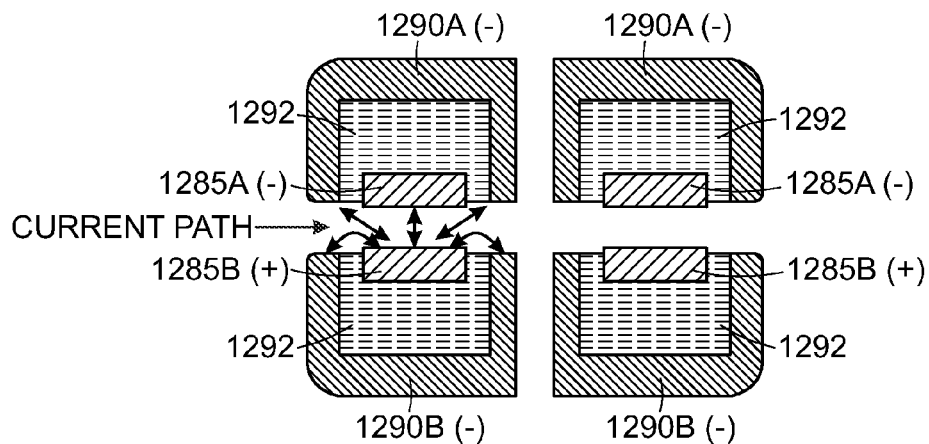

In various embodiments, further to the above, the polarity of the electrodes 1285A, 1285B, 1290A, and/or 1290B can be switched depending on the degree of jaw closure. In at least one operating mode, electrodes within the same jaw can comprise different polarities. For example, as can be seen in FIGS. 16A, 16B, and 19A, the polarities of the electrodes can be such that current can flow between electrodes 1285A (+) and 1290A (−) in the first jaw 1222A and, similarly, between electrodes 1285B (+) and 1290B (−) in the second jaw 1222B. In various circumstances, this operating mode may be well-suited for sealing or welding thin or highly compressed tissues volumes. In at least one operating mode, the electrodes which are positioned opposite each other can have different polarities. For example, as can be seen in FIG. 19B, the interior electrodes 1285A (−) and 1285B (+) are switched to have opposing polarities for providing Rf current paths through the tissue positioned between the jaws 1222A and 1222B in order to cause dehydration of thick tissue volumes, for example. The second and fourth electrodes 1290A and 1290B may also have opposite polarities or, alternatively, they may have a null polarity or an absence of polarity (Ø), as illustrated in FIG. 19B, for example. In various circumstances, further to the above, the operational mode of FIG. 19B may be useful when the jaws are moved from a fully open position, or 0% jaw closure (FIGS. 16A-16B), into an intermediate closure configuration in order to at least partially dehydrate the tissue. Once in the intermediate closure configuration, as illustrated in FIG. 17, the surgical instrument may switch into the operational mode of FIG. 19A which may provide a more optimal energy delivery configuration for creating a high-strength seal or weld in the engaged tissue.

In various embodiments, further to the above, a control system and/or controller 1250 can switch the surgical instrument from one operating mode to another mode after the jaw has been closed a predetermined amount, wherein, in at least one embodiment the switchover can occur at 10%, 20%, 30%, 40%, 50%, 60%, 70%, and/or 80% of the jaw closure, for example. In certain embodiments, the surgical instrument can comprise a sensor configured to detect the degree to which first jaw 1222A has been closed. In various embodiments, the switching between electrosurgical modes can be triggered by one or more operational parameters, such as (i) the degree of jaw closure as described above, (ii) the impedance of the engaged tissue, and/or (iii) the rate of change of impedance or any combination thereof. Furthermore, the polarity of the electrodes can be switched more than two times during the operation of the surgical instrument. Other operating modes are disclosed in U.S. patent application Ser. No. 12/050,462, entitled ELECTROSURGICAL INSTRUMENT AND METHOD, filed on Mar. 18, 2008, the entire disclosure of which is incorporated by reference herein.

As discussed above, the translatable member 1240 can be at least partially advanced in order to move the first jaw 1222A toward the second jaw 1222B. Thereafter, the movable member 1240 can be advanced further distally in order to transect the tissue positioned between the first jaw 1222A and the second jaw 1222B. In certain embodiments, the distal, or leading, end of the I-beam portion of 1240 can comprise a sharp, or knife, edge which can be configured to incise the tissue. As the member 1240 is advanced through the tissue, the electrical current can be supplied to the electrodes of the first and second jaw members as described above. In certain embodiments, as described above, the cutting member 1240 can act as an electrode when it is electrically coupled to a positive terminal or negative terminal of the source 1245, and/or any suitable ground. In various circumstances, the operation of the trigger 1228 can advance the knife edge of the cutting member 1240 to the very distal end of slot or channel 1242. After the cutting member 1240 has been sufficiently advanced, the trigger 1288 can be released and moved into its original, or unactuated, position in order to retract the cutting member 1240 and allow first jaw 1222A to move into is open position again. In at least one such embodiment, the surgical instrument can comprise a jaw spring configured to bias the first jaw 1222A into its open position and, in addition, a trigger spring configured to bias the trigger 1288 into its unactuated position.

In various embodiments, as described above, current can flow from one electrode to another while passing through the tissue captured by the end effector of the surgical instrument. As also described above, the current passing through the tissue can heat the tissue. In various circumstances, however, the tissue may become overheated. In order to avoid such overheating, the electrodes of various surgical instruments can comprise materials which may no longer conduct current, or may conduct at least substantially less current, when the electrode materials have reached or exceeded a certain temperature. Stated another way, in at least one embodiment, the electrical resistance of the electrode material can increase with the temperature of the material and, in certain embodiments, the electrical resistance of the material can increase significantly when the material has reached or exceeded a certain transition, or switching, temperature. In various circumstances, such materials can be referred to as positive temperature coefficient, or PTC, materials. In at least some such PTC materials, the PTC material can be comprised of a first non-conductive material, or substrate, which has a high electrical resistance and, in addition, a second, conductive material, or particles, having a lower electrical resistance interdispersed throughout the substrate material. In at least one embodiment, the substrate material can comprise polyethylene and/or high-density polyethylene (HDPE), for example, and the conductive material can comprise carbon particles, for example. In any event, when the temperature of the PTC material is below its transition temperature, the conductive material can be present in the non-conductive material in a sufficient volumetric density such that the current can flow through the PTC material via the conductive particles. When the temperature of the PTC material has exceeded its transition temperature, the substrate, or non-conductive material may have sufficiently expanded and/or changed states such that the conductive particles are no longer sufficiently in contact with one another in order provide a sufficient path for the current to flow therethrough. Stated another way, the expansion and/or state change of the substrate material may cause the volumetric density of the conductive particles to fall below a sufficient volumetric density in order for current to be conducted therethrough, or at least substantially conducted therethrough. In various circumstances, as a result of the above, the PTC material may act as a circuit breaker which can prevent, or at least inhibit, additional energy from reaching the tissue being treated, that is, at least until the PTC material has cooled sufficiently and reached a temperature which is below the transition, or switching, temperature. At such point, the PTC material could begin to conduct current again.

Further to the above, describing a material as having a positive temperature coefficient of resistance (PTC) can mean that the resistance of the material increases as the temperature of the material increases. Many metal-like materials exhibit electrical conduction that has a slight positive temperature coefficient of resistance. In such metal-like materials, the PTC's variable resistance effect is characterized by a gradual increase in resistance that is linearly proportional to temperature—that is, a linear PTC effect. A "nonlinear" PTC effect can be exhibited by certain types of polymer matrices, or substrates, that are doped with conductive particles. These polymer PTC compositions can comprise a base polymer that undergoes a phase change or can comprise a glass transition temperature Tg such that the PTC composition has a resistance that increases sharply over a narrow temperature range (see FIG. 9).

Polymeric PTC material can consist of a crystalline or semi-crystalline polymer (e.g., polyethylene) that carries a dispersed filler of conductive particles, such as carbon powder or nickel particles, for example, therein. In use, a polymeric PTC material can exhibit temperature-induced changes in the base polymer in order to alter the electrical resistance of the polymer-particle composite. In a low temperature state, the crystalline structure of the base polymer can cause dense packing of the conductive particles (i.e., carbon) into its crystalline boundaries so that the particles are in close proximity and allow current to flow through the PTC material via these carbon "chains". When the PTC material is at a low temperature, numerous carbon chains form the conductive paths through the material. When the PTC material is heated to a selected level, or an over-current causes $I^2R$ heating (Joule heating) within the PTC material, the polymer base material may be elevated in temperature until it exceeds a phase transformation temperature. As the polymer passes through this phase transformation temperature, the crystalline structure can change to an amorphous state. The amorphous state can cause the conductive particles to move apart from each other until the carbon chains are disrupted and can no longer conduct current. Thus, the resistance of the PTC material increases sharply. In general, the temperature at which the base polymer transitions to its amorphous state and affects conductivity is called its switching temperature Ts. In at least one embodiment, the transition or switching temperature Ts can be approximately 120 degrees Celsius, for example. In any event, as long as the base polymer of the PTC material stays above its switching temperature Ts, whether from external heating or from an overcurrent, the high resistance state will remain. Reversing the phase transformation allows the conductive particle chains to reform as the polymer re-crystallizes to thereby restore multiple current paths, and a low resistance, through the PTC material. Conductive polymer PTC compositions and their use are disclosed in U.S. Pat. Nos. 4,237,441; 4,304,987; 4,545,926; 4,849,133; 4,910,389; 5,106,538; and 5,880,668, the entire disclosures of which are incorporated by reference herein.

As discussed above, in many embodiments, the conductive polymer PTC composition may comprise a base polymer, or substrate, and conductive elements dispersed in the base polymer. When describing properties of the base polymer of a PTC composition, it may be useful to further explain the terms glass transition temperature Tg and melting temperature Tm. A glass transition temperature Tg of a material may not be the same as a melting temperature Tm. A transition at Tm occurs in crystalline polymers when the polymer chains fall out of their crystalline phase, and become a disordered deformable or flowable media. A glass transition at Tg is a transition which occurs in amorphous polymers (i.e., polymers whose chains are not arranged in ordered crystals). A glass transition temperature (Tg) in a crystalline polymer may be defined as a temperature point where the polymer experiences a significant change in properties—such as a large change in Young's modulus (also known as modulus of elasticity), for example. In such circumstances, the Tg can comprise the temperature at which the polymer structure turns "rubbery" upon heating and "glassy" upon cooling. Crystalline polymers may also go through a stage of becoming leathery before becoming rubbery. There is a loss of stiffness (e.g., decreased modulus of elasticity) in both of these stages. Such crystalline polymers, or domains thereof, can comprise a sharp, defined melting point Tm. In contrast, an amorphous polymer can be structural below the glass transition temperature Tg and transition from being stiff to flowable (at its melting temperature Tm) over a wide temperature range.

The temperature-induced variable resistance of a polymer PTC composition when used in a current-limiting application can be based on an overall energy balance—and can be described by Equation (1) below. It may now be useful to describe the basic thermal/resistance properties of a PTC device comprising a polymeric PTC composition to explain how (i) highly non-linear PTC effects and (ii) rapid switching may be achieved in the PTC materials described herein.

$$m * Cp(\Delta T/\Delta t) = I^2 * R - U*(T-Ta) \quad \text{Equation (1), wherein:}$$

m=mass of the PTC composition
Cp=specific heat capacity of the PTC composition (at a constant pressure)
ΔT=change in temperature of the PTC composition
Δt=change in time
I=current flowing through the PTC composition
R=resistance of the PTC composition
U=overall heat-transfer coefficient
T=temperature of the PTC composition
Ta=ambient temperature In equation (1) above, the current flowing through the PTC composition generates heat at a rate equal to $I^2R$. All or some of this heat can be subtracted by interaction with the environment at a rate described by the term U*(T−Ta), depending on how the device or composition is configured for interaction with the environment. This portion of equation (1), i.e., U*(T−Ta), accounts for losses due to one or more of convection, conduction, and radiation heat transfers. Any heat not subtracted by environmental interaction raises the temperature of the PTC composition/device at a rate described by the term: m*Cp*(ΔT/Δt)—Equation (2). The reader will note that Equation (2) assumes that there is a uniform temperature across the polymeric PTC composition. In circumstances where this is not true, this portion of the equation can be adapted in order to account for such particularities. In any event, if the heat generated by the polymeric PTC composition and the heat subtracted to the operating environment are in balance, T/t goes to zero, and Equation (1) can be rewritten as: $I^2*R-U*(T-Ta)$—Equation (3). In various circumstances, under certain operating conditions, the heat generated within the PTC material and the heat lost by the PTC material to the environment can be in balance at a relatively low temperature such as, for example, Point A shown in FIG. 9. If the current flow (I) through the PTC composition increases and the ambient temperature remains constant, the heat generated by the PTC composition increases and, correspondingly, the temperature of the PTC composition also increases. In the event, however, that the increase in current is not too large and all the generated heat can be lost to the environment, the temperature and resistance of the PTC material may stabilize according to Equation (3) at a higher temperature, such as Point B in FIG. 9, for example.

Figure 9:
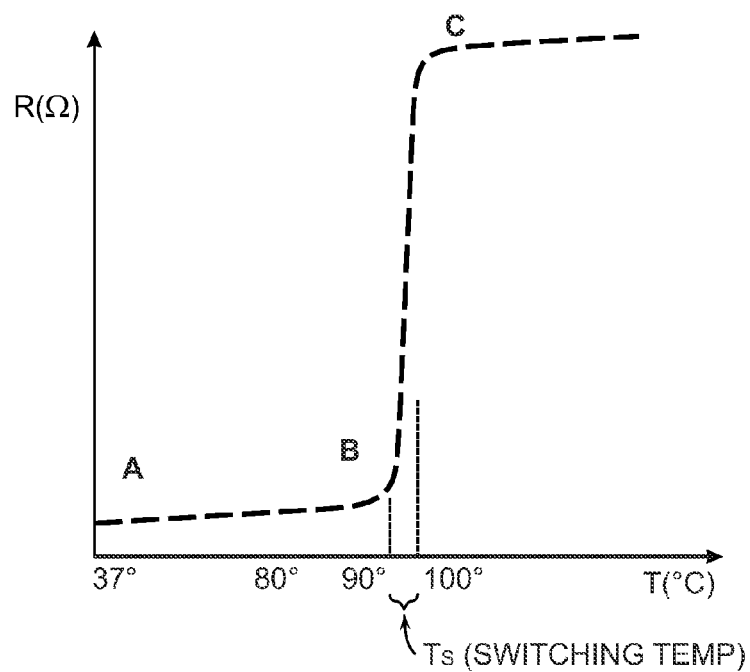
FIG. 9 is an exemplary temperature-resistance curve of a polymeric PTC composition.

In various circumstances, if the ambient temperature surrounding the PTC material, or the temperature of an object engaged by the PTC material, increases instead of the current, the PTC material may stabilize according to Equation (3) at a slightly higher temperature (possibly again at Point B in FIG. 9). Point B in FIG. 9 can also be reached as a result of an increase in current (I) and an increase in ambient temperature Ta. In various circumstances, however, further increases in either or both of these conditions may cause the PTC material to reach a temperature Ts at which the resistance rapidly increases (e.g., from Point B to Point C in FIG. 9). At this stage, large increases in resistance occur with small changes in temperature. In FIG. 9, this occurs between Points B and C, and this vertical or "square" portion of the curve defines the operating region of the PTC composition in its tripped state. The large change in resistance causes a corresponding decrease in current flow in a circuit including or otherwise electrically coupled to the PTC composition. In various circumstances, the resistance, or impedance, can increase by approximately two orders of magnitude, for example, while, in other circumstances, the resistance, or impedance, can increase by approximately four orders of magnitude, for example. In certain circumstances, the change in the resistance, or impedance, can depend on the frequency of the current passing through the PTC material. In at least some circumstances, the resistance can increase by four orders of magnitude when the current is at Rf frequencies, for example, and two orders of magnitude when the current is below Rf frequencies, for example. In any event, because the temperature change between Points B and C in FIG. 9 is very small, the term (T−Ta) in Equation (3) can be replaced by the constant (Ts−Ta), wherein Ts is the current-limiting, or switching, temperature of the device. As a result of the above, Equation (1) can be rewritten as: $I^2*R=V^2/R=U*(Ts-Ta)$—Equation (4). Because U and (Ts−Ta) are now both constants, Equation (4) reduces to $I^2R=$constant; that is, the device now operates in a constant power state under these conditions. Expressing this constant power as $V^2/R$ emphasizes that, in the tripped state, the resistance of the PTC material is proportional to the square of the applied voltage. This relation holds until the composition/device resistance reaches the upper "square" region of the curve (Point C in FIG. 9).

For a PTC composition that has tripped, i.e., exceed its switch temperature, the PTC composition will remain in the tripped state and will remain substantially non-conductive as long as the applied voltage is high enough for the resulting $V^2/R$ to supply and/or exceed the U(Ts−Ta) loss. When the voltage is decreased to the point at which the U(Ts−Ta) loss can no longer be supplied to the PTC material, the PTC material will "reset" or return to its quiescent base resistance, such as points represented by Points A and/or B, for example. Various embodiments can comprise PTC materials that allow for a very rapid bi-directional switching (e.g., a small Δt) between Points B and C along the resistance-temperature curve of FIG. 9. Various embodiments can comprise PTC materials that exhibit a resistance-temperature curve with a high degree of "squareness" at its Ts (see FIG. 9), that is, the embodiment of the PTC material will plot an exceedingly rapid nonlinear PTC effect (e.g., a rapid increase in resistivity) in the range of a selected switching temperature Ts. A vertical, or an at least substantially vertical, curve at Ts can mean that the change from a base quiescent resistance to a maximum current-limiting resistance occurs over a very small temperature range.

Figure 20:
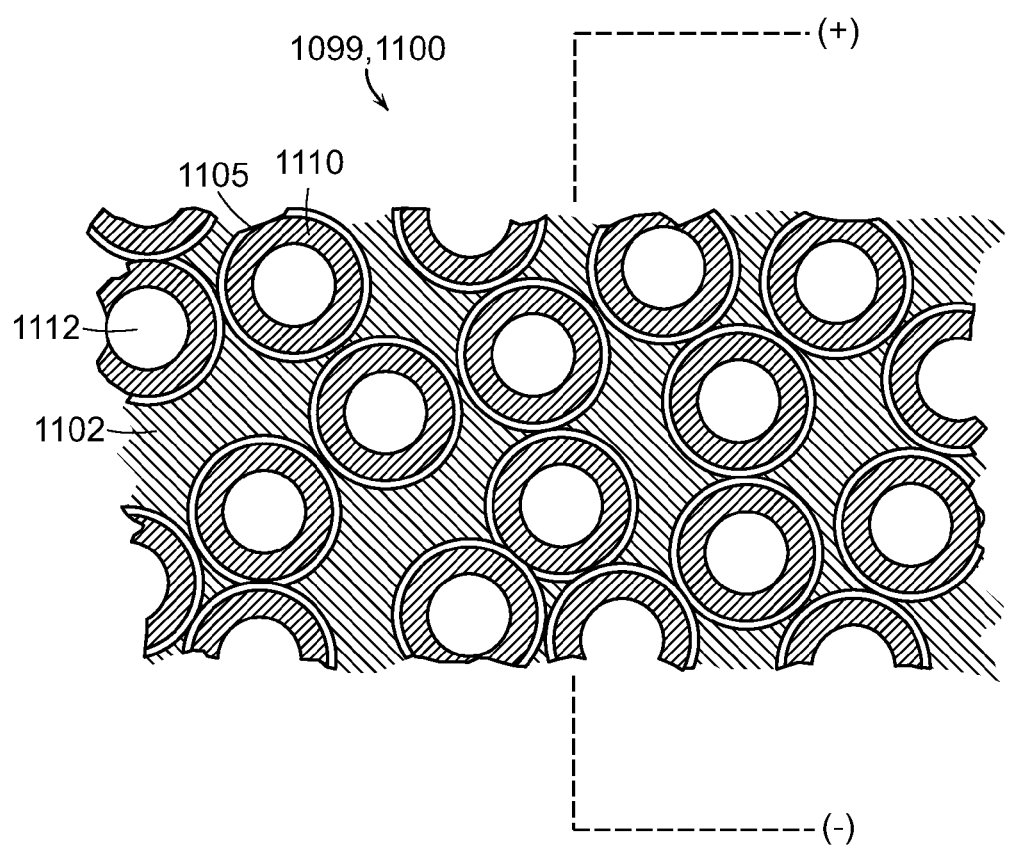
FIG. 20 is a detail view of an exemplary polymeric PTC composition comprising a polymer component having conductively clad, low density microspheres therein.

From the following equation, it can be understood that switching time can be effectively reduced by altering the mass of the PTC composition. The switching time can generally be represented by Equation (5): $\Delta t = m*Cp*(Ts-Ta)/(I^2*R)$. By controlling one or more variables from Equation (5), various embodiments of PTC materials can provide one or both of reduced switching time and/or a square resistance-temperature curve. An exemplary embodiment of a conductive polymer composition/polymer composite which provides a greatly increased switching speed can utilize thermally insulative, low mass, yet electrically conductive dispersed nanospheres and/or microspheres. It has also been found that the embodiments of the above described polymer composite can provide a very low or minimum resistance in its initial quiescent state. At the same time, a polymer with thermally insulative, low mass conductive particles can provide for an increased Imax property, i.e., the maximum current the PTC composition can withstand without damage. As schematically depicted in FIG. 20, various embodiments of conductive polymer compositions exhibiting PTC properties can comprise a PTC composite 99 comprising a polymer matrix 100 including a polymer base material 102 with dispersed conductive elements which, in various embodiments, can have low densities and corresponding low thermal conductivity properties. In at least one embodiment, an exemplary polymeric PTC composite can utilize core-shell particles comprising a core 105 having a very low mass and very low thermal conductivity, such as microspheres and/or nanospheres having a nanoscale conductive coating indicated at 110. In one embodiment, referring to FIG. 20, the core 105 of the conductive dispersed elements can comprise glass microspheres with a hollow portion 112, but solid and/or porous glass microspheres or filaments could be used in addition to or in lieu of the above, for example.

Figure 21:
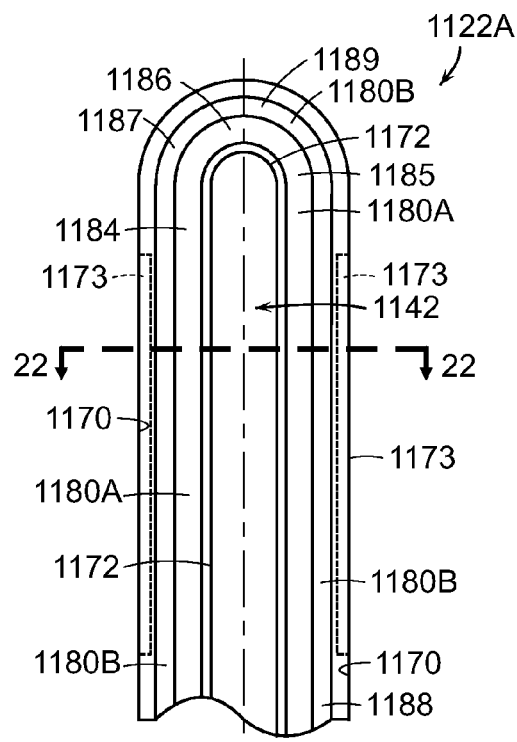
FIG. 21 is a partial bottom view of a jaw of an electrosurgical instrument comprising a first PTC composition having a first switching temperature and a second PTC composition having a second switching temperature.
Figure 22:
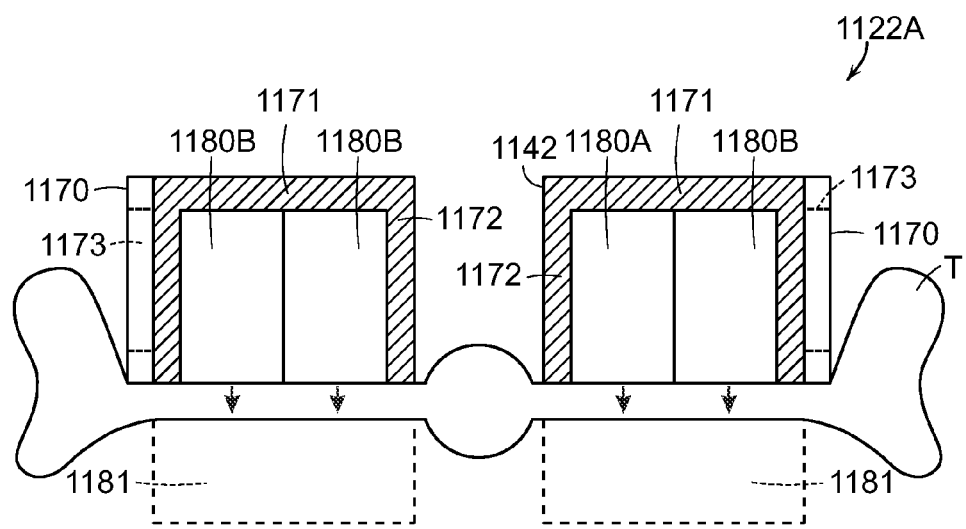
FIG. 22 is a cross-sectional view of the jaw of FIG. 21 taken along line 22-22 in FIG. 21.

In various embodiments, referring now to FIG. 21, a jaw 1122A of an end effector of an electrosurgical instrument can include a first electrode 1180A comprised of a first positive temperature coefficient (PTC) material and, in addition, a second electrode 1180B comprised of a second PTC material. The first electrode 1180A can comprise a first side 1184, a second side 1185 positioned opposite the first side 1184, and a distal end 1186 portion connecting the first and second sides. The second electrode 1180B can, similarly, comprise a first side 1187 positioned adjacent to the first side 1184 of the first electrode 1180A, a second side 1188 positioned adjacent to the second side 1185 of the first electrode 1180A, and a distal end portion 1189 connecting the first and second sides of the second electrode 1180B. As illustrated in FIG. 21, the second electrode 1180B is positioned around the perimeter of the first electrode 1180A such that the second electrode 1180B surrounds the first electrode 1180A. Referring now to FIGS. 21 and 22, the jaw 1122a can comprise a substantially U-shaped channel comprising an outer sidewall 1170, an inner sidewall 1172, and a base 1171 connecting the sidewalls 1170 and 1172, wherein the sidewalls 1170 and 1172 can define a gap therebetween configured to receive electrodes 1180A and 1180B securely therein. In certain embodiments, the electrodes 1180A and 1180B can be press-fit into the gap intermediate sidewalls 1170 and 1172 and/or secured into place using fasteners, for example. In at least one embodiment, the sidewalls of the first, or inner, electrode 1180A can be in abutting contact with the sidewalls of the second, or outer, electrode 1180B. In certain other embodiments, an insulative material can be positioned intermediate the first and second electrodes 1180A and 1180B. In various embodiments, the jaw 1122a can further comprise insulative material positioned intermediate the electrodes 1180A and 1180B and the sidewalls 1170 and 1172, respectively, while, in other embodiments, the electrodes 1180A and 1180B can be in abutting contact with the sidewalls 1170 and 1172. Similarly, in at least one embodiment, the jaw 1122A can further comprise an insulative material positioned intermediate the electrodes 1180A and 1180B and the base 1171 while, in other embodiments, the electrodes 1180A and 1180B can be in abutting contact with the base 1171.

Figure 23:
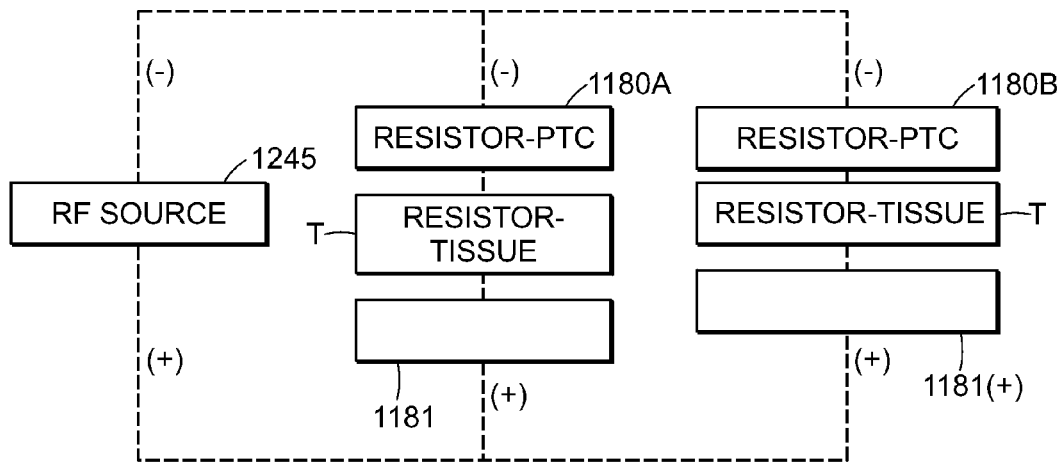
FIG. 23 is an electrical schematic of an electrosurgical instrument comprising the jaw of FIGS. 21 and 22.

In various embodiments, further to the above, a second jaw of the electrosurgical instrument can comprise an opposing electrode 1181 positioned opposite the first and second electrodes 1180A and 1180B. In use, referring again to FIG. 22, tissue "T" can be captured intermediate the first jaw 1122A and the second jaw 1122B of the electrosurgical instrument such that the tissue T is compressed between the electrodes 1180A, 1180B and the return electrode 1181. As discussed above, a voltage differential can be generated between the electrode 1180A and the opposing electrode 1181 and, similarly, between the electrode 1180B and the opposing electrode 1181 such that current can flow between the electrodes and through the tissue T. An electrical schematic of this arrangement is depicted in FIG. 23 wherein the first electrode 1180A and the second electrode 1180B are part of parallel circuits electrically coupled with the RF source 1245. More particularly, the first electrode 1180A is part of a first circuit comprising electrode 1180A, tissue T, and opposing electrode 1181 wherein each of these elements can comprise resistive, and/or capacitive, properties. With regard to this first circuit, the first electrode 1180A is electrically coupled to the negative terminal of the RF source 1245 and the opposing electrode 1181 is electrically coupled to the positive terminal of the RF source 1245, although the reverse arrangement may be possible. Similarly, the second electrode 1180B is part of a second circuit comprising second electrode 1180B, tissue T, and opposing electrode 1181 wherein each of these elements can comprise resistive, and/or capacitive, properties. With regard to this second circuit, the second electrode 1180B is electrically coupled to the negative terminal of the RF source 1245 and the opposing electrode 1181 is electrically coupled to the positive terminal of the RF source 1245, although the reverse arrangement may be possible.

As discussed above, the first electrode 1180A can be comprised of a first PTC material and the second electrode 1180B can be comprised of a second PTC material. In various embodiments, the first PTC material can comprise a first switching temperature while the second PTC material can comprise a second switching temperature. In various embodiments, the first and second switching temperatures can be between approximately 80 degrees Celsius and approximately 150 degrees Celsius, for example. In certain embodiments, the first and second switching temperatures can be a function of the clamping pressure applied to the tissue by the first and second jaws, as described in greater detail below. In various circumstances, the switching temperature can be inversely proportional to the clamping pressure, i.e., the switching temperature may be lower for higher clamping pressures, for example. In any event, when the first and second PTC materials are below their switching temperatures, the first and second electrodes 1180A and 1180B can both have an electrical resistance which permits sufficient current, i.e., current sufficient to therapeutically treat and/or irreversibly alter the tissue being treated, to be conducted through the electrodes 1180A and 1180B and the tissue T. As discussed above, the flow of current through the electrodes 1180A, 1180B, tissue T, and the opposing electrode 181 can generate heat within the tissue and electrodes 1180A and 1180B and, as a result, cause the temperature of the PTC materials to rise. In various embodiments, the first PTC material of first electrode 1180A can have a first switching temperature which is higher than the second switching temperature of the second PTC material of second electrode 1180B wherein, as a result, the second electrode 1180B can "shut-off" or "switch-off" before the first electrode 1180A. Stated another way, the second electrode 1180B can reach its switching temperature before the first electrode 1180A reaches its switching temperature and, once the second electrode 1180B has reached its switching temperature, the electrical resistance of the second electrode 1180B can increase significantly, as outlined above. In such circumstances, the flow of current through the tissue T can be substantially limited to a flow of current between the first electrode 1180A and the opposing electrode 181 at least until the first PTC material of the first electrode 1180A reaches its switching temperature and the electrical resistance of the first electrode 1180A increases significantly. In various circumstances, an electrical resistance can increase significantly when it increases by a factor of approximately 2, 4, 10, 100, and/or 1000, for example, at a specific switching temperature and/or at a switching temperature comprising a narrow transition range of temperatures.

Figure 24:
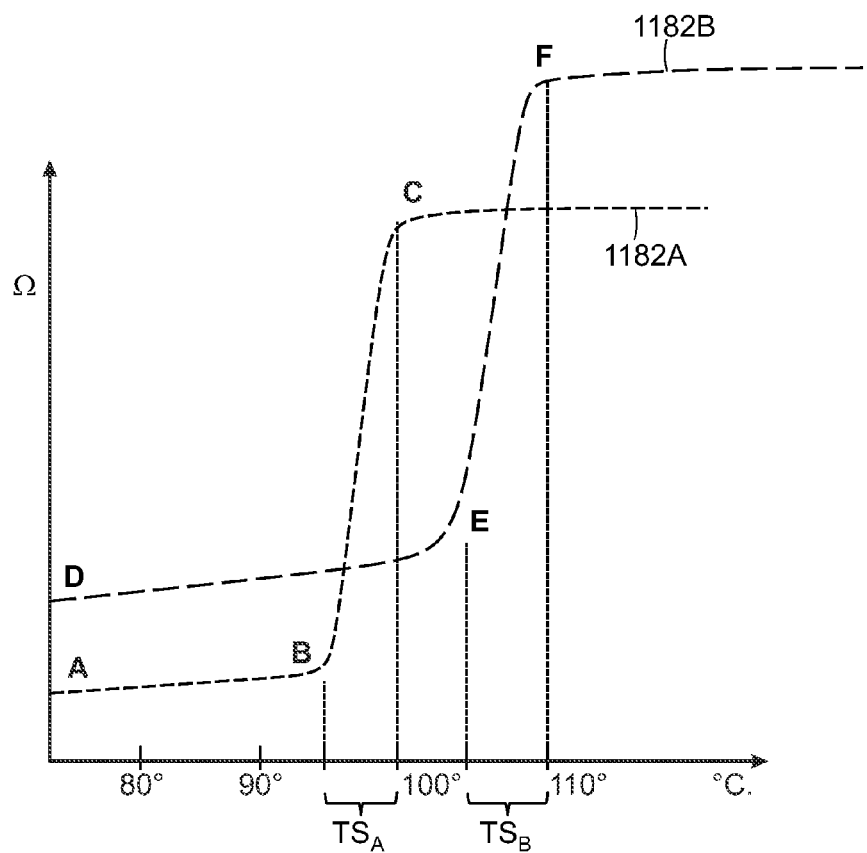
FIG. 24 depicts a first temperature-resistance curve of a first PTC material and a second temperature-resistance curve of a second PTC material used in the same electrosurgical instrument.

In various circumstances, referring now to FIG. 24, the temperature-resistance relationship of the first PTC material of the first electrode 1180A can be plotted by the curve 1182A and the temperature-resistance relationship of the second PTC material of the second electrode 1180B can be plotted by the curve 1182B. As illustrated in FIG. 24, the curves 1182A and 1182B depict that that the first PTC material has a first, or initial, electrical resistance which is lower than first, or initial, electrical resistance of the second PTC material. Alternatively, although not depicted, the first, or initial, electrical resistance of the second PTC material can be lower than the first, or initial, electrical resistance of the first PTC material. In any event, the curves 1182A and 1182B also depict that the resistance of the first PTC material can increase significantly from Points B to C to a second electrical resistance at the switching temperature TsA while, at the same temperature, the resistance of the second PTC material can continue to increase incrementally between points D and E. Once the switching temperature TsB (point E) is reached, the resistance of the second PTC material can increase significantly from points E to F while, at the same temperature, the switched resistance of the first PTC material only increases incrementally. Any additional increase in temperature, as depicted by curves 1182A and 1182B, may only result in incremental increases of the switched resistances of the first and second PTC materials. As the reader will note, the switched resistance of the second PTC material is larger than the switched resistance of the first PTC material after both the materials have exceeded their switching temperatures. Alternatively, although not depicted, the switched electrical resistance of the second PTC material can be lower than the switched electrical resistance of the first PTC material.

In various embodiments, referring again to FIG. 22, the end effector of the electrosurgical instrument can comprise a central axis 1125, along which a cutting slot 1142 can be defined, wherein the cutting slot 1142 can be configured to slidably receive a cutting member, or knife, therein. Further to the above, the first electrode 1180A can be positioned closer to the central axis of the end effector than the second electrode 1180B and, as the switching temperature of the second PTC material is lower than the switching temperature of the first PTC material, the second, or outer, electrode 1180B may stop conducting current, or at least substantially stop conducting current, before the first, or inner, electrode 1180A stops, or at least substantially stops, conducting current. In such circumstances, the current, and the heat being generated by the current, may be centralized in the end effector near the central axis of the end effector as opposed to the outer periphery of the end effector and, as a result, the lateral spread of heat from the end effector into the adjacent tissue may be reduced. In certain embodiments, the jaws of the end effector can further comprise one or more materials 1173 extending around at least a portion of the perimeter of the jaws, wherein the materials 1173 can be configured to reduce the lateral, or outward, spread of heat from the end effector. In at least one such embodiment, the materials 1173 can be comprised of at least one high resistance material which can restrict, or at least substantially restrict, the flow of current therethrough. More particularly, the sidewalls 1170, 1172 and base 1171 can, in certain circumstances, comprise a return path for the current flowing through the tissue T, wherein, in the event that the sidewalls 1170, 1172 and base 1171 comprise a high resistance material 1173, the flow of current through the outer surfaces, or outer portions, of the jaws can be reduced. As a result, the flow of current, or current density, between the first and second jaws may be more centralized toward the inside, or middle, of the jaws as opposed to the outside of the jaws and, accordingly, the lateral or outward spread of heat from the jaws can be reduced. In certain embodiments, the high resistance materials 1173 can be embedded in sidewalls 1170, 1172 and/or base 1171 while, in some embodiments, the materials comprising the sidewalls 1170, 1172 and/or base 1171 can be comprised of a high resistance material. In certain embodiments, the material 1173 and/or any other outer portions of the jaws can be comprised of one or more PTC materials. In at least one such embodiment, the PTC materials can comprise a switching temperature which is lower than the switching temperature of the PTC materials in the electrodes, for example.

In various embodiments, referring now to FIGS. 28-33, an end effector of a surgical instrument, such as end effector 1410, for example, can comprise a first jaw 1422A and a second jaw 1422B, wherein at least one of the jaws 1422A, 1422B can comprise, further to the above, one or more inserts positioned within one or more channels and/or slots in the jaws 1422A, 1422B, for example. In at least one embodiment, the first jaw 1422A can comprise at least one slot 1423 which can be configured to receive an insert 1424A. The insert 1424A can comprise a circular, or at least substantially circular, retention head 1425 which can be configured to be retained in a circular, or at least substantially circular, portion of slot 1423. In various embodiments, the insert 1424A can further comprise an outer portion 1426A which can comprise an outer profile which can be flush, or at least substantially flush, with the outer profile 1427A of the first jaw 1422A, for example. Similar to the above, the second jaw 1422B can also comprise at least one slot 1423 which can be configured to receive an insert 1424B. Also similar to the above, the outer portion 1426B of the insert 1424B can be flush, or at least substantially flush, with the outer profile 1427B of the second jaw 1422B. In various embodiments, further to the above, the inserts 1424A and/or 1424B, for example, can be comprised of a material having an electrical resistance which is higher than the electrical resistance of the frame portions 1428A and 1428B of jaws 1422A and 1422B, respectively. Owing to the higher resistances in the inserts 1424A and 1424B, during use, the density of current that may flow through the tissue and into the outer portions of the jaw members 1422A and 1422B can be reduced. In various embodiments, further to the above, the inserts 1424A and/or 1424B can be comprised of a positive temperature coefficient (PTC) material which can have, at least initially, a sufficiently low resistance to allow a high density of current to flow from the electrodes 1480 and/or 1481, for example, into the outer portions of jaws 1422A and 1422B. Once the temperature of these PTC materials have exceeded their switching temperatures, however, the electrical resistances of the PTC materials can increase significantly such that the flow of current through the inserts 1424A and 1424B and the outer portions of the jaws 1422A and 1422B can be stopped, or at least significantly reduced. In certain embodiments, a PTC material can be coated onto the outside of at least one of the jaws 1422A and 1422B, for example. In at least one such embodiment, a PTC material could be applied to the jaw frames 1428A and 1428B from a solvent solution and/or from a two phase system, for example. In at least one embodiment, a solvent solution can comprise carbon black particles suspended in a solution comprising alcohol and/or an air-curable adhesive, for example. In certain embodiments, a two phase system can comprise a latex paint, a solvent, insoluble polymer micelles, and/or suspended particles, such as carbon, for example. In at least one embodiment, an insulating coating could be sprayed onto the jaw frames 1428A and 1428B, for example, regardless of whether the coating includes a switching temperature property.

Figure 25:
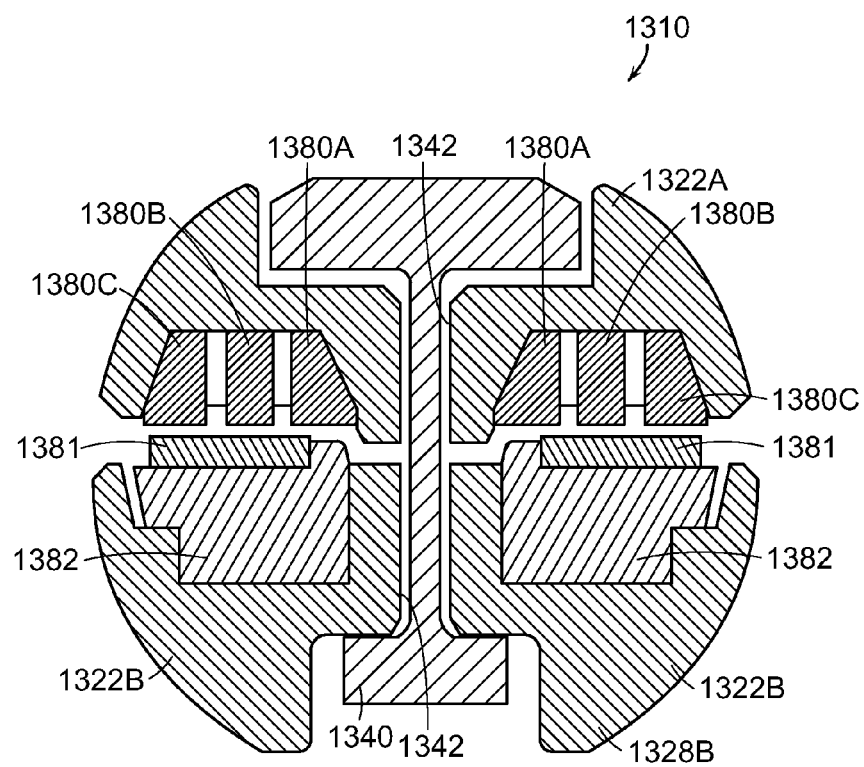
FIG. 25 is a cross-sectional view of a first jaw and a second jaw of an electrosurgical instrument, wherein the first jaw comprises a first PTC composition having a first switching temperature, a second PTC composition having a second switching temperature, and a third PTC composition having a third switching temperature.
Figure 26:
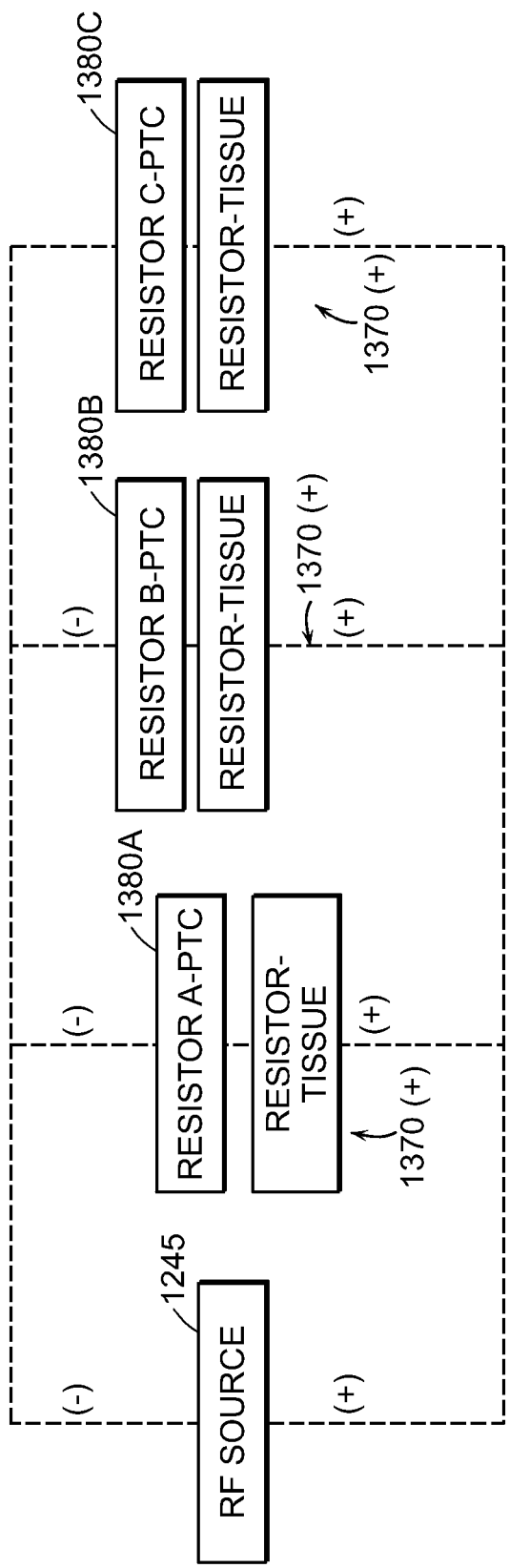
FIG. 26 is an electrical schematic of the electrosurgical instrument of FIG. 25.
Figure 28:
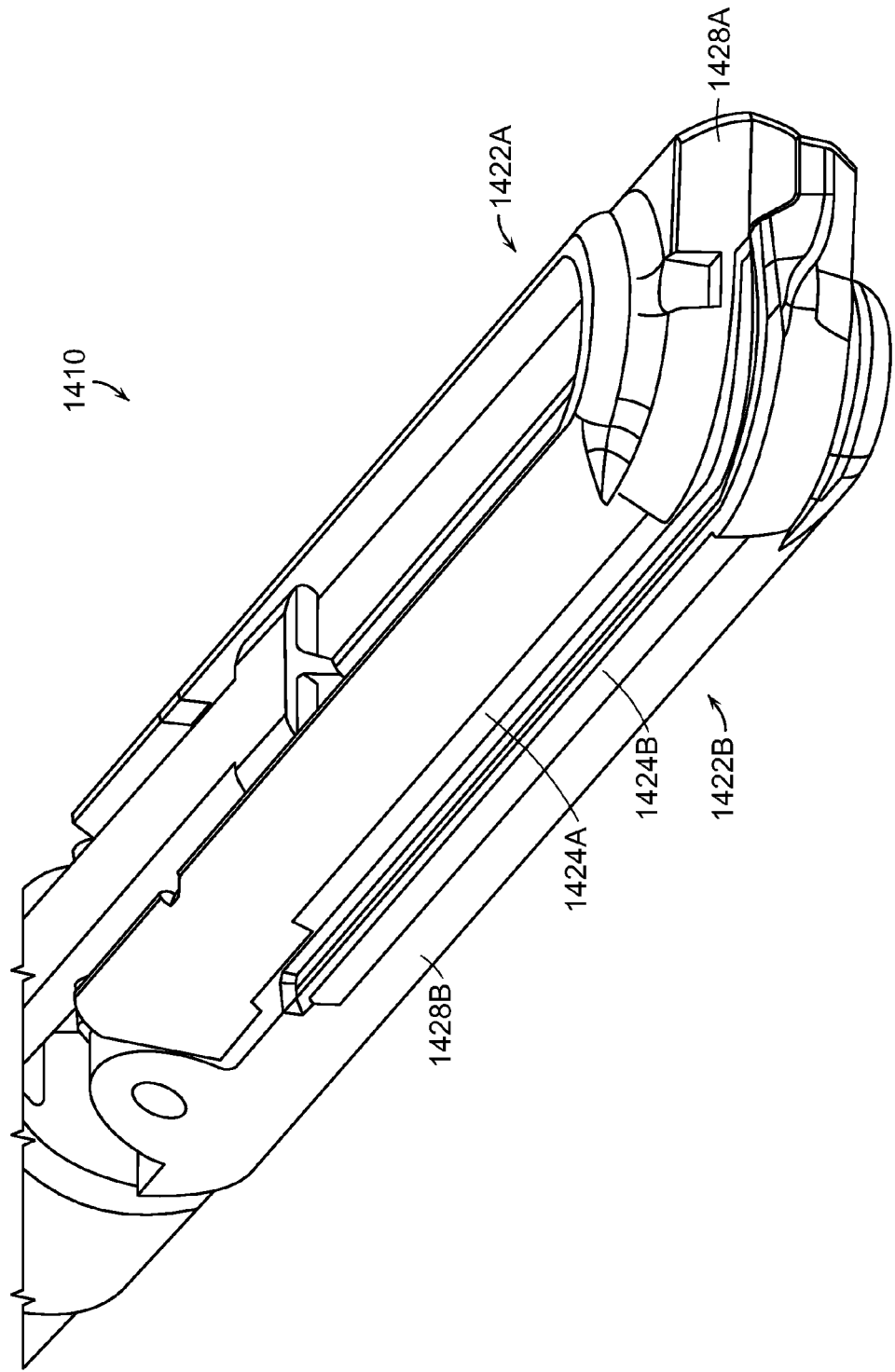
FIG. 28 is a perspective view of an end effector of a surgical instrument comprising PTC materials embedded in first and second jaws of the end effector.
Figure 29:
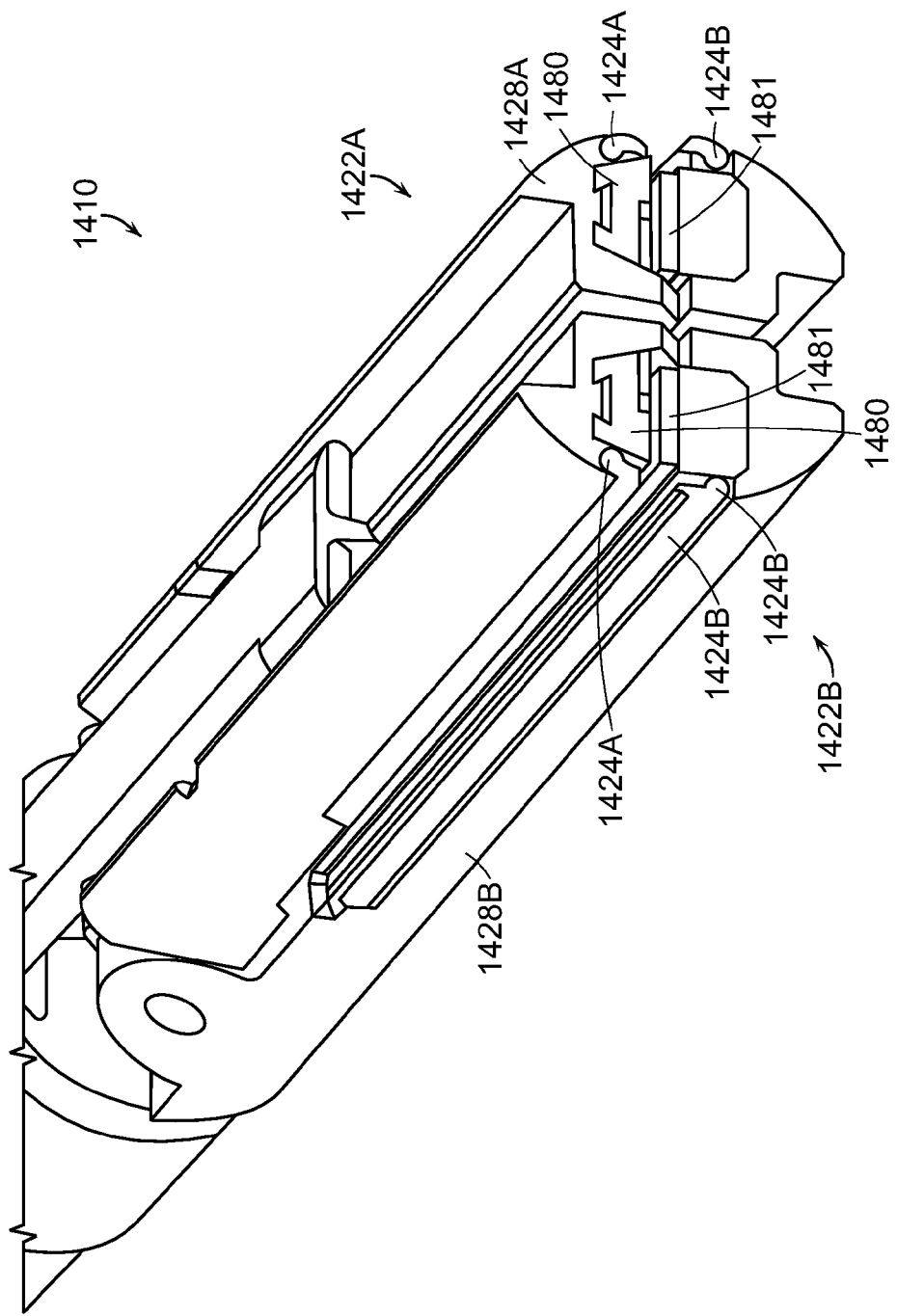
FIG. 29 is a cross-sectional view of the end effector of FIG. 28.
Figure 30:
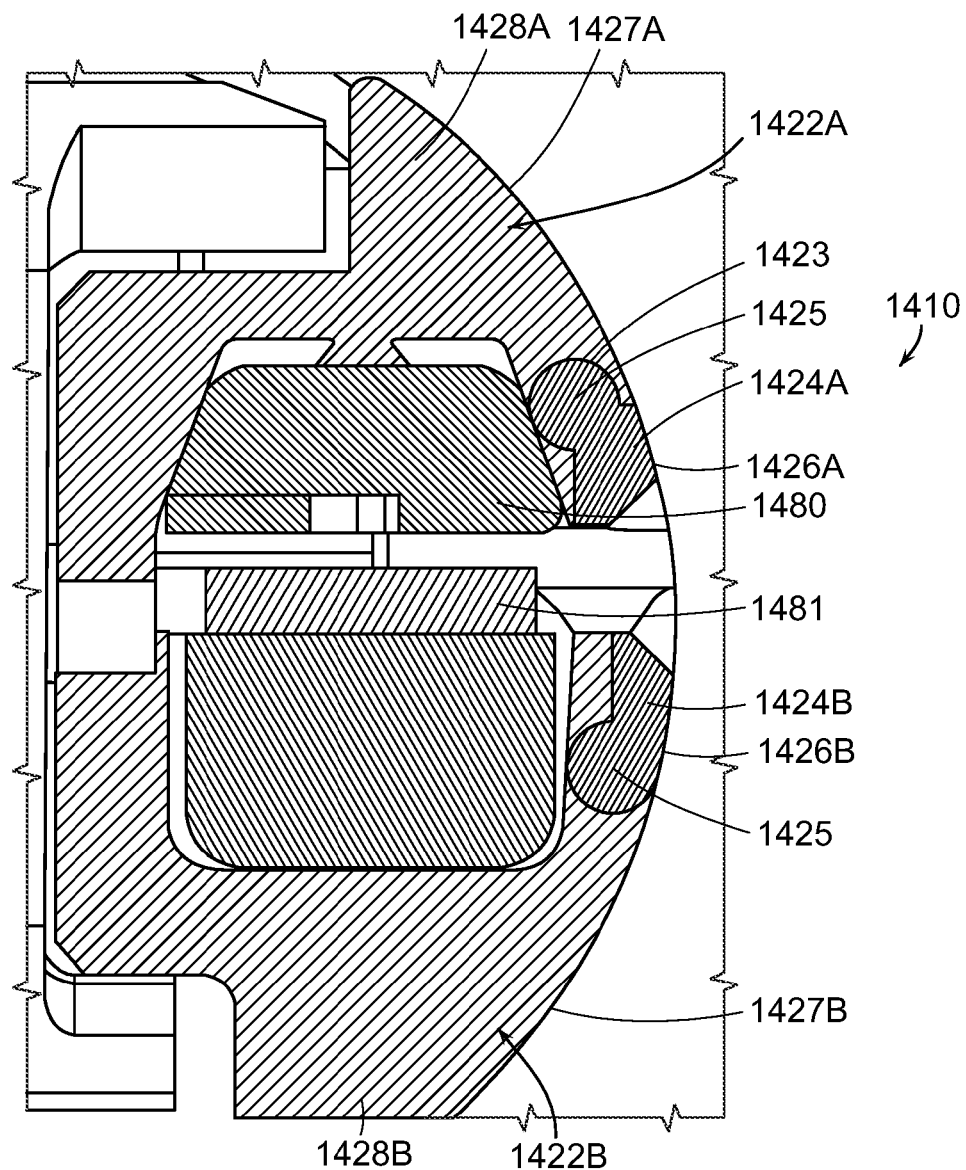
FIG. 30 is a detail view of the cross-sectional view of FIG. 29.
Figure 31:
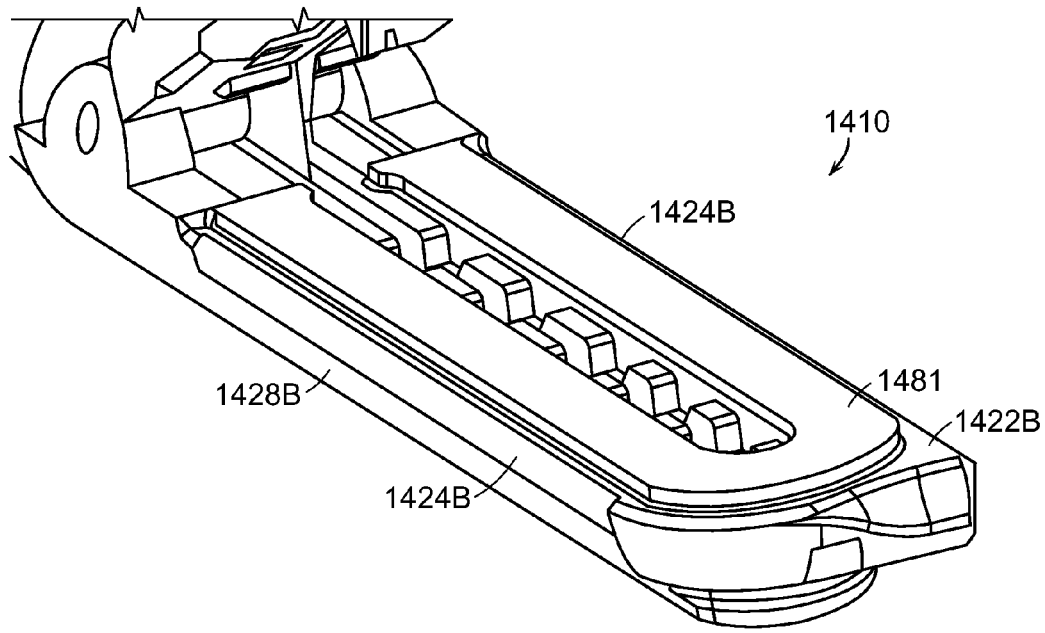
FIG. 31 is a partial perspective view of the end effector of FIG. 28 in an open configuration.
Figure 32:
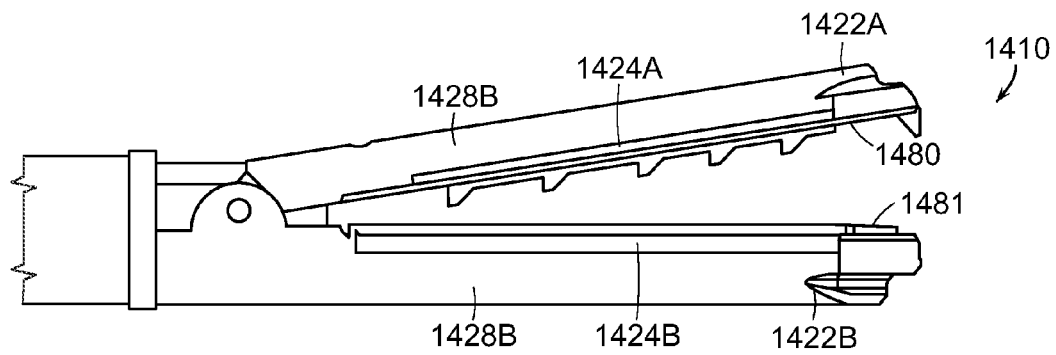
FIG. 32 is a side view of the end effector of FIG. 28 in an open configuration.
Figure 33:
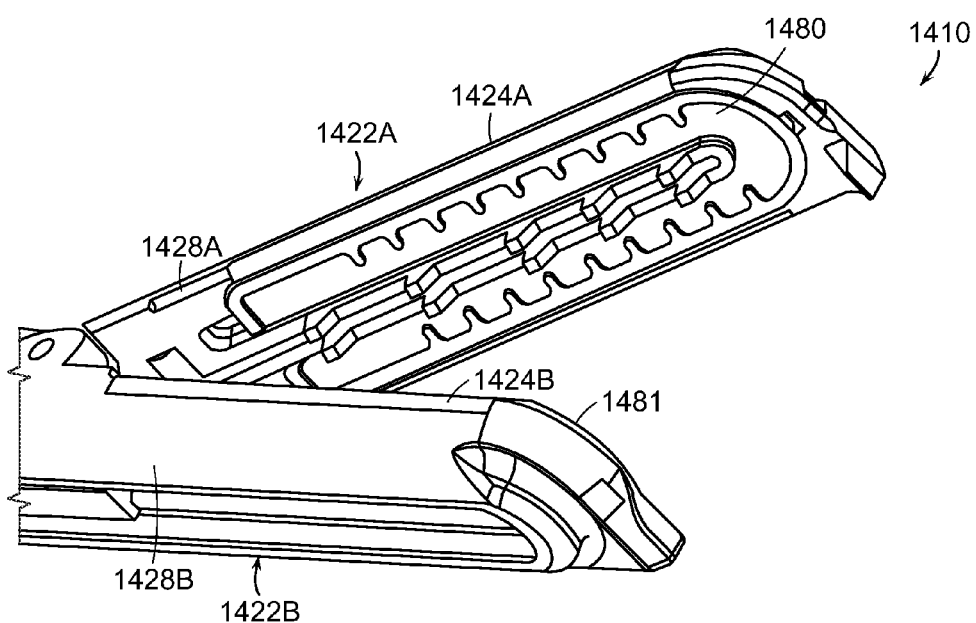
FIG. 33 is another perspective view of the end effector of FIG. 28 in an open configuration.

In various embodiments, referring now to FIG. 25, an end effector, such as end effector 1310, for example, can comprise more than two electrodes comprised of PTC materials having different switching temperatures. In at least one embodiment, the end effector 1310 can comprise a first jaw 1322A and a second jaw 1322B wherein the first jaw 1322A, for example, can comprise a first electrode 1380A comprised of a first PTC material having a first switching temperature, a second electrode 1380B comprised of a second PTC material having a second switching temperature, and a third electrode 1380C comprised of a third PTC material having a third switching temperature. Similar to electrodes 1180A and 1180B, electrodes 1380A, 1380B, and/or 1380C can comprise substantially U-shaped electrodes having opposing first and second sides as illustrated in FIG. 25. In at least one embodiment, the electrodes 1380A, 1380B, and 1380C can be separated from one another by air gaps and/or insulative materials, for example. In any event, similar to the above, the second jaw 1322B can comprise an opposing electrode 1381 which can be positioned opposite the electrodes 1380A, 1380B, and 1380C such that, in use, current can flow between the electrodes and the tissue positioned therebetween. In certain embodiments, referring again to FIG. 25, the second jaw 1322B can further comprise an insulator 1382 which can be configured to electrically insulate the opposing electrode 1381 from the outer jaw portion, or frame, 1328B of second jaw 1322B. An electrical schematic of the above-described arrangement is depicted in FIG. 26 wherein the first electrode 1380A, the second electrode 1380B, and the third electrode 1380C are part of parallel circuits electrically coupled with the RF source 1245. More particularly, the first electrode 1380A is part of a first circuit comprising electrode 1380A, tissue T, and opposing electrode 1381 which can all comprise resistive, and/or capacitive, properties. With regard to this first circuit, the first electrode 1380A is electrically coupled to the negative terminal of the RF source 1245 and the opposing electrode 1381 is electrically coupled to the positive terminal of the RF source 1245, although the reverse arrangement may be possible. Similarly, the second electrode 1380B is part of a second circuit comprising second electrode 1380B, tissue T, and opposing electrode 1381 which can all comprise resistive, and/or capacitive, properties. With regard to this second circuit, the second electrode 1380B is electrically coupled to the negative terminal of the RF source 1245 and the opposing electrode 1381 is electrically coupled to the positive terminal of the RF source 1245, although the reverse arrangement may be possible. Similarly, the third electrode 1380C is part of a third circuit comprising third electrode 1380C, tissue T, and opposing electrode 1381 which can all comprise resistive, and/or capacitive, properties. With regard to this third circuit, the third electrode 1380C is electrically coupled to the negative terminal of the RF source 1245 and the opposing electrode 1381 is electrically coupled to the positive terminal of the RF source 1245, although the reverse arrangement may be possible.

In various embodiments, further to the above, the second switching temperature of the second PTC material (electrode 1380B) can be lower than the first switching temperature of the first PTC material (electrode 1380A) and the third switching temperature of the third PTC material (electrode 1380C) can be lower than the second switching temperature of the second PTC material. In various circumstances, also further to the above, the current flowing through the electrodes and the tissue can cause the temperature of the electrodes 1380A, 1380B, and 1380C to increase, wherein the switching temperature of the third PTC material of the third electrode 1380C can be exceeded before the switching temperatures of the PTC materials of the electrodes 1380A and 1380B. In such circumstances, the resistance of the third, or outer, electrode 1380C can increase significantly such that the current, or at least a substantial portion of the current, flowing between the first and second jaws flows between the electrodes 1380B, 1380A and the opposing electrode 1381. As the temperature of the tissue and the electrodes continue to increase, the switching temperature of the second PTC material of second electrode 1380B can be exceeded followed by the switching temperature of the first PTC material of first electrode 1380A. Similar to the above, the resistance of the second, or middle, electrode 1380B can increase significantly when its switching temperature is exceeded such that the current, or at least a substantial portion of the current, flowing between the first and second jaws flows between the first, or inner, electrode 1380A and the opposing electrode 1381, wherein, after the switching temperature of the first PTC material has been exceeded, the current flowing between the first and second jaws 1322A, 1322B can be stopped, or at least substantially stopped. In various embodiments, as a result of the above, the outer electrodes of the end effector can be "switched off" before the inner electrodes, although other embodiments are envisioned in which the electrodes can be comprised of suitable PTC materials which can allow the electrodes to "switch off" in any suitable order. In certain embodiments, the electrodes comprising PTC materials having the highest switching temperature can be positioned outwardly in relation to electrodes comprising PTC materials having a lower switching temperature, for example.

In various embodiments, further to the above, the first jaw 1322A can be moved from an open position into a closed position relative to the second jaw 1322B wherein, at such point, a voltage potential can be applied simultaneously to the electrodes 1380A, 1380B, and/or 1380C such that current flows through the tissue positioned intermediate the first and second jaws 1322A, 1322B. Alternatively, upon closing the first jaw 1322A, a voltage potential may be applied sequentially to the electrodes 1380A, 1380B, and 1380C. In at least one such embodiment, a voltage potential may first be applied to the first electrode 380A in order to begin the sealing process of the tissue in the center of the end effector. Thereafter, a voltage potential may be applied to the second electrode 1380B in order further seal the tissue. In various embodiments, the voltage potential applied to the second electrode 1380B can be applied during and/or after the period of time in which the voltage potential is applied to the first electrode 1380A. In certain embodiments, the electrosurgical instrument can comprise a computer, or controller, such as a microprocessor, for example, which can comprise a timer circuit configured to apply the voltage potential to the first electrode for a first period of time and, similarly, apply the voltage potential to the second electrode for a second period of time. In certain embodiments, the electrosurgical instrument can further comprise a sensor, for example, operably coupled with the computer which can be configured to detect the advancement of the cutting member through the end effector and, upon sensing the advancement of the cutting member, the computer can apply the voltage potential to the second electrode 1380B, reduce the voltage potential being applied to the first electrode 1380A, and/or stop applying the voltage potential to the first electrode 1380A altogether, for example. After a certain period of time and/or after the sensor has detected a predetermined amount of movement of the cutting member, the computer can apply a voltage potential to the third electrode 1380C, reduce the voltage potential being applied to the first electrode 1380A and/or second electrode 1380B, and/or stop applying the voltage potential to the first electrode 1380A and/or second electrode 1380B altogether, for example. In certain embodiments, the computer can be configured to evaluate the current passing through the electrodes 1380A, 1380B, and/or 1380C and/or evaluate the electrical resistances of the electrodes 1380A, 1380B, and/or 1380C in order to determine whether the switching temperatures of the PTC materials have been reached. In at least one embodiment, upon detecting that the switching temperature of the first PTC material of the first electrode 1380A has been reached, the computer can apply a voltage potential to the second electrode 1380B and, after detecting that the switching temperature of the second PTC material of second electrode 1380B has been reached, apply a voltage potential to the third electrode 1380C, for example.

Figure 27:
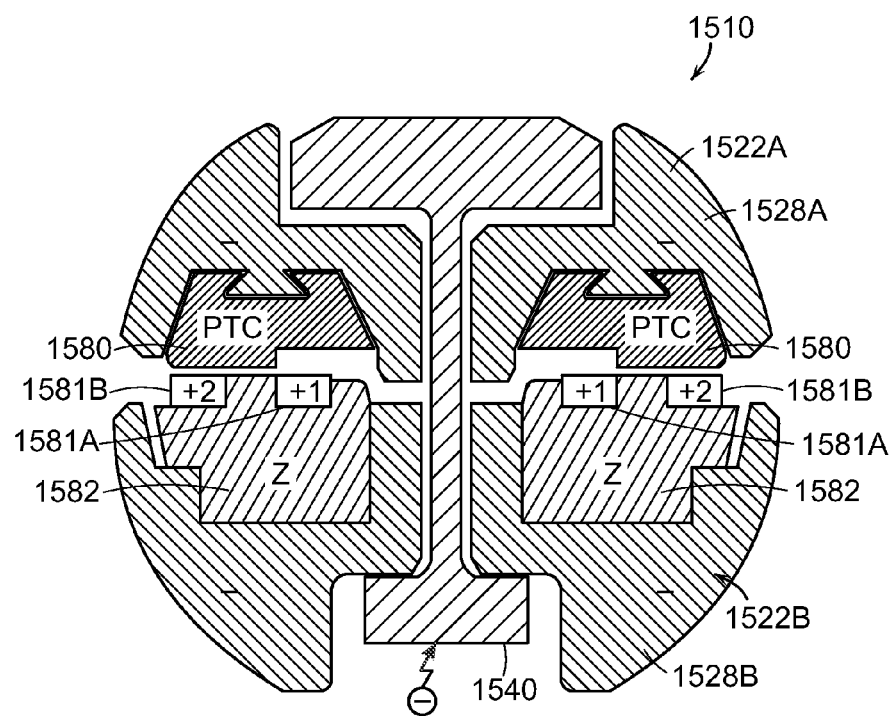
FIG. 27 is a cross-sectional view of a first jaw and a second jaw of an electrosurgical instrument comprising first and second electrodes positioned opposite to an electrode comprising a PTC composition.

In various embodiments, referring now to FIG. 27, an end effector, such as end effector 1510, for example, can comprise a first jaw 1522A and a second jaw 1522B wherein the first jaw 1522A can comprise an electrode 1580 comprised of a PTC material. The second jaw 1522B can comprise a first electrode 1581A and a second electrode 1581B wherein, similar to electrodes 1180A and 1180B, the electrodes 1581A and 1581B can comprise substantially U-shaped electrodes having opposing first and second sides. In at least one embodiment, the electrodes 1581A and 1581B can be electrically insulated from one another, and/or from the frame 1528B, for example, by one or more insulators, such as insulator 1582, for example. Also similar to the above, the electrode 1580 can be positioned opposite the electrodes 1581A and 1581B when the first jaw 1522A is positioned in its closed position opposite the second jaw 1522B such that, in use, current can flow between the electrodes and the tissue positioned therebetween. In various embodiments, the electrodes 1581A and 1581B may be comprised of a conductive material and can be selectively coupled with the positive terminal of a power source, for example, while the electrode 1580 can be coupled with the negative terminal, or ground, of the power source, for example. In addition to the above, the cutting member 1540 and the frames 1528A, 1528B of jaws 1522A, 1522B, respectively, can also be operably coupled to the negative terminal, or ground, of the power source. During use, in at least one such embodiment, current can flow from the electrodes 1581A and 1581B, through the tissue positioned intermediate the jaws 1522A and 1522B, and into at least one of the PTC electrode 1580, the first frame 1528A, the second frame 1528B, and/or the cutting member 1540. In various circumstances, a substantial proportion of the current may flow into the opposing PTC electrode 1580, at least when the PTC electrode 1580 is below its switching temperature, wherein smaller proportions of the current may flow into the frames 1528A, 1528B and/or cutting member 1540. When the PTC electrode 1580 has exceeded its switching temperature, the density of current between the electrodes 1581A, 1581B and 1580 can be substantially reduced owing to the substantially increased electrical resistance of the PTC electrode 1580.

In various embodiments, further to the above, an electrosurgical instrument comprising end effector 1510 can further comprise a computer, or controller, such as a microprocessor, for example, which can electrically couple the first electrode 1581A and the second electrode 1581B with the positive terminal of a power source, for example, at the same time such that current can flow between the first electrode 1581A and the PTC electrode 1580 and between the second electrode 1581B and the PTC electrode 1580 simultaneously. In various circumstances, the tissue positioned intermediate the first electrode 1581A and the PTC electrode 1580 can contract, or shrink, due to the thermal effects caused by the current flowing through the tissue while, similarly, the tissue positioned intermediate the second electrode 1581B and the PTC electrode 1580 can contract, or shrink, due to the thermal effects caused by the current flowing through the tissue. In various circumstances, the tissue can shrink when it has reached a temperature between approximately 60 degrees Celsius and approximately 70 degrees Celsius, for example. In various embodiments, the computer can sequentially couple the electrodes 1581A and 1581B with the power source. In at least one such embodiment, the computer can first electrically couple the first electrode 1581A with the power source such that current can flow between the first electrode 1581A and the PTC electrode 1580 and cause the tissue positioned therebetween to shrink. In such circumstances, the shrinking tissue can pull, or apply tension to, the surrounding tissue and, in some circumstances, pull additional tissue into the end effector. With such additional tissue in the end effector, in some circumstances, a better seal, or weld, can be created within the tissue.

When the first electrode 1581A is electrically coupled to the power source, further to the above, the second electrode 1581B can be electrically uncoupled to the power source. In at least one embodiment, the computer can utilize the second electrode 1581B to monitor the impedance of the tissue while the tissue between the first electrode 1581A and the PTC electrode is welded. In at least one such embodiment, the circuit comprising the second electrode 1581B, the tissue, and a return path of the current can be utilized to monitor changes in the impedance and, when changes in the impedance have stopped, or the impedance begins to approach an asymptote, the amount of tissue stretch or pull that can be created by the operation of first electrode 1581A may have reached, or at least nearly reached, its maximum. In various circumstances, the computer of the electrosurgical instrument can then apply a voltage potential to the second electrode 1581B. In such circumstance, the computer can continue to apply the voltage potential to the first electrode 1581A or, alternatively, discontinue applying the voltage potential to the first electrode 1581A. In either event, the tissue positioned intermediate the second electrode 1581B and the PTC electrode can shrink which can, as a result, pull, or apply tension to, the surrounding tissue and pull additional tissue into the end effector 1510. In circumstances where the first electrode 1581A is no longer being used to weld the tissue, the circuit comprising first electrode 1581A, the tissue, and a return path can be utilized, similar to the above, to monitor the impedance of the tissue. In any event, any other suitable operation sequence of the electrodes 1581A and 1581B can be utilized to achieve a desired result. In at least one embodiment, the second electrode 1581B can be utilized to seal the tissue before the first electrode 1581A is used to seal the tissue. In at least one such embodiment, the welded tissue between the second electrode 1581B and the PTC electrode 1580 can entrap, or at least partially entrap, the current and/or heat generated by the first electrode 1581A, when it is operated, within the end effector.

In various embodiments, the cutting member 1540 can be advanced within the end effector 1510 at any suitable time during the above-described sequence. In certain embodiments, the cutting member 1540 can be advanced when the first electrode 1581A is polarized and being used to weld tissue and before the second electrode 1581B is polarized. In at least one embodiment, the cutting member 1540 can be advanced when both the first and second electrodes 1581A and 1581B are polarized, while, in other embodiments, the cutting member 1540 can be advanced while the second electrode 1581B has been polarized and after the first electrode 1581A has been polarized. In various alternative embodiments, further to the above, one of the electrodes 1581A and 1581B can be electrically coupled with the positive terminal of the power source while the other of the electrodes 1581A and 1581B can be electrically coupled with the negative terminal of the power source. In at least one such embodiment, the polarity of the electrodes 1581A and 1581B can then be reversed.

In various embodiments, as described above, the end effector of a surgical instrument can comprise a first jaw member and a second jaw member, wherein the first jaw member can be rotated, or pivoted, toward the second jaw member in order to clamp tissue between the first and second jaw members. In various circumstances, the first jaw member can be pivoted between a fully open position, a fully closed position, and various positions inbetween. In at least one such embodiment, the first jaw member can be pivoted from its open position into a first position in order to apply a first clamping pressure to the tissue and, if so desired, the first jaw member can be further pivoted into a second position in order to apply a second, or larger, clamping pressure to the tissue. In various circumstances, a sufficient, or certain, clamping pressure must be applied to the tissue in order for the tissue to be properly treated by the electrical current heat supplied to, and/or heat generated by, the first and second jaw members via the electrodes positioned therein. In certain embodiments, a surgical instrument can comprise means for preventing, or at least substantially preventing, current from flowing through the tissue unless the tissue is being subjected to a clamping pressure above a certain minimum pressure. In at least one embodiment, one or more of the electrodes in the first and second jaw members can include an electrode comprising a pressure-sensitive (PS) material which can have a first resistance, or impedance, when it is subjected to pressure below the minimum pressure and a substantially higher second resistance, or impedance, when it is subjected to a pressure at and/or above the minimum pressure, as described in greater detail further below.

In various embodiments, further to the above, an electrode in at least one of the first and second jaw members can comprise a pressure-sensitive material including a non-conductive, or at least substantially non-conductive, substrate material and a conductive material dispersed within the substrate material. The pressure-sensitive material can be manufactured such that the conductive material is present within the substrate material in a certain, or predetermined, mass fraction. For example, in at least one such embodiment, the substrate material can be comprised of a polymeric material, such as polyethylene and/or high-density polyethylene (HDPE), for example, and the conductive material can be comprised of carbon black particles, for example. In any event, when the pressure-sensitive material is not being subjected to external pressures, other than atmospheric pressure and/or gravity forces, for example, the pressure-sensitive material may have a first electrical resistance, or impedance, which can make the pressure-sensitive material electrically non-conductive, or at least substantially electrically non-conductive such that current cannot be sufficiently conducted therethrough to either treat or irreversibly alter the tissue captured within the end effector. In such circumstances, the conductive particles can be present in the pressure-sensitive material in a first volumetric density such that the conductive particles are not sufficiently in contact with another in order to form a necessary chain, or chains, of conductive particles for electrical current to pass therethrough. When the pressure-sensitive material is subjected to pressure when the clamping pressure is applied to the tissue, for example, the conductive particles can be moved toward each other such that they have a larger volumetric density within the pressure-sensitive material. After a sufficient, or minimum, pressure has been applied to the pressure-sensitive material, the conductive particles can make sufficient contact with one another to form one or more conductive paths though the pressure-sensitive material. Once such conductive paths have been established, the current can flow through the pressure sensitive material and through the tissue positioned between the first and second jaw members.

When the pressure-sensitive material has been sufficiently compressed in order to conduct electrical current, further to the above, the pressure-sensitive material may have a resistance, or impedance, which is far lower than the resistance, or impedance, of the pressure-sensitive material when it is not being compressed, for example. In certain embodiments, as a result, the pressure-sensitive material may operate as a switch which switches between a first, or higher, resistance and a second, or lower, resistance once a sufficient, or switching, pressure has been applied to the pressure-sensitive material. In certain embodiments, the switching pressure can be approximately 1000 psi, approximately 1500 psi, approximately 2000 psi, and/or approximately 2500 psi, for example. In at least one embodiment, the switching pressure can be between approximately 1000 psi and approximately 2500 psi, for example. In at least one embodiment, the minimum switching pressure can be approximately 1500 psi, for example. In certain embodiments, the switching pressure can be greater than 2500 psi, for example. In various embodiments, the switching pressure of an electrode material can be affected by moisture, the power applied, and/or time, for example. In any event, in various circumstances, the first resistance can be approximately 10 times larger, approximately 100 times larger, and/or approximately 1000 times larger that the second resistance, for example. In at least some such circumstances, as a result, the pressure-sensitive material, at its first resistance, can prevent, or at least substantially inhibit, current from flowing therethrough while the pressure-sensitive material, at its second resistance, can permit current to flow therethrough with a sufficient magnitude in order to treat the tissue in the end effector, for example. In various circumstances, the switching pressure can actually comprise, or be defined by, a range of pressures wherein, once the applied pressure enters into this range, the resistance of the pressure-sensitive material can begin to decrease from the first resistance to the second resistance as the pressure is increased. In various circumstances, the resistance can decrease linearly and/or geometrically between the first resistance and the second resistance. In certain embodiments, carbon black particles can be present in HDPE, for example, in sufficient quantities so as to create a desired second resistance within the electrode, such as approximately 8 ohms, approximately 100 ohms, and/or approximately 1000 ohms, for example. In various embodiments, the resistance of the electrode material can be inversely proportional to the density of the carbon black particles within the electrode material. For example, a higher density of carbon black particles can result in a lower resistance of the electrode material.

In various other embodiments, an electrode can comprise a pressure-sensitive material which does not comprise a distinct switching pressure and/or distinct pressure range in which the resistance of the pressure-sensitive material changes significantly; rather, the resistance of such a pressure-sensitive material can decrease gradually as the pressure applied to the pressure-sensitive material is increased gradually. In various embodiments, the magnitude of the current that can flow through the pressure-resistance material can increase monotonically as the pressure applied to the pressure-resistance material is increased, at least for a given voltage potential applied across the pressure-resistance material. The change in resistance can occur linearly and/or geometrically in an inversely proportional manner to the applied pressure. Correspondingly, the change in current, for a given voltage potential, can occur linearly and/or geometrically in a directly proportional manner to the applied pressure. In such embodiments, a first clamping pressure applied to the pressure-sensitive material can result in the pressure-sensitive material having a first resistance, a second clamping pressure can result in a second resistance, and a third clamping pressure can result in a third resistance, and so forth.

The above-discussed pressure-sensitive materials, and/or any other pressure-sensitive materials disclosed herein, can be formed utilizing any suitable manufacturing process. In various embodiments, the pressure-sensitive material, including those comprised of a polymeric substrate, for example, can be formed utilizing an injection molding process. In at least one such embodiment, polyethylene can be heated until its melting temperature has been reached and/or exceeded. Before, during and/or after this heating process, carbon black particles can be mixed into the polyethylene wherein the heated mixture can be stirred until the mixture is homogeneous, or at least substantially homogeneous. Thereafter, the mixture can be injected into one or more cavities of a mold such that the mixture can then cool below the melting temperature of the polyethylene material and take the shape of the mold cavity. Once the mixture has been sufficiently cooled, the mold can be opened and the molded pressure-sensitive material can be removed from the cavity. In various circumstances, the pressure-sensitive material can then be exposed to gamma radiation which can at least partially crystallize the polyethylene. In various embodiments, the material can be exposed to two doses of approximately 15-20 kGy each, for example, resulting in approximately 40 kGy maximum total exposure, for example. In various circumstances, the gamma radiation process can cause the carbon black particles to migrate and accumulate in pockets intermediate the crystallized portions of the polyethylene. In various embodiments, the carbon black particles can comprise an average diameter of approximately 10 microns, for example, and can comprise any suitable geometry and/or configuration such as bucky balls and/or tubular ferrules, for example. In any event, in the event that the electrodes comprising such pressure-sensitive materials are to be sterilized, it may be desirable to avoid sterilizing the electrodes using gamma radiation as doing so may affect the performance characteristics of the pressure-sensitive materials in some circumstances. Other sterilization processes, such as those utilizing ethylene oxide, for example, could be used.

Figure 34:
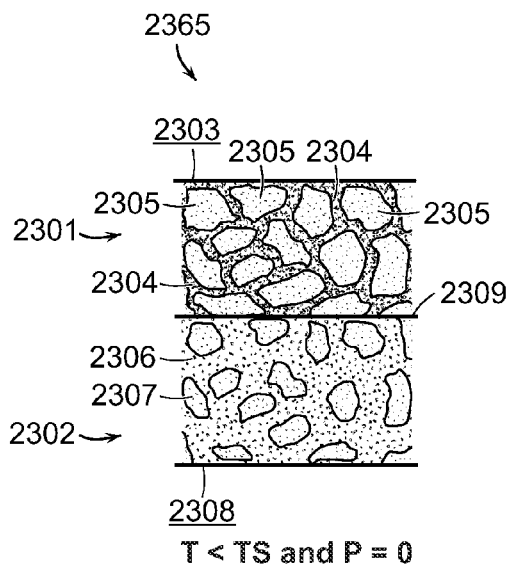
FIG. 34 is a cross-sectional view of an electrode in accordance with at least one embodiment, wherein the electrode comprises a first layer including a positive temperature coefficient (PTC) material and a second layer including a pressure sensitive (PS) material. The view depicts the PTC material in a condition to conduct electrical current therethrough while the PS material is depicted in a condition which inhibits the flow of electrical current therethrough.

In various embodiments, referring now to FIGS. 34-37, a surgical instrument can comprise one or more electrodes utilizing both a pressure-sensitive (PS) material and a positive temperature coefficient (PTC) material. Referring primarily to FIG. 34, an electrode 2365 can comprise a first, or top, layer 2301 comprising a PTC material and a second, or bottom, layer 2302 comprising a PS material. In various embodiments, similar to the above, the PTC material of the first layer 2301 can comprise a non-conductive, or at least substantially non-conductive, substrate 2304 and conductive particles 2305 dispersed therein. Also similar to the above, the PS material of the second layer 2302 can comprise a non-conductive, or at least substantially non-conductive, substrate 2306 and conductive particles 2307 dispersed therein. The electrode 2365 can further comprise a support, or bottom, surface 2308 configured to support the electrode 2365 within a jaw member of an electrosurgical instrument, for example, wherein, in certain embodiments, the electrode 2365 can further comprise a conductive sheet attached to bottom surface 2308. In at least one such embodiment, the conductive sheet can be adhered to the bottom surface 2308 utilizing an adhesive while, in other embodiments, the conductive sheet may be unattached to the electrode 2365 and the bottom surface 2308 may abut the conductive sheet. In any event, a conductor, such as an insulated wire, for example, may be electrically coupled with the conductive sheet such that a voltage potential can be applied to the bottom surface 2308 of the electrode 2365. On the opposite side of the electrode 2365, the electrode 2365 can further comprise a tissue-contacting surface 2303 which can be configured to contact tissue positioned between a jaw including electrode 2365 and an opposing jaw positioned on the opposite side of the tissue. In at least one such embodiment, the opposing jaw can comprise an electrode 2365 positioned in a mirror-image arrangement such that the tissue-contacting surfaces 2303 of the electrodes 2365 face one another.

In various embodiments, further to the above, the first layer 2301 can comprise means for controlling and/or evaluating the temperature of the tissue and, in addition, the second layer 2302 can comprise means for assuring that the current cannot flow through the electrode 2365 until the tissue being treated by the electrode 2365 is positioned against tissue-contacting surface 2303 with sufficient pressure. In at least one such embodiment, the PTC material of layer 2301 can comprise a thermal switch and the PS material of layer 2302 can comprise a pressure switch which can be configured to co-operate with one another in order to assure that temperature of the tissue being treated does not exceed a certain temperature and such that the tissue being treated is being sufficiently compressed. Referring again to FIG. 34, the PTC material of first layer 2301 is illustrated as being below its switching temperature Ts and, as a result, the conductive particles 2305 in substrate 2304 are sufficiently in contact with one another in order for current to be conducted through the first layer 2301. The PS material of second layer 2302, however, is illustrated in FIG. 34 as being below its switching pressure Ps and, as a result, the conductive particles 2307 in substrate 2306 are not sufficiently in contact with one another in order for current to be conducted through layer 2302, at least not in a magnitude sufficient to generate therapeutic and/or irreversible effects within the tissue positioned against tissue-contacting surface 2303. In such circumstances, as a result, the resistance between surfaces 2303 and 2308 is too large for a sufficient current, if any, to be transmitted between the surfaces 2303 and 2308 in order to treat the tissue, at least for the voltage potential applied to the bottom surface 2308, for example.

Referring again to FIG. 34, the reader will note that the substrate 2304 of first layer 2301 is illustrated as being shaded-in, or darkened, while the substrate 2306 of second layer 2302 is illustrated as not being shaded-in. This has been done in order to schematically illustrate, by way of example, that the darkened first layer 2301 comprises a "closed" portion of the series circuit between surfaces 2303 and 2308 and that the non-darkened second layer 2302 comprises an "open" portion of the series circuit. In various circumstances, the term "closed" can designate that current could flow through that portion of the circuit with a sufficient amplitude in order to therapeutically treat, and/or irreversibly affect, the tissue, whereas the term "open" can designate that current cannot flow through that portion of the circuit with a sufficient amplitude to therapeutically treat, and/or irreversibly affect, the tissue. In certain circumstances, the term "open" can designate that the current can flow through that portion of the circuit at all. In various circumstances, if one or both layers 2301 and 2302 represent an open part of the circuit between surfaces 2303 and 2308, the entire circuit between surfaces 2303 and 2308 will, as a result, be open. In circumstances where both layers 2301 and 2302 are closed, the entire series circuit between surfaces 2303 and 2308 will be closed and sufficient therapeutic current can flow therethrough.

Figure 35:
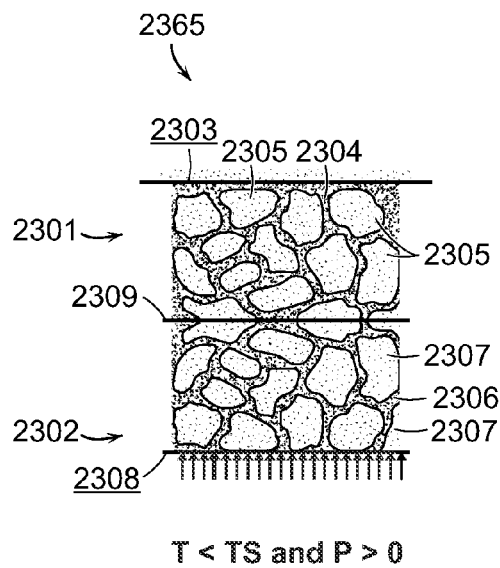
FIG. 35 is a cross-sectional view of the electrode of FIG. 34. The view depicts both the PTC material and the PS material in a condition to conduct electrical current therethrough.

Referring now to FIG. 35, further to the above, the PTC material of the first layer 2301 is illustrated as being below its switching temperature Ts and, as a result, the conductive particles 2305 in substrate 2304 are sufficiently in contact with one another in order for current to be conducted through the first layer 2301. As the reader will note, substrate 2304 is correspondingly illustrated as being shaded-in or darkened as it is in a "closed" condition. Still referring to FIG. 35, the PS material of second layer 2302 is illustrated as being above its switching pressure Ps and, as a result, the conductive particles 2307 in substrate 2306 are sufficiently in contact with one another in order for current to be conducted through the second layer 2302. As the reader will note, substrate 2306 is illustrated as being shaded-in or darkened as it is also in a "closed" condition. As a result of the above, the series circuit between surfaces 2303 and 2308 is in a "closed" condition and, accordingly, sufficient therapeutic current can flow through between surfaces 2303 and 2308 of the electrode 2365. The state of the electrode 2365 in FIG. 35 can represent the condition in which the electrosurgical instrument comprising the electrode 2365 has captured and clamped tissue within the end effector and can be utilized to treat the tissue. In various embodiments, a voltage potential between approximately 60 V and approximately 105 V, for example, can be applied to the electrode 2365 in order to treat the tissue. In at least one embodiment, a voltage potential of approximately 85 V, for example, can be applied to the electrode 2365. In certain embodiments, a maximum voltage potential, such as 105 V, for example, can be set in order to reduce the possibility of the electrode material breaking down and creating a short within the electrode material, for example.

Figure 36:
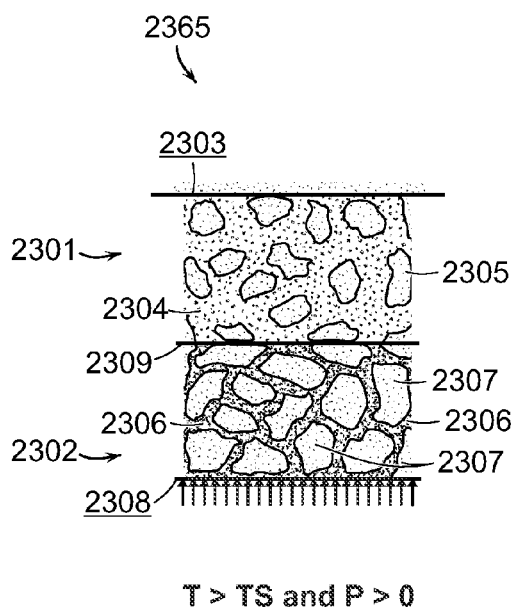
FIG. 36 is a cross-sectional view of the electrode of FIG. 34. The view depicts the PS material in a condition to conduct electrical current therethrough while the PTC material is depicted in a condition which inhibits the flow of electrical current therethrough.
Figure 37:
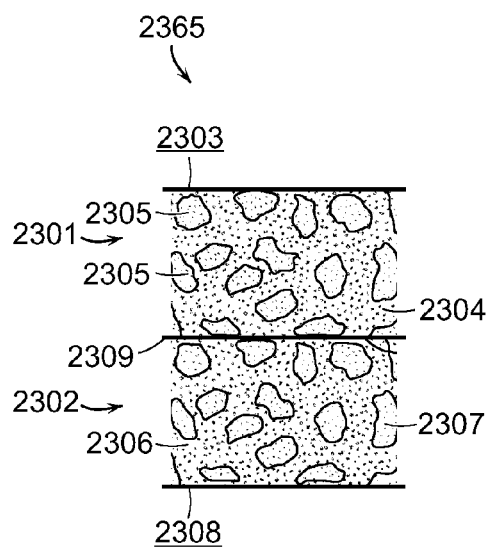
FIG. 37 is a cross-sectional view of the electrode of FIG. 34. The view depicts both the PTC material and the PS material in a condition which inhibits the flow of electrical current therethrough.

Referring now to FIG. 36, the PTC material of the first layer 2301 is illustrated as being above its switching temperature Ts and, as a result, the conductive particles 2305 in substrate 2304 are not sufficiently in contact with one another in order for current to be conducted through layer 2301, at least not in a magnitude sufficient to generate therapeutic and/or irreversible effects within the tissue positioned against tissue-contacting surface 2303. As the reader will note, substrate 2304 is correspondingly illustrated as being non-darkened as it is in an "open" condition. Accordingly, the series circuit between surfaces 2303 and 2308 is in an "open" condition eventhough the pressure applied to electrode 2365 is above the switching pressure Ps and the second layer 2302 is in a "closed" configuration. Referring now to FIG. 37, the PTC material of the first layer 2301 is illustrated as being above its switching temperature Ts and the second layer 2302 is illustrated as being below its switching pressure Ps. As a result, both layers 2301 and 2302 are "open" and are illustrated as being non-darkened. Accordingly, the series circuit between surfaces 2303 and 2308 is in an "open" condition. In various alternative embodiments, one or both of the first and second layers 2301 and 2302 may not act as switches; rather, one or both of the layers 2301 and 2302 may provide variable resistances depending on the temperature and pressure, respectively, being applied to the tissue. More particularly, in at least one embodiment, the PTC and/or PS materials may not switch between open and closed conditions; rather, the electrical resistances of the materials may change linearly and/or geometrically in a monotonical manner, wherein the resistance of the PTC material of the first layer 2301 may increase as the temperature of the tissue increases, and wherein the resistance of the PS material of the second layer 2302 may decrease as the pressure applied to the tissue increases.

In various embodiments, further to the above, the first layer 2301 can be stacked on top of the second layer 2302 such that they have abutting faces at interface 2309. In certain embodiments, the first layer 2301 can be adhered to the second layer 2302. In at least one embodiment, the first layer 2301 and the second layer 2302 can be co-extruded such that they form a bonded interface therebetween. In at least one such embodiment, the PTC material comprising the first layer 2301 can be positioned on top of the PS material comprising the second layer 2302 such that the assembled materials can be fed through a die and, as a result of pressure and/or temperature being applied to the PTC and PS materials, the layers 2301 and 2302 can form at least one of a mechanical bond and a chemical bond therebetween. Stated another way, the layers 2301 and 2302 can be co-extruded.

As discussed above, a pressure-sensitive (PS) material can either prevent and/or limit the flow of current passing therethrough as a function of the pressure being applied to the PS material. In at least one such embodiment, as also described above, the PS material can comprise a pressure switch which change between a high electrical resistance and a low electrical resistance depending on whether the applied pressure is below or above, respectively, the switching pressure Ps. In various embodiments, a PS material can also comprise certain characteristics of a positive temperature coefficient (PTC) material. More particularly, in at least one embodiment, once a sufficient pressure has been applied to the PS material and the conductive particles within the substrate of the PS material have been sufficiently squeezed together such that the PS material is capable of conducting therapeutic current therethrough, such current can cause the PS material to increase in temperature. Owing to the increase in temperature, the PS material substrate can begin to expand and/or change state such that the conductive particles are no longer in contact with each other, or at least sufficiently in contact with one another, in order to conduct a therapeutic current therethrough. In various circumstances, as a result, the PS material can also act as a temperature switch wherein, in at least one embodiment, the PS material can go through three states: a first state which is "open" owing to the pressure switching characteristics of the material, a second state which is "closed", and a third state which is "open" owing to the temperature switching characteristics of the material. More particularly, the material can have a first state having a first resistance which is sufficiently high to prevent or inhibit current from flowing therethrough before the switching pressure is applied, a second state having a second resistance which is sufficiently low to allow a therapeutic current to flow therethrough, and a third state having a third resistance which is sufficiently high to prevent or inhibit current from flowing therethrough because the switching temperature has been exceeded, for example.

The embodiments of the devices described herein may be introduced inside a patient using minimally invasive or open surgical techniques. In some instances it may be advantageous to introduce the devices inside the patient using a combination of minimally invasive and open surgical techniques. Minimally invasive techniques may provide more accurate and effective access to the treatment region for diagnostic and treatment procedures. To reach internal treatment regions within the patient, the devices described herein may be inserted through natural openings of the body such as the mouth, anus, and/or vagina, for example. Minimally invasive procedures performed by the introduction of various medical devices into the patient through a natural opening of the patient are known in the art as NOTES™ procedures. Some portions of the devices may be introduced to the tissue treatment region percutaneously or through small—keyhole—incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina) or via a trocar through a relatively small—keyhole—incision incisions (usually 0.5-1.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

The devices disclosed herein may be designed to be disposed of after a single use, or they may be designed to be used multiple times. In either case, however, the device may be reconditioned for reuse after at least one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
a handle; and
an end effector, comprising:
   a first jaw;
   a second jaw, wherein said first jaw is movable relative to said second jaw between an open position and a closed position;
   a first electrode comprising a first positive temperature coefficient material interspersed throughout said first electrode, wherein said first positive temperature coefficient material comprises a first electrical resistance when the temperature of said first electrode is below a first switching temperature, and wherein said first positive temperature coefficient material comprises a second electrical resistance when the temperature of said first electrode is above said first switching temperature; and a second electrode comprising a second positive temperature coefficient material interspersed throughout said second electrode, wherein said second positive temperature coefficient material comprises a first electrical resistance when the temperature of the second electrode is below a second switching temperature, wherein said second positive temperature coefficient material comprises a second electrical resistance when the temperature of said second electrode is above said second switching temperature, and wherein said second switching temperature is higher than said first switching temperature.

2. The surgical instrument of claim 1, wherein said first electrode is positioned around said second electrode.

3. The surgical instrument of claim 1, wherein said end effector comprises a central axis, and wherein said second electrode is positioned closer to said central axis than said first electrode.

4. The surgical instrument of claim 1, further comprising a third electrode comprised of a third positive temperature coefficient material, wherein said third positive temperature coefficient material comprises a first electrical resistance when the temperature of said third electrode is below a third switching temperature, wherein said third positive temperature coefficient material comprises a second electrical resistance when the temperature of said third electrode is above said third switching temperature, and wherein said third switching temperature is higher than said second switching temperature.

5. The surgical instrument of claim 4, wherein said end effector comprises a central axis, wherein said third electrode is positioned closer to said central axis than said second electrode, and wherein said second electrode is positioned closer to said central axis than said first electrode.

6. The surgical instrument of claim 1, wherein said first electrode and said second electrode are positioned within said first jaw, and wherein said second jaw comprises an opposing electrode which is positioned opposite said first electrode and said second electrode when said first jaw is in said closed position.

7. The surgical instrument of claim 1, wherein said first jaw comprises a first outer perimeter and said second jaw comprises a second outer perimeter, and wherein at least one of said first outer perimeter and said second outer perimeter is comprised of a positive temperature coefficient material comprising a switching temperature lower than said first switching temperature and said second switching temperature.

8. A surgical instrument, comprising:
a handle; and
an end effector, comprising:
a first jaw;
a second jaw, wherein said first jaw is movable relative to said second jaw;
a first electrode positioned within said first jaw and comprised of a first positive temperature coefficient material, wherein said first positive temperature coefficient material comprises a first electrical resistance when the temperature of said first electrode is below a first switching temperature, and wherein said first positive temperature coefficient material comprises a second electrical resistance at least one order of magnitude higher than said first resistance when the temperature of said first electrode is above said first switching temperature; and a second electrode comprised of a second positive temperature coefficient material, wherein said second positive temperature coefficient material comprises a third electrical resistance when the temperature of the second electrode is below a second switching temperature, wherein said second positive temperature coefficient material comprises a fourth electrical resistance at least one order of magnitude higher than said third electrical resistance when the temperature of said second electrode is above said second switching temperature, and wherein said second switching temperature is higher than said first switching temperature.

9. The surgical instrument of claim 8, wherein said first electrode is positioned around said second electrode, and wherein said second electrical resistance of said first electrode is less than said fourth electrical resistance of said second electrode.

10. The surgical instrument of claim 8, wherein said end effector comprises a central axis, wherein said second electrode is positioned closer to said central axis than said first electrode, and wherein said second electrical resistance of said first electrode is less than said fourth electrical resistance of said second electrode.

11. The surgical instrument of claim 8, further comprising a third electrode comprised of a third positive temperature coefficient material, wherein said third positive temperature coefficient material comprises a fifth electrical resistance when the temperature of said third electrode is below a third switching temperature, wherein said third positive temperature coefficient material comprises a sixth electrical resistance when the temperature of said third electrode is above said third switching temperature, and wherein said third switching temperature is higher than said second switching temperature.

12. The surgical instrument of claim 11, wherein said end effector comprises a central axis, wherein said third electrode is positioned closer to said central axis than said second electrode, wherein said second electrode is positioned closer to said central axis than said first electrode, wherein said second electrical resistance of said first electrode is less than said fourth electrical resistance of said second electrode, and wherein said fourth electrical resistance of said second electrode is less than said sixth electrical resistance of said third electrode.

13. The surgical instrument of claim 8, wherein said first electrode and said second electrode are positioned within said first jaw, and wherein said second jaw comprises an opposing electrode which is positioned opposite said first electrode and said second electrode when said first jaw is in a closed position.

14. The surgical instrument of claim 8, wherein said first jaw comprises a first outer perimeter and said second jaw comprises a second outer perimeter, and wherein at least one of said first outer perimeter and said second outer perimeter is comprised of a positive temperature coefficient material comprising a switching temperature lower than said first switching temperature and said second switching temperature.

* * * * *